United States Patent
Samajdar et al.

(10) Patent No.: US 10,590,118 B2
(45) Date of Patent: Mar. 17, 2020

(54) BICYCLIC HETEROCYCLIC DERIVATIVES AS BROMODOMAIN INHIBITORS

(71) Applicant: Orion Corporation, Espoo (FI)

(72) Inventors: Susanta Samajdar, Bangalore (IN); Chandrasekhar Abbineni, Hyderabad (IN); Sanjita Sasmal, Hyderabad (IN); Subramanya Hosahalli, Bangalore (IN)

(73) Assignee: ORION CORPORATION, Espoo (FI)

( * ) Notice: Subject to any disclaimer, the term of this patent is extended or adjusted under 35 U.S.C. 154(b) by 0 days.

(21) Appl. No.: 16/051,913

(22) Filed: Aug. 1, 2018

(65) Prior Publication Data

US 2018/0339982 A1     Nov. 29, 2018

Related U.S. Application Data

(62) Division of application No. 15/110,361, filed as application No. PCT/IB2015/050090 on Jan. 6, 2015, now Pat. No. 10,077,259.

(30) Foreign Application Priority Data

Jan. 9, 2014 (IN) .............................. 125/CHE/2014

(51) Int. Cl.
| | |
|---|---|
| *A61K 31/536* | (2006.01) |
| *A61K 31/498* | (2006.01) |
| *A61P 37/00* | (2006.01) |
| *A61P 29/00* | (2006.01) |
| *A61P 35/00* | (2006.01) |
| *C07D 401/14* | (2006.01) |
| *C07D 413/14* | (2006.01) |
| *C07D 413/04* | (2006.01) |
| *C07D 417/12* | (2006.01) |

(52) U.S. Cl.
CPC .......... *C07D 413/04* (2013.01); *C07D 401/14* (2013.01); *C07D 413/14* (2013.01); *C07D 417/12* (2013.01)

(58) Field of Classification Search
CPC ..... A61K 31/536; A61K 31/498; A61P 37/00; A61P 29/00; A61P 35/00; C07D 401/14; C07D 413/14; C07D 413/04
See application file for complete search history.

(56) References Cited

FOREIGN PATENT DOCUMENTS

| WO | WO 2011/054848 A1 | 5/2011 |
| WO | WO 2012/143415 A1 | 10/2012 |
| WO | WO 2012/150234 A1 | 11/2012 |
| WO | WO 2013/027168 A1 | 2/2013 |
| WO | WO 2014/154762 A1 | 10/2014 |
| WO | WO 2014/159837 A1 | 10/2014 |

OTHER PUBLICATIONS

International Search Report for PCT/IB2015/050090 dated Mar. 9, 2015.
Written Opinion of International Searching Authority Mar. 9, 2015.

*Primary Examiner* — Brenda L Coleman
(74) *Attorney, Agent, or Firm* — Finnegan, Henderson, Farabow, Garrett & Dunner, L.L.P.

(57) ABSTRACT

The present disclosure provides bicyclic heterocyclic derivatives of formula (I), which may be therapeutically useful, more particularly as bromodomain inhibitors; (I), in which $R_1$, $R_2$, $R_3$, $R_4$, $L_1$, $L_2$, $Cy_1$, $Cy_2$, X, n, and dotted line have the same meaning given in the specification, and pharmaceutically acceptable salts or pharmaceutically acceptable stereoisomers thereof that are useful in the treatment and prevention of diseases or disorders, in particular their use in diseases or disorders associated as bromodomain inhibitors. The present disclosure also provides preparation of compounds and pharmaceutical formulations comprising at least one of bicyclic heterocyclic derivatives of formula (I), together with a pharmaceutically acceptable carrier, diluent, or excipient.

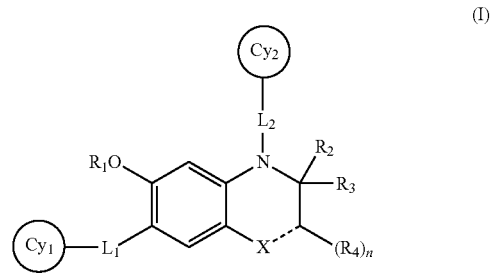

9 Claims, No Drawings

BICYCLIC HETEROCYCLIC DERIVATIVES AS BROMODOMAIN INHIBITORS

This is divisional of pending Application No. 15/110,361, filed Jul. 7, 2016, which is a national stage application under § 371 of International Patent Application No. PCT/IB2015/050090, filed Jan. 6, 2015, which claims the benefit of Indian provisional application number 125/CHE/2014 filed on 9 Jan. 2014, all of which are incorporated herein by reference.

FIELD OF THE INVENTION

The present invention relates to bicyclic heterocyclic derivatives of formula (I) which are useful as bromodomain inhibitors.

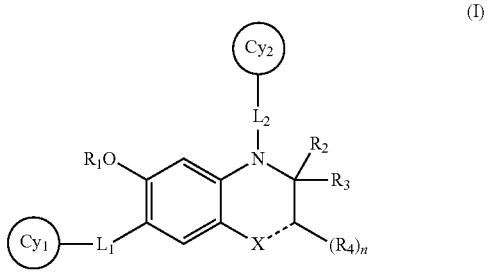

(I)

The invention also relates to process for preparation thereof, pharmaceutical compositions comprising them, and their use for treatment and prevention in diseases or disorder, in particular their use in treatment of diseases or disorder associated with bromodomain inhibition.

BACKGROUND OF THE INVENTION

The acetylation of histone lysine is central to providing the dynamic regulation of chromatin-based gene transcription. The bromodomain (BRD), which is the conserved structural module in chromatin-associated proteins and histone acetyltranferases, is the sole protein domain known to recognize acetyl-lysine residues on proteins.

The BET family of bromodomain containing proteins comprises 4 proteins (BRD2, BRD3, BRD4 and BRD-t) which contain tandem bromodomains capable of binding to two acetylated lysine residues in close proximity, increasing the specificity of the interaction. BRD2 and BRD3 are reported to associate with histones along actively transcribed genes and may be involved in facilitating transcriptional elongation (Leroy et al, Mol. Cell. 2008 30(1):51-60), while BRD4 appears to be involved in the recruitment of the pTEF-[beta] complex to inducible genes, resulting in phosphorylation of RNA polymerase and increased transcriptional output (Hargreaves et al, Cell, 2009 138(1): 129-145). It has also been reported that BRD4 or BRD3 may fuse with NUT (nuclear protein in testis) forming novel fusion oncogenes, BRD4-NUT or BRD3-NUT, in a highly malignant form of epithelial neoplasia (French et al. Cancer Research, 2003, 63, 304-307 and French et al. Journal of Clinical Oncology, 2004, 22 (20), 4135-4139). Data suggests that BRD-NUT fusion proteins contribute to carcinogenesis (Oncogene, 2008, 27, 2237-2242). BRD-t is uniquely expressed in the testes and ovary. All family members have been reported to have some function in controlling or executing aspects of the cell cycle, and have been shown to remain in complex with chromosomes during cell division suggesting a role in the maintenance of epigenetic memory. In addition some viruses make use of these proteins to tether their genomes to the host cell chromatin, as part of the process of viral replication (You et al Cell, 2004 117(3):349-60).

Japanese patent application JP2008156311 discloses a benzimidazole derivative which is said to be a BRD2 bromodomain binding agent has utility with respect to virus infection/proliferation.

International patent application WO2009084693A1 discloses a series of thienotriazolodiazepiene derivatives that are said to inhibit the binding between an acetylated histone and a bromodomain containing protein which are said to be useful as anti-cancer agents.

International patent application WO2011054846A1 discloses a series of quinoline derivatives that inhibit the binding of BET family bromodomains with acetylated lysine residues.

However, there remains a need for potent bromodomain inhibitors with desirable pharmaceutical properties. Certain bicyclic heterocyclic derivatives have been found in the context of this invention to have a class of compounds that inhibit the binding of BET family bromodomains to acetylated lysine residues for controlling the gene expressions in human health and disease. Such compounds will hereafter be referred to as "bromodomain inhibitors".

SUMMARY OF THE INVENTION

The present invention provides bicyclic heterocyclic derivatives of the formula (I) that inhibit the binding of BET family bromodomains to acetylated lysine residues.

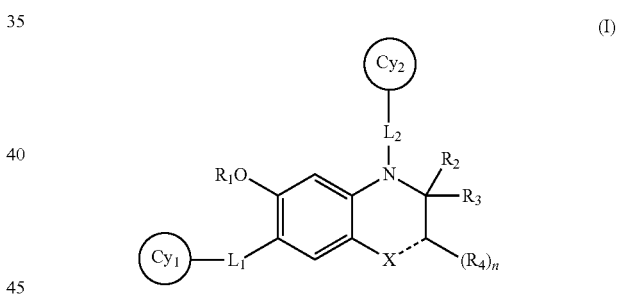

(I)

or a pharmaceutically acceptable salt or a pharmaceutically acceptable stereoisomer thereof;
wherein,
dotted line[---] represents a single or a double bond;
X is selected from C, C(O), N or O; wherein C and N are substituted with one or more $R_5$ to meet the desired valency requirements;
$L_1$ is a direct bond or a linker selected from —NH—, —NHC(O)— or —NHS(O)$_2$—;
$L_2$ is a linker selected from —(CHR$_6$)$_n$—, —C(O)— or —S(O)$_2$—;
Cy$_1$ is an optionally substituted 5-6 membered monocyclic ring containing 1-4 hetero atoms/hetero groups independently selected form N, NH, O or —C(O)—; wherein the optional substituent at each occurrence is independently selected from one or more $R_7$;
Cy$_2$ is an optionally substituted 4-12 membered monocyclic or bicyclic ring containing 0-3 hetero atoms/groups independently selected form N, NH, O or S; wherein the optional substituent at each occurrence is independently selected from one or more $R_8$;

$R_1$ is selected from hydrogen, alkyl, alkenyl, haloalkyl, hydroxyalkyl, alkoxyalkyl, aminoalkyl, heterocyclyl or heterocyclylalkyl;

$R_2$ and $R_3$ independently are hydrogen, alkyl or together form an oxo group;

$R_4$ at each occurrence is independently selected from hydrogen, alkyl, cycloalkyl, cyanoalkyl, hydroxyalkyl, or optionally substituted haloalkyl; wherein the optional substituent is one or more hydroxyl;

$R_5$ at each occurrence is independently selected from hydrogen, alkyl, haloalkyl, cycloalkyl or cyano;

$R_6$ is hydrogen or alkyl;

$R_7$ is selected from alkyl, hydroxy or cycloalkyl;

$R_8$ is selected from alkyl, alkoxy, amino, cyano, halogen, haloalkyl, hydroxy, —C(O)alkyl or optionally substituted heterocyclyl; wherein the optional substituent is selected from one or more alkyl or hydroxy; and n is an integer selected from 1 or 2.

In one aspect of the present invention, it relates to pharmaceutical composition comprising bicyclic heterocyclic derivatives of formula (I) and processes for preparing thereof.

In yet another aspect of the present invention, it provides use of bicyclic heterocyclic derivatives of formula (I) for the treatment and prevention in diseases or disorder, in particular their use in diseases or disorder for which a bromodomain inhibitor is indicated.

In further yet another aspect, the invention relates to use of novel bicyclic heterocyclic derivatives of formula (I) or a pharmaceutically acceptable salt or a pharmaceutically acceptable stereoisomer thereof, including mixtures thereof in all ratios as a medicament for which a bromodomain inhibitor is indicated.

DETAILED DESCRIPTION OF THE INVENTION

An embodiment of the present invention provides bicyclic heterocyclic derivatives of formula (I) useful as bromodomain inhibitors.

One of the embodiments of the present invention relates to compounds of formula (I):

(I)

or a pharmaceutically acceptable salt or a pharmaceutically acceptable stereoisomer thereof; wherein, dotted line[---] represents a single or a double bond;

X is selected from C, C(O), N or O; wherein C and N are substituted with one or more $R_5$ to meet the desired valency requirements;

$L_1$ is a direct bond or a linker selected from —NH—, —NHC(O)— or —NHS(O)$_2$—;

$L_2$ is a linker selected from —(CHR$_6$)$_n$—, —C(O)— or —S(O)$_2$—;

$Cy_1$ is an optionally substituted 5-6 membered monocyclic ring containing 1-4 hetero atoms/hetero groups independently selected form N, NH, O or —C(O)—; wherein the optional substituent at each occurrence is independently selected from one or more $R_7$;

$Cy_2$ is an optionally substituted 4-12 membered monocyclic or bicyclic ring containing 0-3 hetero atoms/groups independently selected form N, NH, O or S; wherein the optional substituent at each occurrence is independently selected from one or more $R_8$;

$R_1$ is selected from hydrogen, alkyl, alkenyl, haloalkyl, hydroxyalkyl, alkoxyalkyl, aminoalkyl, heterocyclyl or heterocyclylalkyl;

$R_2$ and $R_3$ independently are hydrogen, alkyl or together form an oxo group;

$R_4$ at each occurrence is independently selected from hydrogen, alkyl, cycloalkyl, cyanoalkyl, hydroxyalkyl, or optionally substituted haloalkyl; wherein the optional substituent is one or more hydroxyl;

$R_5$ at each occurrence is independently selected from hydrogen, alkyl, haloalkyl, cycloalkyl or cyano;

$R_6$ is hydrogen or alkyl;

$R_7$ is selected from alkyl, hydroxy or cycloalkyl;

$R_8$ is selected from alkyl, alkoxy, amino, cyano, halogen, haloalkyl, hydroxy, —C(O)alkyl or optionally substituted heterocyclyl; wherein the optional substituent is selected from one or more alkyl or hydroxy; and n is an integer selected from 1 or 2.

The embodiments below are illustrative of the present invention and are not intended to limit the claims to the specific embodiments exemplified.

According to one embodiment, specifically provided are compounds of the formula (I), in which X is selected from O, N, C(O), CH$_2$, CH, C(R$_5$)$_2$ or CR$_5$.

According to above embodiment, $R_5$ is selected from alkyl, haloalkyl, cycloalkyl or cyano; in particular alkyl is methyl, haloalkyl is —CF$_3$ and cycloalkyl is cyclopropyl.

According to other embodiment, specifically provided are compounds of the formula (I), in which $L_1$ is a direct bond.

According to yet another embodiment, specifically provided are compounds of the formula (I), in which $L_1$ is a linker selected from —NH—, —NHC(O)— or —NHS(O)$_2$—.

According to further yet another embodiment, specifically provided are compounds of the formula (I), in which $Cy_1$ is selected from optionally substituted 5- or 6-membered monocyclic ring containing 1-3 hetero atoms/hetero groups independently selected form N, NH, O or —C(O)—.

According to preceding embodiment, $Cy_1$ is selected from the group consisting of

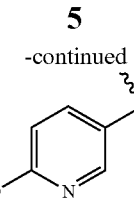

According to further yet another embodiment, specifically provided are compounds of the formula (I), in which $L_2$ is selected from —$(CHR_6)_n$—, —C(O)— or —$S(O)_2$—; in which 'n' is an integer selected from 1 or 2 and $R_6$ is selected from hydrogen or alkyl; in particular alkyl is methyl.

According to further yet another embodiment, specifically provided are compounds of the formula (I), in which $Cy_2$ is selected from optionally substituted 5- or 6-membered monocyclic ring or 12 membered bicyclic ring containing 0-3 hetero atoms/groups independently selected from N, N(H), O or S.

According to preceding embodiment, $Cy_2$ is selected from the group consisting of thiazole, pyrazine, tetrahydro-2H-pyran, morpholine, pyrimidine, quinoline, optionally substituted piperidine, optionally substituted phenyl or optionally substituted pyridyl.

According to preceding embodiments, optional substituents are selected from halogen, alkoxy, amino, cyano, alkyl, haloalkyl, hydroxy, —C(O)alkyl and heterocyclyl: in particular alkyl is methyl, halogen is fluoro, chloro or bromo, alkoxy is methoxy, —C(O)alkyl is propan-1-one, and heterocyclyl is pyrrolidin-3-ol, 3,5-dimethyl-1H-pyrazole and 1-methyl-1H-pyrazole.

According to further yet another embodiment, specifically provided are compounds of the formula (I), in which $R_1$ is hydrogen, alkyl, alkenyl, haloalkyl, hydroxyalkyl, alkoxyalkyl or alkyl substituted aminoalkyl; in particular alkyl is methyl or butyl, alkenyl is prop-1-ene, hydroxyalkyl is —$(CH_2)_2OH$ or —$(CH_2)_3OH$, haloalkyl is —$CF_3$ or —$CH_2CF_3$, alkoxyalkyl is methoxyethyl, and aminoalkyl is dimethylaminoethyl.

According to further yet another embodiment, specifically provided are compounds of the formula (I), in which $R_1$ is heterocyclyl or heterocyclylalkyl; in particular heterocyclyl is piperidine, and heterocyclylalkyl is morpholinyl-ethyl, piperdinyl-methyl, piperdinyl-ethyl, piperazinyl-ethyl, pyridyl-methyl, tetrahydropyran-methyl and pyrrolidinyl-ethyl.

According to further yet another embodiment, specifically provided are compounds of the formula (I), in which $R_4$ is hydrogen, alkyl, cycloalkyl, cyanoalkyl, hydroxyalkyl or optionally substituted haloalkyl; in particular alkyl is methyl cycloalkyl is cyclohexyl, cyanoalkyl is —$CH_2CN$, hydroxyalkyl is —$CH_2OH$; and optionally substituted haloalkyl is —$CH_2F$, —$CH(OH)CF_3$ or —$C(OH)(OH)CF_3$.

According to yet another embodiment of the present invention, the compound of formula (I) is a compound of formula (Ia):

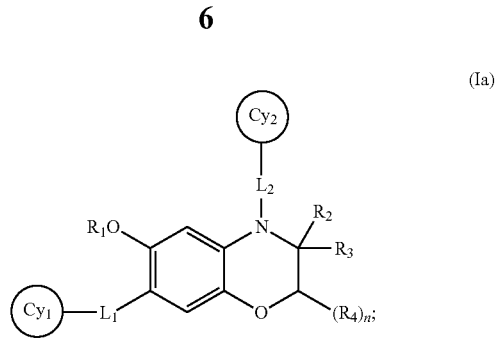

wherein, $R_1$, $R_2$, $R_3$, $R_4$, $Cy_1$, $Cy_2$, $L_1$, $L_2$ and 'n' are same as defined in formula (I); or a pharmaceutically acceptable salt or a pharmaceutically acceptable stereoisomer thereof.

According to yet another embodiment of the present invention, the compound of formula (I) is a compound of formula (Ib):

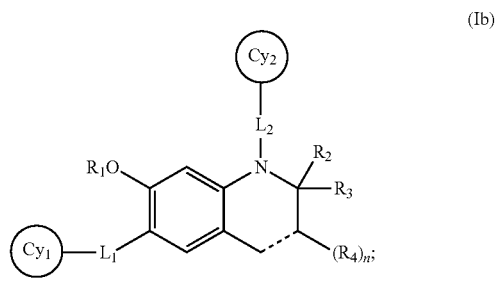

wherein, $R_1$, $R_2$, $R_3$, $R_4$, $Cy_1$, $Cy_2$, $L_1$, $L_2$ and 'n' are same as defined in formula (I):

or a pharmaceutically acceptable salt or a pharmaceutically acceptable stereoisomer thereof.

According to yet another embodiment of the present invention, the compound of formula (I) is a compound of formula (Ic):

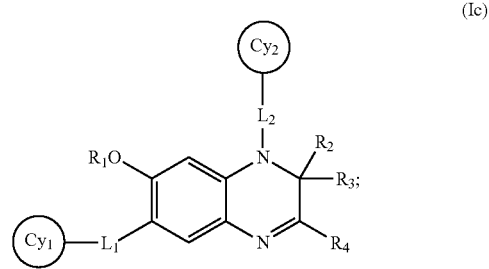

wherein, $R_1$, $R_2$, $R_3$, $R_1$, $Cy_1$, $Cy_2$, $L_1$, $L_2$ and 'n' are same as defined in formula (I);

or a pharmaceutically acceptable salt or a pharmaceutically acceptable stereoisomer thereof.

In yet another particular embodiment of the present invention, the compound of formula (I) is selected from the group consisting of:

| Compound. No | IUPAC Name |
|---|---|
| 1. | 4-(4-chlorobenzyl)-7-(3,5-dimethylisoxazol-4-yl)-6-methoxy-3,4-dihydro-2H-benzo[b][1,4]oxazine; |
| 2. | 6-(3,5-dimethyisoxazol-4-yl)-7-methoxy-1-((5-methoxypyridin-2-yl)methyl)quinolin-2(1H)-one; |
| 3. | 6-(3,5-dimethyl-4H-1,2,4-triazol-4-yl)-7-methoxy-1-(pyridin-2-ylmethyl)quinolin-2(1H)-one; |
| 4. | 1-(4-chlorobenzyl)-6-(3,5-dimethylisoxazol-4-yl)-7-methoxyquinoxalin-2(1H)-one; |
| 5. | 1-(4-chlorobenzyl)-6-(3,5-dimethyisoxazol-4-yl)-7-methoxy-3,4-dihydroquinolin-2(1H)-one; |
| 6 | 4-(1-(4-chlorophenyl)ethyl)-7-(3,5-dimethylisoxazol-4-yl)-6-methoxy-3,4-dihydro-2H-benzo[b][1,4]oxazine; |
| 7. | 7-(3,5-dimethylisoxazol-4-yl)-6-methoxy-4-(1-(pyridin-3-yl)ethyl)-3,4-dihydro-2H-benzo[b][1,4]oxazine; |
| 8. | 6-(3,5-dimethylisoxazol-4-yl)-7-methoxy-1-(pyrazin-3-ylmethyl)quinolin-2(1H)-one; |
| 9. | 6-(3,5-dimethylisoxazol-4-yl)-1-((3-fluoropyridin-2-yl)methyl)-7-methoxyquinolin-2(1H)-one; |
| 10. | 6-(3,5-dimethylisoxazol-4-yl)-7-methoxy-1-(pyridin-2-ylmethyl)-3,4-dihydroquinolin-2(1H)-one; |
| 11. | 4-((3-chlorophenyl)sulfonyl)-7-(3,5-dimethylisoxazol-4-yl)-6-methoxy-3,4-dihydro-2H-benzo[b][1,4]oxazine; |
| 12. | 7-(3,5-dimethylisoxazol-4-yl)-6-methoxy-4-(pyridin-3-ylsulfonyl)-3,4-dihydro-2H-benzo[b][1,4]oxazine; |
| 13. | N-(4-(4-chlorobenzyl)-6-methoxy-3-oxo-3,4-dihydro-2H-benzo[b][1,4]oxazin-7-yl)-3,5-dimethylisoxazole-4-sulfonamide; |
| 14. | 1-((4-chlorophenyl)sulfonyl)-6-(3,5-dimethylisoxazol-4-yl)-7-methoxyquinolin-2(1H)-one; |
| 15. | 1-(4-chlorobenzoyl)-6-(3,5-dimethylisoxazol-4-yl)-7-methoxyquinolin-2(1H)-one; |
| 16. | 2-((7-(3,5-dimethylisoxazol-4-yl)-6-methoxy-2H-benzo[b][1,4]oxazin-4(3H)-yl)methyl)aniline; |
| 17. | 7-(3,5-dimethylisoxazol-4-yl)-6-methoxy-4-(pyridin-4-ylmethyl)-2H-benzo[b][1,4]oxazin-3(4H)-one; |
| 18. | 4-(4-chlorobenzyl)-7-(3,5-dimethylisoxazol-4-yl)-6-methoxy-2H-benzo[b][1,4]oxazin-3(4H)-one; |
| 19. | 7-(3,5-dimethylisoxazol-4-yl)-6-methoxy-4-(1-(pyridin-4-yl)ethyl)-2H-benzo[b][1,4]oxazin-3(4H)-one (Isomer-1); |
| 20. | 7-(3,5-dimethylisoxazol-4- yl)-6-methoxy-4-(1-(pyridin-4-yl)ethyl)-2H-benzo[b][1,4]oxazin-3(4H)-one (Isomer-2); |
| 21. | 7-(3,5-dimethylisoxazol-4-yl)-6-methoxy-4-(pyridin-3-ylmethyl)-2H-benzo[b][1,4]oxazin-3(4H)-one; |
| 22. | 7-(3,5-dimethyisoxazol-4-yl)-6-methoxy-4-(pyridin-2-ylmethyl)-2H-benzo[b][1,4]oxazin-3(4H)-one; |
| 23. | 7-(3,5-dimethyisoxazol-4-yl)-6-methoxy-4-((tetrahydro-2H-pyran-4-yl)methyl)-2H-benzo[b][1,4]oxazin-3(4H)-one; |
| 24. | 7-(3,5-dimethyisoxazol-4-yl)-6-methoxy-4-(1-(pyridin-3-yl)ethyl)-2H-benzo[b][1,4]oxazin-3(4H)-one (Isomer-1); |
| 25. | 7-(3,5-dimethyisoxazol-4-yl)-6-methoxy-4-(1-(pyridin-3-yl)ethyl)-2H-benzo[b][1,4]oxazin-3(4H)-one (Isomer-2); |
| 26. | 7-(3,5-dimethylisoxazol-4-yl)-6-methoxy-4-((6-methoxy pyridin-3-yl)methyl)-2H-benzo[b][1,4]oxazin-3(4H)-one; |
| 27. | 6-((7-(3,5-dimethylisoxazol-4-yl)-6-methoxy-3-oxo-2H-benzo[b][1,4]oxazin-4(3H)-yl)methyl)nicotinonitrile; |
| 28. | 4-((5-chloropyridin-2-yl)methyl)-7-(3,5-dimethylisoxazol-4-yl)-6-methoxy-2H-benzo[b][1,4]oxazin-3(4H)-one; |
| 29. | 7-(3,5-dimethylisoxazol-4-yl)-4-((5-fluoropyridin-2-yl)methyl)-6-methoxy-2H-benzo[b][1,4]oxazin-3(4H)-one; |
| 30. | 7-(3,5-dimethylisoxazol-4-yl)-6-methoxy-4-((5-methoxy pyridin-2-yl)methyl)-2H-benzo[b][1,4]oxazin-3(4H)-one; |
| 31. | 7-(3,5-dimethylisoxazol-4-yl)-6-methoxy-4(1-pyridin-2-yl)ethyl)-2H-benzo[b][1,4]oxazin-3(4H)-one; |
| 32. | 7-(3,5-dimethylisoxazol-4-yl)-6-methoxy-4-((6-methylpyridin-3-yl)methyl)-2H-benzo[b][1,4]oxazin-3(4H)-one; |
| 33. | 4-(1-(4-chlorophenyl)ethyl)-7-(3,5-dimethylisoxazol-4-yl)-6-methoxy-2H-benzo[b][1,4]oxazin-3(4H)-one (Isomer-1); |
| 34. | 4-(1-(4-chlorophenyl)ethyl)-7-(3,5-dimethylisoxazol-4-yl)-6-methoxy-2H-benzo[b][1,4]oxazin-3(4H)-one (Isomer-2); |
| 35. | 7-(3,5-dimethylisoxazol-4-yl)-6-methoxy-4-(2-(pyridin-2-yl)ethyl)-2H-benzo[b][1,4]oxazin-3(4H)-one; |
| 36. | 6-(3,5-dimethylisoxazol-4-yl)-7-methoxy-1-(pyridin-3-ylmethyl)quinolin-2(1H)-one; |
| 37. | 1-((5-chloropyridin-2-yl)methyl)-6-(3,5-dimethylisoxazol-4-yl)-7-methoxyquinolin-2(1H)-one; |
| 38. | 6-(3,5-dimethylisoxazol-4-yl)-7-methoxy-1-(2-morpholinoethyl)quinolin-2(1H)-one; |
| 39. | 6-(3,5-dimethylisoxazol-4-yl)-7-methoxy-1-(thiazol-2-ylmethyl)quinolin-2(1H)-one; |

-continued

| Compound. No | IUPAC Name |
|---|---|
| 40. | 6-(3,5-dimethytisoxazol-4-yl)-7-methoxy-1-(1-(pyridin-2-yl)ethyl)quinolin-2(1H)-one; |
| 41. | 6-(3,5-dimethylisoxazol-4-yl)-7-methoxy-1-(1-(pyridin-3-yl)ethyl)quinolin-2(1H)-one; |
| 42. | 6-(3,5-dimethylisoxazol-4-yl)-7-methoxy-1-(2-(pyridin-2-yl)ethyl)quinolin-2(1H)-one; |
| 43. | 6-(3,5-dimethylisoxazol-4-yl)-7-methoxy-1-(pyrimidin-2-ylmethyl)quinolin-2(1H)-one; |
| 44. | 6-(3,5-dimethylisoxazol-4-yl)-7-methoxy-1-(pyrimidin-4-ylmethyl)quinolin-2(1H)-one; |
| 45. | 6-(3,5-dimethylisoxazol-4-yl)-1-((5-fluoropyridin-2-yl)methyl)-7-methoxyquinolin-2(1H)-one; |
| 46. | 6-(3,5-dimethylisoxazol-4-yl)-7-methoxy-1-(pyridin-2-ylmethyl)quinolin-2(1H)-one; |
| 47. | 6-(3,5-dimethylisoxazol-4-yl)-7-methoxy-1-((5-(trifluoromethyl)pyridin-2-yl)methyl)quinolin-2(1H)-one; |
| 48. | 6-(3,5-dimethylisoxazol-4-yl)-7-methoxy-4,4-dimethyl-1-(pyridin-2-ylmethyl)-3,4-dihydroquinolin-2(1H)-one; |
| 49. | 7-(3,5-dimethylisoxazol-4-yl)-6-methoxy-2,2-dimethyl-4-(pyridin-3-ylmethyl)-2H-benzo[b][1,4]oxazin-3(4H)-one; |
| 50. | 6-(3,5-dimethylisoxazol-4-yl)-7-methoxy-3-methyl-1-(pyridin-2-ylmethyl)quinolin-2(1H)-one; |
| 51. | 6-(3,5-dimethylisoxazol-4-yl)-7-methoxy-3,3-dimethyl-1-(pyridin-2-ylmethyl)quinoline-2,4(1H,3H)-dione; |
| 52. | 6-(3,5-dimethylisoxazol-4-yl)-7-methoxy-3,3-dimethyl-1-(pyridin-2-ylmethyl)-3,4-dihydroquinolin-2(1H)-one; |
| 53. | 6-(3,5-dimethylisoxazol-4-yl)-7-methoxy-4-methyl-1-(pyridin-2-ylmethyl)quinolin-2(1H)-one; |
| 54. | 6-(3,5-dimethyisoxazol-4-yl)-7-methoxy-1-(pyridin-2-ylmethyl)-4-(trifluoromethyl)quinolin-2(1H)-one; |
| 55. | 4-cyclopropyl-6-(3,5-dimethytisoxazol-4-yl)-7-methoxy-1-(pyridin-2-ylmethyl)quinolin-2(1H)-one; |
| 56. | 1-(4-chlorobenzyl)-6-(3,5-dimethylisoxazol-4-yl)-7-methoxyquinolin-2(1H)-one |
| 57. | 6-(3,5-dimethylisoxazol-4-yl)-7-methoxy-1-(quinolin-2-ylmethyl)quinolin-2(1H)-one; |
| 58. | 1-((5-chloropyridin-2-yl)methyl)-6-(3,5-dimethylisoxazol-4-yl)-7-methoxy-3-methylquinolin-2(1H)-one; |
| 59. | 1-(4-chlorophenethyl)-6-(3,5-dimethylisoxazol-4-yl)-7-methoxy-3-methylquinolin-2(1H)-one; |
| 60. | 7-(3,5-dimethylisoxazol-4-yl)-6-methoxy-4-(piperidin-4-ylmethyl)-2H-benzo[b][1,4]oxazin-3(4H)-one; |
| 61. | 6-(6-hydroxypyridin-3-yl)-7-methoxy-1-(pyridin-2-ylmethyl)quinolin-2(1H)-one; |
| 62. | 6-(3-cyclopropyl-5-methylisoxazol-4-yl)-7-methoxy-1-(pyridin-2-ylmethyl)quinolin-2(1H)-one; |
| 63. | 7-methoxy-6-(5-methylisoxazol-4-yl)-1-(pyridin-2-ylmethyl)quinolin-2(1H)-one; |
| 64. | 7-methoxy-6-(3-methylisoxazol-4-yl)-1-(pyridin-2-ylmethyl)quinolin-2(1H)-one; |
| 65. | 4-(4-chlorobenzyl)-7-(3,5-dimethyl-1H-pyrazol-4-yl)-6-methoxy-2H-benzo[b][1,4]oxazin-3(4H)-one; |
| 66. | 6-(3,5-dimethyl-1H-pyrazol-4-yl)-7-methoxy-1-(pyridin-2-ylmethyl)quinolin-2(1H)-one; |
| 67. | 1-((6-chloropyridin-3-yl)methyl)-6-(3,5-dimethylisoxazol-4-yl)-7-methoxyquinolin-2(1H)-one; |
| 68. | 3-cyclohexyl-6-(3,5-dimethylisoxazol-4-yl)-7-methoxy-1-(pyridin-2-ylmethyl)quinolin-2(1H)-one; |
| 69. | 3-cyclohexyl-6-(3,5-dimethylisoxazol-4-yl)-7-methoxy-1-(pyridin-3-ylmethyl)quinolin-2(1H)-one; |
| 70. | 7-(3,5-dimethylisoxazol-4-yl)-4-((6-hydroxypyridin-3-yl)methyl-6-methoxy-2H-benzo[b][1,4]oxazin-3(4H)-one; |
| 71. | 7-(3,5-dimethylisoxazol-4-yl)-6-(2-methoxyethoxy)-4-(pyridin-4-ylmethyl)-2H-benzo[b][1,4]oxazin-3(4H)-one; |
| 72. | 6-(3,5-dimethylisoxazol-4-yl)-7-hydroxy-1-(pyridin-2-ylmethyl)quinolin-2(1H)-one; |
| 73. | 1-((5-chloropyridin-2-yl)methyl)-6-(3,5-dimethylisoxazol-4-yl)-7-hydroxyquinolin-2(1H)-one; |
| 74. | 6-(3,5-dimethylisoxazol-4-yl)-1-(pyridin-2-ylmethyl)-7-(2,2,2-trifluoroethoxy)quinolin-2(1H)-one; |
| 75. | 6-(3,5-dimethylisoxazol-4-yl)-7-(2-morpholinoethoxy)-1-(pyridin-2-ylmethyl)quinolin-2(1H)-one; |
| 76. | 7-(2-(dimethylamino)ethoxy)-6-(3,5-dimethylisoxazol-4-yl)-1-(pyridin-2-ylmethyl)quinolin-2(1H)-one; |
| 77. | 6-(3,5-dimethylisoxazol-4-yl)-7-(piperidin-4-ylmethoxy)-1-(pyridin-2-ylmethyl)quinolin-2(1H)-one; |
| 78. | 7-butoxy-6-(3,5-dimethylisoxazol-4-yl)-1-(pyridin-2-ylmethyl)quinolin-2(1H)-one; |
| 79. | 7-(allyloxy)-6-(3,5-dimethylisoxazol-4-yl)-1-(pyridin-2-ylmethyl)quinolin-2(1H)-one; |

| Compound. No | IUPAC Name |
|---|---|
| 80. | 6-(3,5-dimethylisoxazol-4-yl)-7-(2-hydroxyethoxy)-1-(pyridin-2-ylmethyl)quinolin-2(1H)-one; |
| 81. | 6-(3,5-dimethylisoxazol-4-yl)-1-(pyridin-2-ylmethyl)-7-(2-(pyrrolidin-1-yl)ethoxy)quinolin-2(1H)-one; |
| 82. | 6-(3,5-dimethylisoxazol-4-yl)-7-(2-(piperazin-1-yl)ethoxy)-1-(pyridin-2-ylmethyl)quinolin-2(1H)-one; |
| 83. | 6-(3,5-dimethylisoxazol-4-yl)-1-(pyridin-2-ylmethyl)-7-(pyridin-4-ylmethoxy)quinolin-2(1H)-one; |
| 84. | 6-(3,5-dimethylisoxazol-4-yl)-7-(3-hydroxypropoxy)-1-(pyridin-2-ylmethyl)quinolin-2(1H)-one |
| 85. | 6-(3,5-dimethylisoxazol-4-yl)-1-(pyridin-2-ylmethyl)-7-(trifluoromethoxy)quinolin-2(1H)-one; |
| 86. | 6-(3,5-dimethylisoxazol-4-yl)-7-(piperidin-4-yloxy)-1-(pyridin-2-ylmethyl)quinolin-2(1H)-one; |
| 87. | 6-(3,5-dimethylisoxazol-4-yl)-1-(pyridin-2-ylmethyl)-7-((tetrahydro-2H-pyran-4-yl)methoxy)quinolin-2(1H)-one: |
| 88. | 6-(3,5-dimethylisoxazol-4-yl)-7-(2-(piperidin-4-yl)ethoxy)-1-(pyridin-2-ylmethyl)quinolin-2(1H)-one; |
| 89. | 6-(3,5-dimethylisoxazol-4-yl)-1-(pyridin-2-ylmethyl)-7-(2-(pyrrolidin-3-yl)ethoxy)quinolin-2(1H)-one hydrochloride; |
| 90. | 7-(3,5-dimethylisoxazol-4-yl)-6-methoxy-4-((1-propionylpiperidin-4-yl)methyl)-2H-benzo[b][1,4]oxazin-3(4H)-one; |
| 91. | 7-methoxy-6-(5-methyl-2-oxo-2,3-dihydro-1H-imidazol-1-yl)-1-(pyridin-2-ylmethyl)quinolin-2(1H)-one; |
| 92. | 3-(7-methoxy-2-oxo-1-(pyridin-2-ylmethyl)-1,2-dihydroquinolin-6-yl)-4-methyl-1H-pyrrole-2,5-dione; |
| 93. | 6-(3,5-dimethylisoxazol-4-yl)-7-methoxy-1-(pyridin-2-ylmethyl)quinoxalin-2(1H)-one; |
| 94. | N-(4-(4-chlorobenzyl)-6-methoxy-3-oxo-3,4-dihydro-2H-benzo [b][1,4]oxazin-7-yl)-3,5-dimethylisoxazole-4-carboxamide; |
| 95. | 4-(4-chlorobenzyl)-7-((3,5-dimethylisoxazol-4-yl)amino)-6-methoxy-2H-benzo[b][1,4]oxazin-3(4H)-one; |
| 96. | 6-(3,5-dimethylisoxazol-4-yl)-3-(hydroxymethyl)-7-methoxy-1-(pyridin-2-ylmethyl)quinolin-2(1H)-one; |
| 97. | 6-(3,5-dimethylisoxazol-4-yl)-3-(fluoromethyl)-7-methoxy-1-(pyridin-2-ylmethyl)quinolin-2(1H)-one; |
| 98. | 6-(3,5-dimethylisoxazol-4-yl)-7-methoxy-1-((5-(1-methyl-1H-pyrazol-4-yl)pyridin-2-yl)methyl)quinolin-2(1H)-one; |
| 98a | 1-((5-bromopyridin-2-yl)methyl)-6-(3,5-dimethylisoxazol-4-yl)-7-methoxy quinolin-2(1H)-one: |
| 99. | 1-((5-(3,5-dimethyl-1H-pyrazol-4-yl)pyridin-2-yl)methyl)-6-(3,5-dimethylisoxazol-4-yl)-7-methoxyquinolin-2(1H)-one; |
| 100. | 6-(3,5-dimethylisoxazol-4-yl)-1-((5-(3-hydroxypyrrolidin-1-yl)pyridin-2-yl)methyl)-7-methoxyquinolin-2(1H)-one; |
| 101. | 6-(3,5-dimethylisoxazol-4-yl)-methoxy-1-(pyridin-2-yl methyl)-3-(2,2,2-trifluoro-1-hydroxyethyl)quinolin-2(1H)-one; |
| 102. | 6-(3,5-dimethylisoxazol-4-yl)-7-methoxy-1-(pyridin-2-yl methyl)-3-(2,2,2-trifluoro-1-hydroxyethyl)quinolin-2(1H)-one (Isomer-1); |
| 103. | 6-(3,5-dimethylisoxazol-4-yl)-7-methoxy-1-(pyridin-2-yl methyl)-3-(2,2,2-trifluoro-1-hydroxyethyl)quinolin-2(1H)-one (Isomer-2); |
| 104. | 6-(3,5-dimethylisoxazol-4-yl)-7-methoxy-1-(pyridin-2-yl methyl)-3-(2,2,2-trifluoro-1,1-dihydroxyethyl)quinolin-2(1H)-one; |
| 105. | 1-(4-chlorophenethyl)-6-(3,5-dimethylisoxazol-4-yl)-7-methoxy-3-methyl-2-oxo-1,2-dihydroquinoline-4-carbonitrile; and |
| 106. | 2-(1-(4-chlorophenethyl)-6-(3,5-dimethylisoxazol-4-yl)-7-methoxy-2-oxo-1,2-dihydroquinolin-3-yl)acetonitrile, | or a pharmaceutically acceptable salt or a pharmaceutically acceptable stereoisomer thereof.

In a further embodiment, the present invention provides processes for preparing novel bicyclic heterocyclic derivatives of formula (I).

It should be understood that the compounds of formula (I), (Ia), (Ib) and (Ic) structurally encompasses all stereoisomers, enantiomers and diastereomers, and pharmaceutically acceptable salts that may be contemplated from the chemical structure of the general formula (I) described herein.

The absolute configuration at an asymmetric atom is specified by either R or S. Resolved compounds whose absolute configuration is not known can be designated by (+) or (−) depending on the direction in which they rotate plane polarized light. When a specific stereoisomer is identified, this means that said stereoisomer is substantially free, i.e. associated with less than 50%, preferably less than 20%, more preferably less than 5%, in particularly less than 2% or 1% of the other isomers. Thus when a compound of formula (I) is for instance specified as (R), this means that the compound is substantially free of (S) isomer; when the compound of formula (I) is for instance specified as E, this means that the compound is free of the Z isomer; when the compound of formula (I) is for instance specified as cis isomer, this means that the compound is free of the trans isomer.

In yet another embodiment according to the present invention, it provides a pharmaceutical composition comprising the compound of formula (I) of the present invention and at least one pharmaceutically acceptable excipient (such as a pharmaceutically acceptable carrier or diluent). Preferably, the pharmaceutical composition comprises a therapeutically effective amount of at least one compound described herein.

In yet another embodiment of the present invention relates to the pharmaceutical combination comprising the compound of formula (I) of the present invention and at least one additional pharmaceutically acceptable therapeutic agent. Preferably, the additional pharmaceutically acceptable therapeutic agent can be anticancer agent, autoinmmune agent, cardiovascular agents and/or inflammatory agents.

Unless defined otherwise, all technical and scientific terms used herein have the same meaning as is commonly understood by one of skill in art to which the subject matter herein belongs. As used herein, the following definitions are supplied in order to facilitate the understanding of the present invention.

"Alkyl" refers to a hydrocarbon chain that may be a straight chain or branched chain, containing the indicated number of carbon atoms, for example, a $C_1$-$C_6$ alkyl group may have from 1 to 6 (inclusive) carbon atoms in it. Examples of $C_1$-$C_6$ alkyl groups include, but are not limited to, methyl, ethyl, propyl, butyl, pentyl, hexyl, isopropyl, isobutyl, sec-butyl, tert-butyl, isopentyl, neopentyl, and isohexyl.

"Alkenyl" refers to a hydrocarbon chain that may be a straight chain or branched chain, containing the indicated number of carbon atoms having at least one —C═C—, for example, a $C_2$-$C_6$ alkenyl group may have from 2 to 6 (inclusive) —C═C— atoms in it. Examples of $C_2$-$C_6$ alkenyl groups include, but are not limited to ethylene, prop-1-ene, but-1-ene, but-2-ene, pent-1-ene, pent-2-ene, hex-1-ene, hex-2-ene and the like.

"Alkoxy" refers to the group Ak-O— or —O-Ak, where Ak is an alkyl group, as defined above. Exemplary $C_1$-$C_6$ alkyl group containing alkoxy groups include but are not limited to methoxy, ethoxy, n-propoxy, 1-propoxy, isopropoxy, n-butoxy and t-butoxy.

"Alkoxyalkyl" refers to an alkyl group substituted with one or more alkoxy groups; the alkyl group and alkoxy groups are same as defined above. Representative examples of an alkoxyalkyl group include but are not limited to —CH$_2$OCH$_3$, —CH$_2$CH$_2$OCH$_3$, —CH$_2$OCH$_2$CH$_3$, —CH$_2$CH$_2$OCH$_2$CH$_3$ and the like.

"Cyanoalkyl" refers to an alkyl group, as defined above, wherein one or more of the alkyl group's hydrogen atoms have been replaced with —CN. Representative examples of an cyanoalkyl group include, but are not limited to —CH$_2$CN, —CH$_2$CH$_2$CN, —C(CH$_2$)$_2$CN, —CH$_2$CH$_2$CH$_2$CN and the like.

"Aryl" refers to an optionally substituted monocyclic, bicyclic or polycyclic aromatic hydrocarbon ring system of about 6 to 14 carbon atoms. Examples of a $C_6$-$C_{14}$aryl group include, but are not limited to phenyl, naphthyl, biphenyl, anthryl, biphenylenyl, and acenaphthyl.

"Cycloalkyl" refers to a $C_3$-$C_{10}$ non-aromatic, saturated, monocyclic, bicyclic or polycyclic hydrocarbon ring system. Representative examples of a $C_3$-$C_{10}$ cycloalkyl include, but are not limited to, cyclopropyl, cyclopentyl, cyclohexyl, cyclooctyl and the like.

"Cyano" refers to —CN group.

"Hydroxy" refers to —OH group.

"Amino" refers to an —NH$_2$ group.

"Aminoalkyl" refers to an alkyl group, as defined above, wherein one or more of the alkyl group's hydrogen atom has been replaced with amino group. Moreover one or more hydrogen atoms on the amino group can be replaced by one or more alkyl group. Representative examples of a aminoalkyl group include, but are not limited to —CH$_2$NH$_2$, —CH$_2$N(H)CH$_3$, —CH$_2$N(CH$_3$)$_2$, —(C$_2$)$_2$NH$_2$, —(CH$_2$)$_2$N(H)CH$_3$, —(CH$_2$)$_2$N(CH$_3$)$_2$ and the like.

"Hydroxyalkyl" refers to an alkyl group, as defined above, wherein one or more of the alkyl group's hydrogen atom has been replaced with —OH group. Representative examples of a hydroxylalkyl group include, but are not limited to methanol, ethanol, propanol, isopropanol, butanol, butan-2-ol and hexanol.

"Halo" or "halogen" refers to —F, —Cl, —Br and —I.

"Haloalkyl" refers to an alkyl group, as defined above, wherein one or more of the alkyl group's hydrogen atoms has been replaced with —F, —Cl, —Br or —I. Representative examples of an haloalkyl group include, but are not limited to —CH$_2$F, —CCl$_3$, —CF$_3$, —CH$_2$Cl, —CH$_2$CH$_2$Br, —CH$_2$CH$_2$I, —CH$_2$CH$_2$CH$_2$F, —CH$_2$CH$_2$CH$_2$Cl, —CH$_2$CH$_2$CH$_2$CH$_2$Br, —CH$_2$CH$_2$CH$_2$CH$_2$I, —CH$_2$CH$_2$CH$_2$CH$_2$CH$_2$Br, —CH$_2$CH$_2$CH$_2$CH$_2$CH$_2$I, —CH$_2$CH(Br)CH$_3$, —CH$_2$CH(Cl)CH$_2$CH$_3$, and —CH(F)CH$_2$CH$_3$.

The term "Heterocyclyl" includes the definitions of "heterocycloalkyl" and "heteroaryl".

The term "Heterocycloalkyl" refers to a non-aromatic, saturated, monocyclic ring system of 5 to 10 member having at least one heteroatom or heterogroup selected from O, N, S, S(O), S(O)$_2$, NH and C(O). Exemplary heterocycloalkyl groups include piperdinyl, piperazinyl, pyrrolidinyl, morpholinyl, thiomorpholinyl, 1,3-dioxolanyl, 1,4-dioxanyl,tetrahydro-2H-pyran and the like.

"Heteroaryl" refers to an unsaturated, monocyclic, bicyclic, or polycyclic aromatic ring system containing at least one heteroatom selected from oxygen, sulfur and nitrogen. Examples of $C_5$-$C_{12}$ heteroaryl groups include furan, thiophene, indole, azaindole, oxazole, thiazole, thiadiazole, isoxazole, isothiazole, imidazole, imidazol-2-one, N-methylimidazole, pyridine, pyrimidine, pyrazine, pyrrole, pyrrole-2,5-dione, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, benzoxazole, benzothiazole, benzofuran, benzisoxazole, benzimidazole, N-methylbenzimidazole, azabenzimidazole, indazole, quinazoline, quinoline and isoquinoline. Bicyclic heteroaryl groups include those where a phenyl, pyridine, pyrimidine or pyridazine ring is fused to a 5 or 6-membered monocyclic heterocyclyl ring having one or two heteroatoms atoms in the ring, one nitrogen atom together with either one oxygen or one sulfur atom in the ring, or one O or S ring atom.

"Heterocyclylalkyl" refers to an alkyl group, as defined above, wherein one or more of the alkyl group's hydrogen atom has been replaced with heterocyclyl group. Representative examples of a heterocyclylalkyl group include, but are not limited to pyrrolidinyl-1-ethyl-, morpholinyl-1-ethyl-, piperazinyl-1-ethyl-, pyridinylmethyl-, piperidinyl-methyl, or 1-propylpyrrolidine and the like.

The term "heteroatom" as used herein designates a sulfur, nitrogen, or oxygen atom.

"Monocyclic ring" or "Bicyclic ring" refers to a saturated, partially saturated or unsaturated 3-12 membered cyclic ring, in which 0 to 4 ring carbon atoms can be replaced with a heteroatom/heterogroups such as N, O, S, —C(O)—, —S(O), —NH and S(O)$_2$. Representative examples of a 3 to 12 membered ring include, but are not limited to cyclopropyl, cyclohexyl, isoxazole, triazole, imidazol-2-one, oxirane, phenyl, pyridyl, pyrazole, pyrimidine, piperdine, piperazine, thiazole, furan, pyrrolidinyl, pyrazine, pyrrole-2,5- dione, quinoline, morpholine, 1,2,3,6-tetrahydropyridine, tetrahydro-2H-pyran, 2,3-dihydrobenzo[b][1,4] dioxine, 1H-indazole and the like.

The term "comprise" or "comprising" is generally used in the sense of include, that is to say permitting the presence of one or more features or components.

The use of the term "including" as well as other forms, such as "include", "includes", and "included", is not limiting.

As used herein, the terms "treat", "treating" or "treatment" encompass either or both responsive and prophylaxis measures, e.g., measures designed to inhibit or delay the onset of the disease or disorder, achieve a full or partial reduction of the symptoms or disease state, and/or to alleviate, ameliorate, lessen, or cure the disease or disorder and/or its symptoms. The terms "treat", "treating" or "treatment", include, but are not limited to, prophylactic and/or therapeutic treatments.

As used herein the terms "subject" or "patient" are well-recognized in the art, and, are used interchangeably herein to refer to a mammal, including dog, cat, rat, mouse, monkey, cow, horse, goat, sheep, pig, camel, and, most preferably, a human. In some embodiments, the subject is a subject in need of treatment or a subject with a disease or disorder. However, in other embodiments, the subject can be a normal subject. The term does not denote a particular age or sex. Thus, adult and new-born subjects, whether male or female, are intended to be covered.

As used herein the term "therapeutically effective amount", refers to a sufficient amount of a compound or a composition being administered which will relieve to some extent one or more of the symptoms of the disease or condition being treated. The result can be reduction and/or alleviation of the signs, symptoms, or causes of a disease, or any other desired alteration of a biological system. The term "therapeutically effective amount" includes, for example, a prophylactically effective amount.

"Pharmaceutically acceptable" means that, which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salt" refers to the salts of the compounds, that is pharmaceutically acceptable and that possesses the desired pharmacological activity of the parent compound. Pharmaceutically acceptable salts of the compounds of this invention include those derived from suitable inorganic and organic acids and bases. Such salts include: acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methane sulfonic acid, ethane sulfonic acid, 1,2-ethane-disulfonic acid, 2-hydroxyethanesulfonic acid, benzene sulfonic acid. 4-chlorobenzenesulfonic acid, 2-naphthalenesulfonic acid, 4-toluenesulfonic acid, camphor sulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxyl naphthoic acid, salicylic acid, stearic acid, muconic acid, and the like.

In further yet another particular embodiment, the compounds and pharmaceutically compositions of the present invention are used in the treatment and/or prevention of diseases and/or disorders in which aberrant, abnormal or deregulated activity of bromodomain containing proteins contribute to the pathology and/or symptomology of such diseases and/or disorders. Such diseases and/or disorders mediated by one or more of these kinases are provided herein.

In further yet another particular embodiment, the compounds and pharmaceutically compositions of the present invention are useful in treatment and/or prevention of diseases and/or disorders in which aberrant, abnormal or deregulated activity of BET family of bromodomain containing proteins; in particular BRD2, BRD3, BRD4 and BRD-t proteins.

In further yet another particular embodiment, the compounds and pharmaceutically compositions of the present invention are useful in manufacture of a medicament for use in the treatment of diseases associated with bromodomain in animals including humans.

In further yet another particular embodiment, the method of treatment of diseases or disease conditions for which bromodomain inhibitor is indicated comprises administering an effective amount of compound of formula (I) according to the present invention.

In further yet another particular embodiment, the disease or disease condition for which bromodomain inhibitor is indicated is autoimmune, inflammatory or cancer.

Bromodomain inhibitors are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

Bromodomain inhibitors may be useful in the treatment of a wide variety of chronic autoimmune and inflammatory conditions such as rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing cholangitis, Addison's disease, hypophysitis, thyroiditis, type I diabetes and acute rejection of transplanted organs.

Bromodomain inhibitors may be useful in the treatment of a wide variety of acute inflammatory conditions such as acute gout, giant cell arteritis, nephritis including lupus nephritis, vasculitis with organ involvement such as glomerulonephritis, vasculitis including giant cell arteritis, Wegener's granulomatosis, Polyarteritisnodosa, Behcet's disease, Kawasaki disease, Takayasu's Arteritis, vasculitis with organ involvement and acute rejection of transplanted organs.

Bromodomain inhibitors may be useful in the prevention or treatment of diseases or conditions which involve inflammatory responses to infections with bacteria, viruses, fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus.

Bromodomain inhibitors may be useful in the prevention or treatment of conditions associated with ischaemia-reperfusion injury such as myocardial infarction, cerebro-vascular ischaemia (stroke), acute coronary syndromes, renal reperfusion injury, organ transplantation, coronary artery bypass grafting, cardio-pulmonary bypass procedures, pulmonary, renal, hepatic, gastro-intestinal or peripheral limb embolism.

Bromodomain inhibitors may be useful in the treatment of disorders of lipid metabolism via the regulation of APO-A1 such as hypercholesterolemia, atherosclerosis and Alzheimer's disease.

Bromodomain inhibitors may be useful in the treatment of fibrotic conditions such as idiopathic pulmonary fibrosis, renal fibrosis, post-operative stricture, keloid formation, scleroderma and cardiac fibrosis.

Bromodomain inhibitors may be useful in the prevention and treatment of viral infections such as herpes virus, human papilloma virus, adenovirus and poxyirus and other DNA viruses.

Bromodomain inhibitors may be useful in the treatment of cancer, including hematological, epithelial including lung, breast and colon carcinomas, midline carcinomas, mesenchymal, hepatic, renal and neurological tumors.

In one embodiment the disease or condition for which a bromodomain inhibitor is indicated is selected from diseases associated with systemic inflammatory response syndrome, such as sepsis, burns, pancreatitis, major trauma, haemorrhage and ischaemia. In this embodiment the bromodomain inhibitor would be administered at the point of diagnosis to reduce the incidence of: SIRS, the onset of shock, multi-organ dysfunction syndrome, which includes the onset of acute lung injury, ARDS, acute renal, hepatic, cardiac and gastro-intestinal injury and mortality.

In another embodiment the bromodomain inhibitor would be administered prior to surgical or other procedures associated with a high risk of sepsis, haemorrhage, extensive tissue damage, SIRS or MODS (multiple organ dysfunction syndrome).

In a particular embodiment the disease or condition for which a bromodomain inhibitor is indicated is sepsis, sepsis syndrome, septic shock and endotoxaemia. In another embodiment, the bromodomain inhibitor is indicated for the treatment of acute or chronic pancreatitis. In another embodiment the bromodomain is indicated for the treatment of burns. In one embodiment the disease or condition for which a bromodomain inhibitor is indicated is selected from herpes simplex infections and reactivations, cold sores, herpes zoster infections and reactivations, chickenpox, shingles, human papilloma virus, cervical neoplasia, adenovirus infections, including acute respiratory disease, poxyirus infections such as cowpox and smallpox and African swine fever virus. In one particular embodiment a bromodomain inhibitor is indicated for the treatment of Human papilloma virus infections of skin or cervical epithelia.

The term "diseases or conditions for which a bromodomain inhibitor is indicated", is intended to include each of or all of the above disease states.

While it is possible that for use in therapy, a compound of formula (I) as well as pharmaceutically acceptable salts thereof may be administered as the raw chemical, it is common to present the active ingredient as a pharmaceutical composition.

The term "therapeutically effective amount" means the amount of the subject compound that will elicit the biological or medical response of a tissue, system, animal or human that is being sought by the researcher, veterinarian, medical doctor or other clinician.

The compounds and pharmaceutically compositions of the present invention may be used in combination with other drugs that are used in the treatment/prevention/suppression or amelioration of the diseases or conditions for which compounds of the present invention may be useful. Such other drugs may be administered, by a route and in an amount commonly used there for, contemporaneously or sequentially with a compound of the present invention. When a compound of the present invention is used contemporaneously with one or more other drugs, a pharmaceutical composition containing such other drugs in addition to the compound of the present invention may also be preferred. Accordingly, the pharmaceutical compositions of the present invention include those that also contain one or more other active ingredients, in addition to a compound of the present invention.

A pharmaceutical composition of the invention may be formulated as being compatible with its intended route of administration, which may preferably be an oral administration. For example the pharmaceutical compositions of the invention may be formulated for administration by inhalation, such as aerosols or dry powders; for oral administration, such in the form of tablets, capsules, gels, syrups, suspensions, emulsions, elixirs, solutions, powders or granules; for rectal or vaginal administration, such as suppositories: or for parenteral injection (including intravenous, subcutaneous, intramuscular, intravascular, or infusion) such as a sterile solution, suspension or emulsion.

The compounds of the present invention may also be entrapped in microcapsules prepared, for example, by coacervation techniques or by interfacial polymerization, for example, hydroxymethyl cellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The bicyclic heterocyclic derivatives of formula (I) according to the present invention may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimization procedures. The specifics of the processes according to the present invention are detailed in the example section mentioned below.

In a further aspect, the compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms of the compound are replaced by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include isotopes of hydrogen, carbon, nitrogen, oxygen, phosphorous, sulfur, fluorine, chlorine and iodine, such as $^2$H ("D"), $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Isotopically labeled compounds of the present inventions can generally be prepared by following procedures analogous to those disclosed in the Schemes and/or in the Examples herein below, by substituting an isotopically labeled reagent for a non-isotopically labeled reagent.

The abbreviations used in the entire specification may be summarized herein below with their particular meaning.

MeOH—Methanol; EtOH—Ethanol; DME—1,2-dimethoxyethane; CHCh$_3$-Chloroform: DCM—Dichloromethane: DMF—N,N-Dimethylformamide: DMSO—Dimethylsulfoxide: CDCl$_3$—Deuterated chloroform; EtOAc—Ethylacetate: CH$_3$CN—Acetonitrile; THF—ITetrahydrofuran; TEA—Triethylamine; DIPEA—Diisopropylethylamine; TFA—Trifluoroacetic acid: AcOH—Acetic acid; AlCl$_3$—Aluminium chloride: AlBr$_3$—Aluminium bromide; Br$_2$—Bromine; NBS—N-bromosuccinimide; NCS—N-chlorosuccinimide; MeI—Methyl iodide: KI—Potassium iodide: TPP—Triphenyl phosphene; NaOAc—Sodiumacetate; KOAc—Potassiumacetate: Na$_2$SO$_4$—Sodium sulphate; H$_2$SO$_4$—Sulfuric acid; HNO$_3$—Nitric acid; HBr—Hydrobromic acid; NaHCO$_3$—Sodium bicarbonate; KHCO$_3$—Potassium bicarbonate; Na$_2$CO$_3$—Sodium carbonate; K$_2$CO$_3$—Potassium carbonate; Cs$_2$CO$_3$—Cesiumcarbonate; NaH—Sodium hydride; t—BuOK—Potassium tert—hutoxide; LDA—lithium diisopropylamide; n-BuLi—n-—Butyllithium; DIAD—Diisopropylazodicarboxylate; BBr$_3$—Boron tribromide; NMP—N-Methyl pyrrolidine; DAST—Diethylaminosulfurtrifluoride; AgBF$_4$—Silver tetrafluoroborate; NaN$_3$—Sodium azide; CuI—Copper(I)iodide; SnCl$_2$.2H$_2$O—Stannous chloride dihydrate; NaBH$_4$—Sodium borohydride; NaCNBH$_3$—Sodium cyanoborohydride; (BOC)$_2$O—Di-tert-butyldicarbonate; EDC.HCl—1-Ethyl-3-(3-dimethylaminopropyl)carbodiimide hydrochloride; HOBt-1-hydroxybenzotriazole; POCl$_3$—Phosphorous oxychloride; SOCl$_2$—Thionyl chloride; AcCl—Acetyl chloride; Ac$_2$O—Acetic anhydride; NH$_4$Cl—Ammonium chloride; NiCl$_2$—Nickel chloride; H$_2$O$_2$—Hydrogen peroxide; NaOEt—Sodium ethoxide: NaOMe—Sodium methoxide: NaOH—Sodium hydroxide; KOH—potassium hydroxide; HCl—Hydrochloric acid; Pd(pph$_3$)$_4$—Tetrakis (triphenylphosphine)palladium(0); Pd(dppf)Cl$_2$—[1,1'-Bis(diphenyl phosphino)ferrocene]dichloropalladium (II), complex with dichloromethane; Pd(OAc)$_2$—Palladium(II)acetate; BINAP—2,2'-Bis(diphenylphosphino)-1,1'-binaphthalene; TMS—CF$_3$-(Trifluoromethyl)trimethylsilane; TBAF—Tetrabutylammonium fluoride; KCN—Potassium cyanide; Pd/C—Palladium on activated carbon; H$_2$O—Water: Fe—Iron powder; ML—Milliliter; TLC—Thin layer chromatography; RT—Room temperature; h—Hour; N—Normality; M—Molarity; s—Singlet; d—Doublet; t—Triplet; m—Multiplet; $^1$HNMR—Proton nuclear magnetic resonance; MS—Mass spectroscopy; LC—Liquid chromatography; H—Proton; MHz—Mega hertz; Hz—Hertz; ppm—Parts per million; Bs—Broad singlet; ES—Electm spray; Conc—Concentrated; g—Gram and Mmol—Milli mol.

General Scheme:

In one aspect of the present invention relates to the preparation of bicyclic heterocyclic derivatives of formula (I). Herein disclosed the general process for preparation of the compound of formula (I).

Scheme-I:

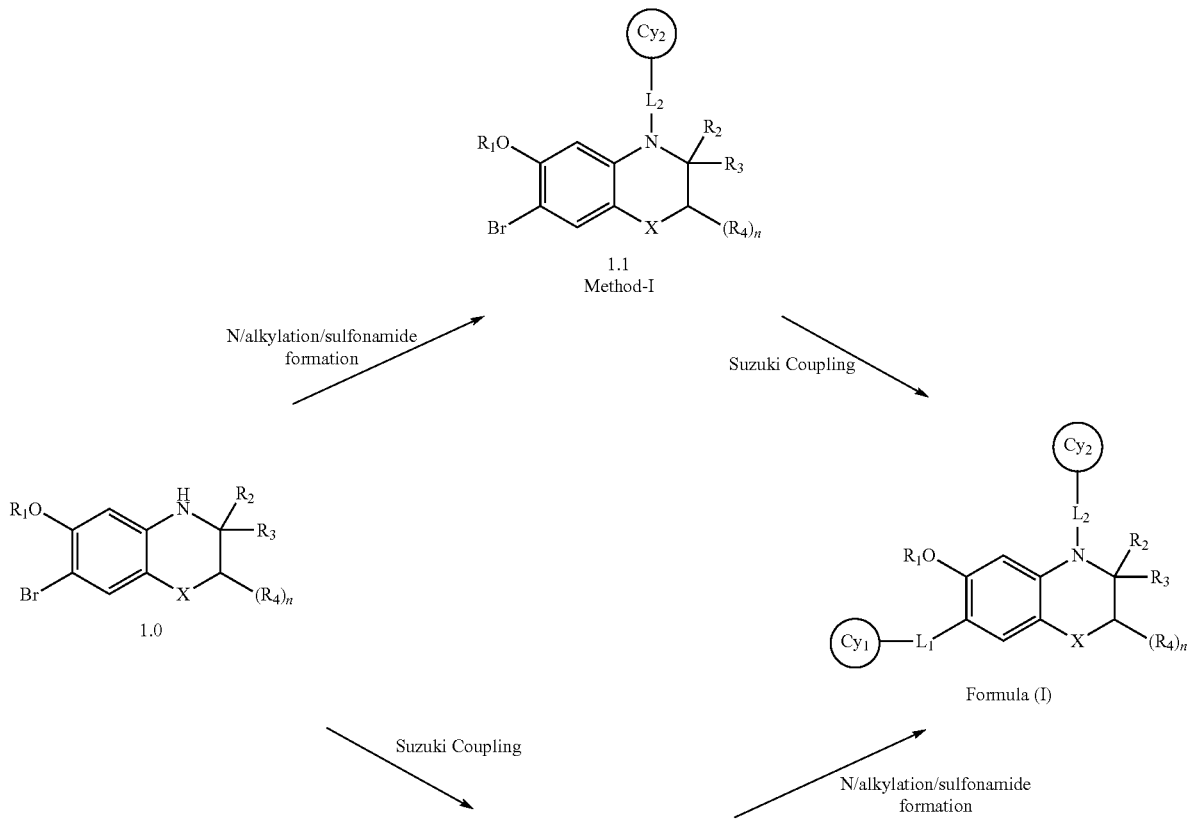

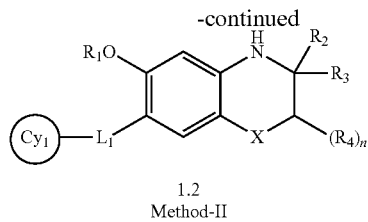

1.2
Method-II

In Scheme-I, the compounds of formula-I are prepared in two methods:

Method-I: N-alkylation/sulfonamide formation followed by Suzuki coupling.

Method-II: Suzuki coupling followed by N-alkylation/sulfonamide formation.

N-Alkylation/Sulfonamide Formation:

The compound of formula-1.0 and 1.2 can undergo N-alkylation/sulfonylation with sulfonyl chloride/sulfonates/alkylhalide derivatives in presence of a suitable solvent (e.g., ACN, DMF, DCM, THF, Dioxane, and the like) and a suitable base (e.g., $Cs_2CO_3$, t-BuOK, $K_2CO_3$, $Na_2CO_3$, Pyridine, and the like) at a temperature of about 0° C. to 50° C. for about 2-48 h to provide compound of formula-1.1 and compound of formula (I) respectively.

Suzuki Coupling:

A compound of formula (I) and a compound of formula-1.2 can be prepared by reacting a compound of formula-1.1 and a compound of formula-1.0 with $Cy_1$-boronic acid/ester respectively in presence of a suitable solvent (e.g., DME/$H_2O$, 1,4-Dioxane/$H_2O$, DMF, DMSO, and the like), a suitable base (e.g., $Na_2CO_3$, $K_2CO_3$, KOAc, and the like) and a suitable Pd catalyst (e.g., $Pd(OAc)_2$, $Pd(PPh_3)_2Cl_2$, $Pd(PPh_3)_4$, $Pd(dppf)_2Cl_2$, and the like) at a temperature of about 60° C. to 150° C. for about 2 to 24 h.

Scheme-II:

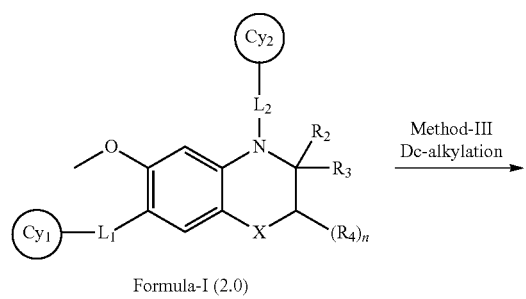

Formula-I (2.0)

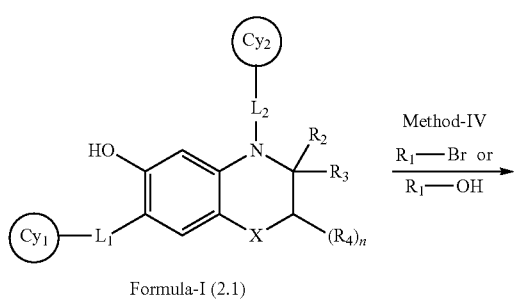

Formula-I (2.1)

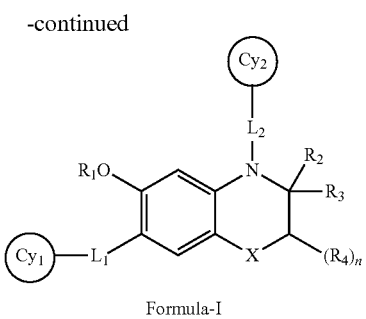

Formula-I

Method-III: (De-alkylation):

The compound of formula-I (2.0) can be treated with strong acid (e.g., $BBr_3$, HCl, HBr, and the like) in presence of a suitable solvent (e.g., DCM, $CHCl_3$, DCE or 1,4-Dioxane, and the like) at a temperature of about −78° C. to 35° C. for about 2 to 24 h to provide the compound of formula-I (2.1).

Method-IV: This method can be carried out in any of the alternative procedures given below.

O-alkylation: The compound of formula-I (2.1) can undergo O-alkylation with $R_1$—Br in presences of a suitable solvent (e.g., DMF, ACN, THF, Dioxane, and the like) and a suitable base (e.g., NaH, $Cs_2CO_3$, t-BuOK, $K_2CO_3$, $Na_2CO_3$, Pyridine, and the like) at a temperature of about 20° C. to 120° C. for about 2 to 48 h to provide the compound of formula (I).

Mitsunobu or Mitsunobu-type Reaction: The compound of formula-I (2.1) can be treated with $R_1$—OH in presence of triphenylphosphine, and suitable reagent like DIAD or DEAD in a suitable solvent (e.g., Diethyl ether, THF, and the like) at a temperature of about 0° C. to 35° C. for about 8 to 24 h to provide the compound of formula (I).

EXAMPLES

Although the invention has been illustrated by certain of the preceding examples, it is not to be construed as being limited thereby, but rather, the invention encompasses the generic area as hereinbefore disclosed. Various modifications and embodiments can be made without departing from the spirit and scope thereof.

The MS data provided in the examples described below were obtained as follows:

Mass spectrum: LC/MS Agilent 6120 Quadrapole LC/MS.

The NMR data provided in the examples described below were obtained as follows:

$^1$H-NMR: Varian 400 MHz.

The microwave chemistry was performed on a CEM Explorer.

The procedure for the compounds of Formula (I) are detailed herein below stepwise including the general Synthesis of various intermediates involved in process of manufacture of the compounds according to the present invention.

Intermediate-1: Synthesis of 7-(3,5-dimethylisoxazol-4-yl)-6-methoxy-3,4-dihydro-2H-benzo[b][1,4]oxazine

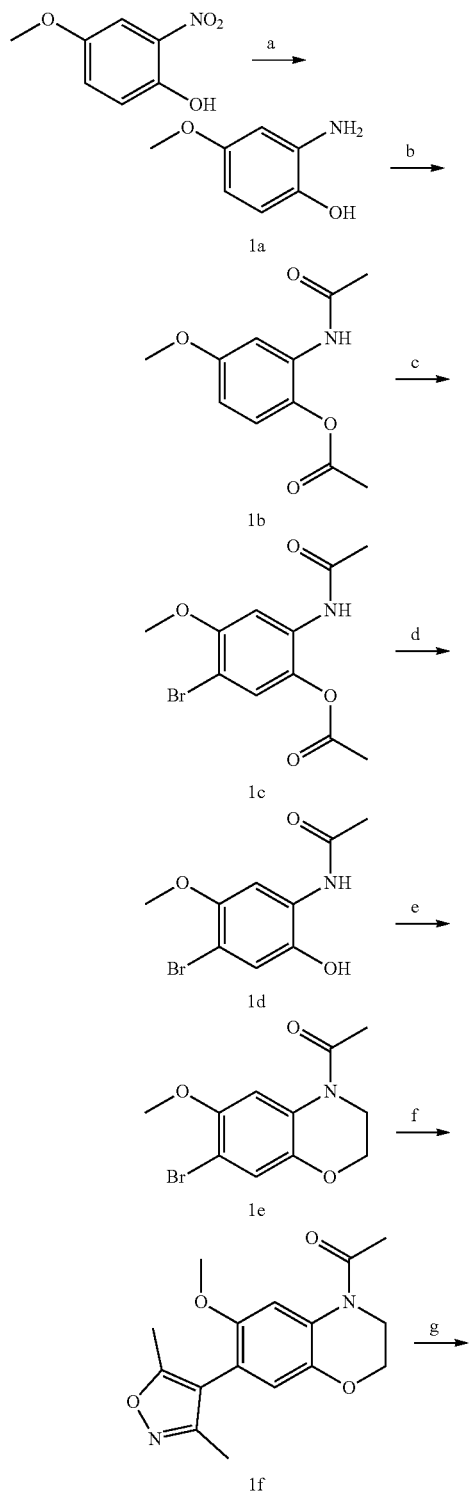

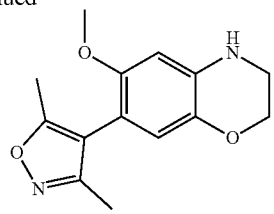

Intermediate-1

Step-a: Synthesis of 2-amino-4-methoxyphenol

To a solution of 4-methoxy-2-nitrophenol (5.0 g, 29.58 mmol) in MeOH (50 mL) was added 10% Pd—C (2.5 g) and stirred under $H_2$ balloon pressure at RT for 16 h. After completion of the reaction, the reaction mixture was filtered through celite bed, washed with methanol. The filtrate was concentrated to afford the title product as an off white solid (4.0 g, 97%). The crude product was as such taken forward for next step without further purification. $^1$H NMR (400 MHz, $CDCl_3$): δ 6.75-6.60 (m, 1H), 6.40-6.28 (m, 1H), 6.25-6.15 (m, 1H), 3.75-3.60 (bs, 3H); LC-MS: m/z 140.1 $(M+1)^+$.

Step-b: Synthesis of 2-acetamido-4-methoxyphenylacetate

To an ice-cooled solution of 2-amino-4-methoxyphenol (5 g, 35.97 mmol) in THF (130 mL) was added triethylamine (25 mL, 179.85 mmol) and stirred for 10 min before acetyl chloride (7.7 mL. 107.91 mmol) was added. Then the reaction mixture allowed to stir at RT for 16 h. After completion of the reaction, the reaction mixture was quenched with $NaHCO_3$ solution (up to pH ~8) and extracted with EtOAc (200 mL×2). The combined organic layers were washed with water (200 mL), brine (100 mL), dried over sodium sulphate and concentrated to get residue. The residue was directly used for next step without further purification (5.0 g, 62%).
$^1$H NMR (400 MHz, $CDCl_3$): δ 7.90-7.75 (bs, 1H), 7.25-7.10 (m, 1H), 7.05-6.95 (m, 1H), 6.70-6.60 (m, 1H), 3.79 (s, 3H), 2.34 (s, 3H), 2.17 (s, 3H); LC-MS: m/z 224.1 $(M+1)^+$.

Step-c: Synthesis of 2-acetamido-5-bromo-4-methoxyphenylacetate

To an ice cooled solution of 2-acetamido-4-methoxyphenyl acetate (5.0 g, 22.42 mmol) in DMF (65 mL) was add N-bromosuccinimide (4.79 g, 26.90 mmol) portion wise and stirred at RT for 16 h. After completion of the reaction, the reaction mixture was poured over crushed ice, separated solids were filtered, washed with water and dried under reduced pressure. The residue was directly used for next step without further purification (4.0 g, 59%). $^1$H NMR (400 MHz, $CDCl_3$): δ 7.99 (s, 1H), 7.33 (s, 1H), 7.20-7.10 (bs, 1H), 3.89 (s, 3H), 2.36 (s, 3H), 2.19 (s, 3H); LC-MS: m/z 302.0 $(M+1)^+$.

Step-d: Synthesis N-(4-bromo-2-hydroxy-5-methoxyphenyl)acetamide

To a solution of 2-acetamido-5-bromo-4-methoxyphenyl acetate (1.0 g, 3.29 mmol) in MeOH (10 mL) was add potassium carbonate (1.36 g, 9.86 mmol) portion wise and stirred at RT for 16 h. After completion of the reaction, the reaction mixture was poured over crushed ice, separated solids were filtered, washed with water and dried under vacuum. The residue was directly used for the next step without further purification (0.7 g, 81%). $^1$H NMR (400 MHz, DMSO-$d_6$): δ 9.70 (s, 1H), 9.31 (s, 1H), 7.69 (s, 1H), 7.02 (s, 1H), 3.71 (s, 3H), 2.09 (s, 3H); LC-MS: m/z 262.0 (M+1)$^+$.

Step-e: Synthesis 1-(7-bromo-6-methoxy-2H-benzo[b][1,4]oxazin-4(3H)-yl)ethanone

To a solution of N-(4-bromo-2-hydroxy-5-methoxyphenyl)acetamide (0.60 g, 2.30 mmol) in DCM (7.5 mL) and CH$_3$CN (4.5 mL) were added 1,2-dibromoethane (0.8 mL, 9.23), NaOH (037 g, 9.23 mmol), benzyltriethylammonium chloride (0.12 g) and stirred at RT for 16 h. After completion of the reaction, the reaction mixture was diluted with water (80 mL) and extracted with EtOAc (200 mL). The organic layer was washed with water (200 mL), brine (100 mL), dried over sodium sulphate and concentrated to afford the title compound as an off white solid (0.5 g, 75%). $^1$H NMR (400 MHz, DMSO-$d_6$): δ 8.05-7.80 (bs, 1H), 7.12 (s, 1H), 4.21 (t, J=4.4 Hz, 2H), 3.83 (t, J=4.6 Hz, 2H), 3.74 (s, 3H), 2.27 (s, 3H); LC-MS: m/z 288.0 (M+1)$^+$.

Step-f: Synthesis 1-(7-(3,5-dimethylisoxazol-4-yl)-6-methoxy-2H-benzo[b][1,4]oxazin-4(3H)-yl)ethanone To a solution of 1-(7-bromo-6-methoxy-2H-benzo[b][1,4]oxazin-4(3H)-yl)ethanone (0.45 g, 1.57 mmol) in 1,2-DME (4.5 mL) and H$_2$O (1.5 mL) were added 3,5-dimethylisoxazole boronic acid (0.66 g, 4.72 mmol), sodium carbonate (0.42 g, 3.93 mmol) and degassed with nitrogen purging for 20 min. Then tetrakistriphenylphosphinepalladium(0) (0.09 g, 0.078 mmol) was added and heated at 100° C. for 16 h. After completion of the reaction, the reaction mixture was diluted with EtOAc (50 mL), washed with water (50 mL), brine (50 mL), dried over sodium sulphate and concentrated to get residue. The obtained residue was directly used for next step, without further purification (0.3 g, 66%). $^1$H NMR (400 MHz, DMSO-$d_6$): δ 8.00-7.80 (bs, 1H), 6.76 (s, 1H), 4.23 (t, J=4.4 Hz, 2H), 3.87 (t, J=4.6 Hz, 2H), 3.68 (s, 3H), 2.30 (s, 3H), 2.25 (s, 3H), 2.07 (s, 3H); LC-MS: m/z 303.1 (M+1)$^+$.

Step-g: Synthesis 7-(3,5-dimethylisoxazol-4-yl)-6-methoxy-3,4-dihydro-2H-benzo[b][1,4]oxazine To a solution of 1-(7-(3,5-dimethylisoxazol-4-yl)-6-methoxy-2H-benzo[b][1,4]oxazin-4(3H)-yl)ethanone (0.3 g, 0.99 mmol) in MeOH (3 mL) and H$_2$O (1 mL) was added KOH (0.35 g, 6.35 mmol) and stirred at RT for 2 h. Reaction mixture was diluted with EtOAc (50 mL), washed with water (50 mL), brine (50 mL), dried over sodium sulphate and concentrated. The obtained residue was directly used for next step, without further purification (0.2 g, 77%): LC-MS: m/z 261.1 (M+1)$^+$.

Intermediate-2: Synthesis of 7-bromo-6-methoxy-2H-benzo[b][1,4]oxazin-3(4H)-one

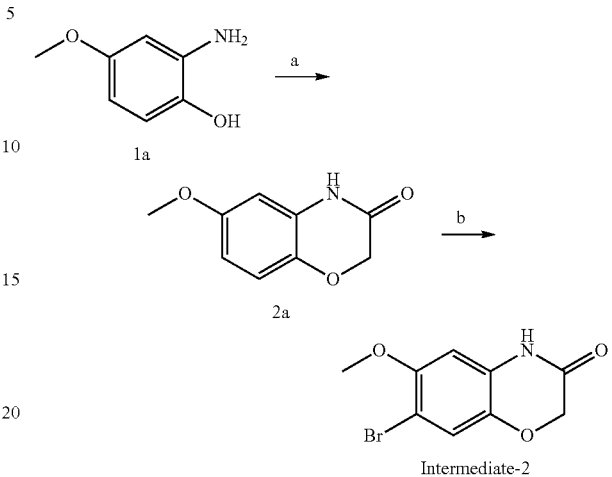

Step-a: Synthesis of 6-methoxy-2H-benzo[b][1,4]oxazin-3(4H)-one

To an ice-cooled solution of 2-amino-4-methoxyphenol (4 g, 28.77 mmol) in CH$_3$CN (50 mL) was added K$_2$CO$_3$ (12.0 g, 86.33 mmol) and stirred for 10 min before 2-chloroacetyl chloride (3.43 g, 57.55 mmol) was added. Then the reaction mixture was allowed stirred at 100° C. for 2 h. After completion of the reaction, the reaction was concentrated and treated with ice-cold water to crash out the solids. The separated solids were filtered, washed with water and dried under vacuum (4.1 g, 78%). $^1$H NMR (400 MHz, DMSO-$d_6$): δ 10.61 (bs, 1H), 6.87-6.85 (m, 1H), 6.50-6.47 (m, 2H), 4.48 (s, 2H), 3.68 (s, 3H); LC-MS: m/z 178.2 (M−1)$^+$.

Step-b: Synthesis of 7-bromo-6-methoxy-2H-benzo[b][1,4]oxazin-3(4H)-one

To an ice cooled solution of 6-methoxy-2H-benzo[b][1,4]oxazin-3(4H)-one (4.0 g, 22.9 mmol) in DMF (50 mL) was add N-bromosuccinimide (10.17 g, 58.0 mmol) portion wise and stirred at RT for 3 h. After completion of the reaction, the reaction mixture was poured over ice water, separated solids were filtered, washed with water and dried under vacuum (4.0 g, 70%). $^1$H NMR (400 MHz, DMSO-$d_6$): δ 10.72 (bs, 1H), 7.19 (s, 1H), 6.62 (s, 1H), 4.53 (s, 2H), 3.76 (s, 3H); LC-MS: m/z 257.0 (M−1)$^+$.

Intermediate-3: Synthesis of 7-bromo-6-methoxy-2,2-dimethyl-2H-benzo[b][1,4]oxazin-3(4H)-one

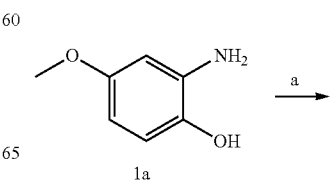

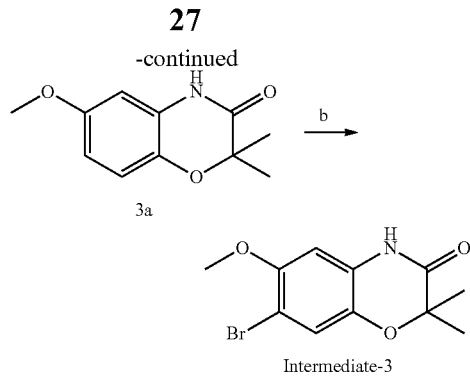

The process for preparation is similar to the one depicted in intermediate-2. The desired compound obtained as a white solid (0.09 g, 60%). $^1$H NMR (400 MHz, DMSO-d$_6$): δ 10.64 (bs, 1H), 7.15 (s, 1H), 6.61 (s, 1H), 3.76 (s, 3H), 1.37 (s, 6H).

Intermediate-4: Synthesis of 7-amino-4-(4-chlorobenzyl)-6-methoxy-2H-benzo[b][1,4]oxazin-3(4H)-one

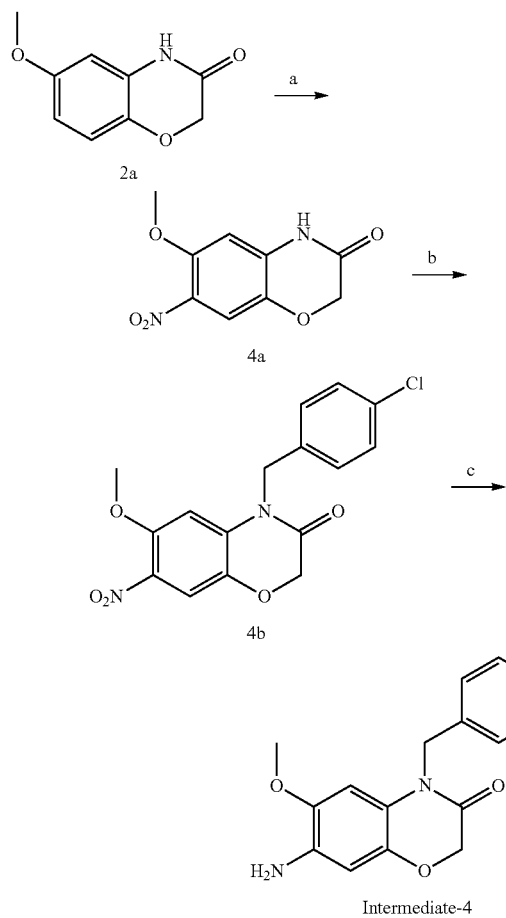

Step-a: Synthesis of 6-methoxy-7-nitro-2H-benzo[b][1,4]oxazin-3(4H)-one

To an ice cooled solution of 6-methoxy-2H-benzo[b][1,4]oxazin-3(4H)-one (0.60 g, 3.35 mmol) in AcOH (1.8 mL) was added drop wise 70% HNO$_3$ (0.6 mL) and stirred at RT for 15 min. After completion of the reaction, the reaction mixture was poured into ice water (100 g), separated solids were filtered, washed with water and dried under reduced pressure. The residue was directly used for the next step without further purification (0.60 g, 80%). $^1$H NMR (400 MHz, DMSO-d$_6$) δ 11.14 (bs, 1H), 7.60 (s, 1H), 6.75 (s, 1H), 4.64 (s, 2H), 3.85 (s, 3H). LC-MS: m/z 223.1 (M−1)$^+$.

Step-b: Synthesis of 4-(4-chlorobenzyl)-6-methoxy-7-nitro-2H-benzo[b][1,4]oxazin-3(4H)-one To an solution of 6-methoxy-7-nitro-2H-benzo[b][1,4] oxazin-3(4H)-one (0.60 g, 2.67 mmol) in DMF (6 mL) were added K$_2$CO$_3$ (1.06 g, 7.68 mmol), followed by addition of 4-chloro benzyl bromide (0.41 g, 2.00 mmol), and stirred at 80° C. for 16 h. After completion of the reaction, the reaction mixture was poured into ice water (100 g), separated solids were filtered, washed the solid thoroughly with water and dried under reduced pressure. The residue was directly used for the next step without further purification (0.48 g, 51%). $^1$H NMR (400 MHz, DMSO-d$_6$) δ 7.63 (s, 1H), 7.43-7.37 (m, 4H), 6.89 (s, 1H), 5.29 (s, 2H), 4.86 (s, 2H), 3.78 (s, 3H).

Step-c: Synthesis of 7-amino-4-(4-chlorobenzyl)-6-methoxy-2H-benzo[b][1,4]oxazin-3(4H)-one To a solution of 4-(4-chlorobenzyl)-6-methoxy-7-nitro-2H-benzo[b][1,4]oxazin-3(4H)-one (0.48 g, 1.38 mmol) in EtOH (5 mL) and water (2.5 mL) at RT were added NH$_4$Cl (0.22 g, 4.14 mmol) followed by Fe powder (0.39 g, 7.00 mmol) and refluxed at 100° C. for 2 h. Then the reaction mixture was cooled to RT, filtered through celite pad and washed with EtOAc (200 mL). The organic layer was washed with aq. sodium bicarbonate solution (50 mL), water (50 mL), brine (50 mL), dried over sodium sulphate and concentrated. The residue was purified by column chromatography on silica gel (100-200 mesh) to afford the title compound (0.20 g. 46%); $^1$H NMR (400 MHz, DMSO-d$_6$) δ 7.39 (d, J=8.3 Hz, 2H), 7.31 (d, J=8.3 Hz, 2H), 6.54 (s, 1H), 6.31 (s, 1H), 5.10 (s, 2H), 4.66 (s, 2H), 4.58 (s, 2H), 3.60 (s, 3H); LC-MS: m/z 319.1 (M+1)$^+$. Intermediate-5: Synthesis of 6-bromo-7-methoxyquinolin-2(1H)-one

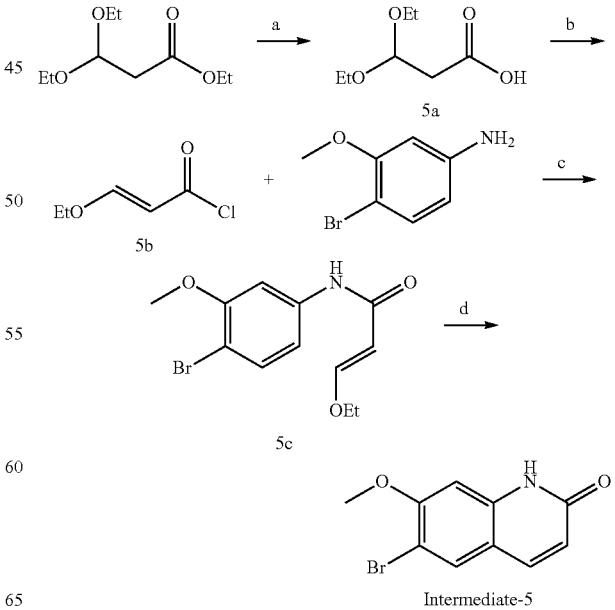

Step-a: Synthesis of 3,3-diethoxypropanoic acid

To a stirred suspension of ethyl 3,3-diethoxypropanoate (15.0 g, 78.88 mmol) in water (32 mL) was added NaOH (4.10 g, 102.6 mmol) and heated to 110° C. for 1.5 h. After completion of the reaction, the reaction mixture was cooled, acidified to pH~3 with aq. 3N HCl and extracted with EtOAc (500 mL×2). The organic layer was washed with water (200 mL), brine (100 mL), dried over sodium sulphate and concentrated. The residue was used for next step without further purification (11.50 g, 91%). $^1$H NMR (400 MHz, DMSO-$d_6$): δ 12.20 (s, 1H), 4.81 (t, J=5.9 Hz, 1H), 3.58-3.59 (m, 2H), 3.48-3.40 (m, 2H), 2.60-2.40 (m, 2H), 1.09 (t, J=7.3 Hz, 6H).

Step-b: Synthesis of 3-ethoxyacryloyl chloride

To an ice cooled compound of 3,3-diethoxypropanoic acid (5.00 g, 31.05 mmol) was added thionyl chloride (10.0 mL, 142.9 mmol) over a period of 10 min., and stirred at 80° C. for 1.5 h. After completion of the reaction, the reaction mixture was concentrated and dried under reduced pressure to afford the title product as a dark brown liquid (3.0 g, 73%). $^1$H NMR (400 MHz, DMSO-$d_6$): δ 7.50 (d, J=12.2 Hz, 1H), 5.14 (d, J=12.2 Hz, 1H), 3.94 (q, J=7.3 Hz, 2H), 1.24 (t, J=7.3 Hz, 3H).

Step-c: Synthesis of (E/Z)—N-(4-bromo-3-methoxyphenyl)-3-ethoxyacrylamide

To an ice cooled solution of 4-bromo-3-methoxyaniline (3.00 g, 14.85 mmol) in pyridine (20 mL) was added (E/Z)-3-ethoxyacryloyl chloride (2.98 g, 22.27 mmol) over a period of 5 min. and stirred at RT for 16 h. After completion of the reaction, the reaction mixture was diluted with ice cooled water and extracted with EtOAC (150 mL×2). The combined organic layer was washed with aq. 1N HCl (100 mL), water (150 mL), brine (100 mL), dried over sodium sulphate and concentrated. The residue was used for next step without further purification (3.20 g, 72%). $^1$H NMR (400 MHz, DMSO-$d_6$): δ 9.86 (s, 1H), 7.54-7.42 (m, 3H), 7.12-7.08 (m, 1H), 5.50 (d, J=-12.7 Hz, 1H), 3.95 (q, J=6.9 Hz, 2H), 3.80 (s, 3H), 1.27 (t, J=7.3 Hz, 3H); LC-MS: m/z 301.1 (M+1)$^+$.

Step-d: Synthesis of 6-bromo-7-methoxyquinolin-2(1H)-one

A solution of (E/Z)—N-(4-bromo-3-methoxyphenyl)-3-ethoxyacrylamide (3.0 g, 10.0 mmol) in Conc. $H_2SO_4$ (30 mL) was stirred at RT for 1 h. After completion of the reaction, the reaction mixture was poured over ice water, separated solids were filtered, washed the solid thoroughly with water and dried under reduced pressure. The residue was directly used for the next step without further purification (2.08 g, 82%). $^1$H NMR (400 MHz, DMSO-$d_6$): δ 12.70 (bs, 1H), 7.94 (s, 1H), 7.80 (d, J=9.8 Hz, 1H), 6.92 (s, 1H), 6.36 (d, J=9.8 Hz, 1H), 3.88 (s, 3H); LC-MS: m/z 256.0 (M+1)$^+$.

Intermediate-6: Synthesis of 6-(3,5-dimethylisoxazol-4-yl)-7-methoxyquinolin-2(1H)-one

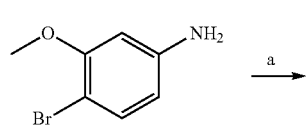

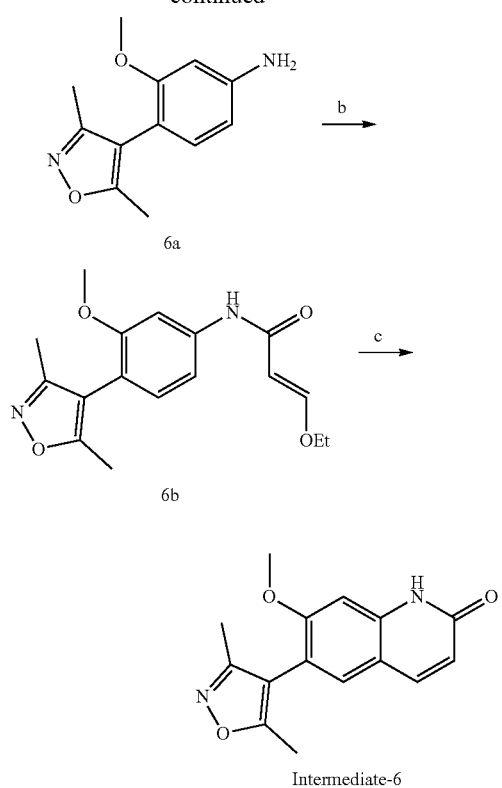

Step-a: Synthesis of 4-(3,5-dimethylisoxazol-4-yl)-3-methoxyaniline

The process of this step was adopted from step-f of intermediate-1. The desired compound obtained as a pale yellow solid (0.6 g, 60%). $^1$H NMR (400 MHz, DMSO-$d_6$): δ 6.78 (d, J=7.8 Hz, 1H), 6.30-6.19 (m, 2H), 5.26 (s, 2H), 3.66 (s, 3H), 2.19 (s, 3H), 2.02 (s, 3H); LC-MS: m/z 219.2 (M+1)$^+$.

Step-b: Synthesis of (E)-N-(4-(3,5-dimethylisoxazol-4-yl)-3-methoxyphenyl)-3-ethoxyacryl amide The process of this step was adopted from step-c of intermediate-5. The desired compound obtained as a pale yellow solid (0.4 g, 46%). $^1$H NMR (400 MHz, DMSO-$d_6$): δ 9.85 (s, 1H), 7.52-7.48 (m, 2H), 7.22-7.21 (m, 1H), 7.11-7.09 (m, 1H), 5.53 (d, J=12.2 Hz, 2H), 3.98-3.93 (m, 2H), 3.73 (s, 3H), 2.23 (s, 3H), 2.05 (s, 3H), 1.30-1.22 (m, 2H); LC-MS: m/z 317.2 (M+1)$^+$.

Step-c: Synthesis of 6-(3,5-dimethylisoxazol-4-yl)-7-methoxyquinolin-2(1H)-one The process of this step was adopted from step-d of intermediate-5. The desired compound obtained as an off white solid (0.2 g, 59%); $^1$H NMR (400 MHz, DMSO-$d_6$): δ 11.76 (bs, 1H), 7.82 (d, J=9.3 Hz, 1H), 7.53 (s, 1H), 6.94 (s, 1H), 6.35 (d, J=9.8 Hz, 1H), 3.81 (s, 3H), 2.26 (s, 3H), 2.07 (s, 3H); LC-MS: m/z 271.1 (M+1)$^+$.

Intermediate-7: Synthesis of 6-bromo-7-methoxy-3-methylquinolin-2(1H)-one

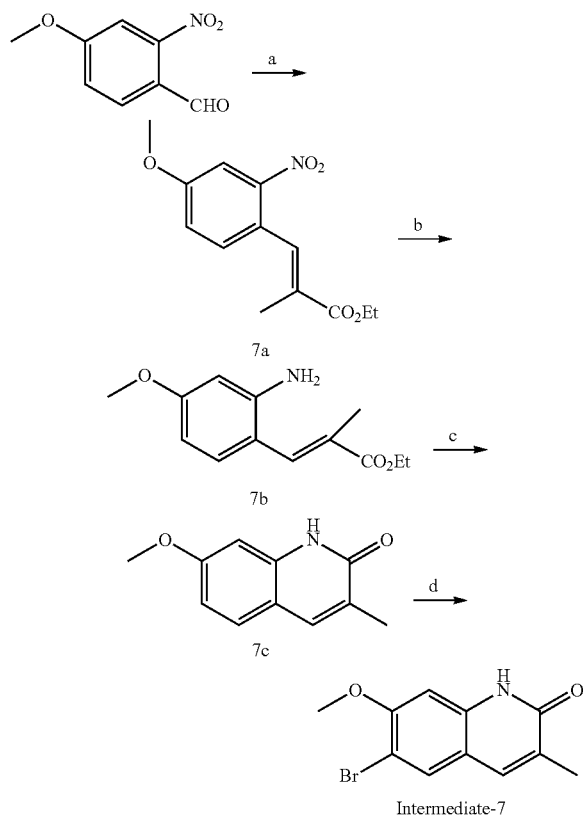

Intermediate-7

Step-a: Synthesis of (E)-ethyl 3-(4-methoxy-2-nitrophenyl)-2-methylacrylate To a stirred suspension of sodium hydride (0.44 g, 11.04 mmol) in THF (20 mL) at 0° C. were added 4-methoxy-2-nitrobenzaldehyde (1.0 g, 5.52 mmol) and ethyl-2-(triphenylphosphoranylidene)propanoate (2.0 g, 5.52 mmol), allowed to stir at RT for 4 h. After completion of the reaction, the reaction mixture diluted with water and extracted with EtOAc (200 mL×2). The combined organic layers were washed with water (200 mL), brine (100 mL), dried over sodium sulphate and concentrated. The residue was purified on silica gel (100-200 mesh) to afford the title product as a brown solid (0.33 g, 22%). $^1$H NMR (400 MHz, CDCl$_3$): δ 7.83 (s, 1H), 7.63 (d, J=2.4 Hz, 1H), 7.26 (s, 1H), 7.20-7.17 (m, 1H), 4.28 (q, J=7.3 Hz, 2H), 3.90 (s, 3H), 1.91 (s, 3H), 1.35 (t, J=7.4 Hz, 3H).

Step-b: Synthesis of (E)-ethyl 3-(2-amino-4-methoxyphenyl)-2-methylacrylate To a solution of (E)-ethyl 3-(4-methoxy-2-nitrophenyl)-2-methylacrylate (0.33 g, 1.23 mmol) in MeOH (10 mL) were added Conc. HCl (2.0 mL) and SnCl$_2$.2H$_2$O (1.46 g, 6.05 mmol) stirred at 80° C. for 4 h. After completion of the reaction, the reaction mixture was filter through celite, the filtrate was concentrated. The residue was diluted with water and extracted with EtOAc (200 mL×2). The combined organic layers were washed with water (200 mL), brine (100 mL), dried over sodium sulphate and concentrated under reduced pressure. The residue was purified by column chromatography by using silica gel (100-200 mesh) to afford the title product as a brown solid (0.2 g, 69%). $^1$H NMR (400 MHz, DMSO-d$_6$): δ 7.50 (s, 1H), 7.01 (d, J=8.3 Hz, 1H), 6.29 (d, J=2.3 Hz, 1H), 6.19 (dd, J=8.8, 2.4 Hz, 1H), 5.24 (bs, 2H), 4.20-4.10 (m, 2H), 3.68 (s, 3H), 1.95 (s, 3H), 1.25 (d, J-=6.8 Hz, 3H); LC-MS: m/z 236.2 (M+1)$^+$.

Step-c: Synthesis of 7-methoxy-3-methylquinolin-2(1H)-one

A solution of (E)-ethyl 3-(2-amino-4-methoxyphenyl)-2-methylacrylate (0.13 g, 0.55 mmol) in dioxane.HCl (4 mL) was heated at 100° C. in a sealed tube for 16 h. After completion of the reaction, the reaction mixture was allowed to RT and concentrated, neutralized with cold aq. NaHCO$_3$ solution. The residue was extracted with EtOAc (200 mL×2) twice. The combined organic layers were washed with water (200 mL), brine (100 mL), dried over sodium sulphate and concentrated under reduced pressure to afford the title product as an off white solid (0.06 g, 58%). $^1$H NMR (400 MHz, DMSO-d$_6$): δ 11.59 (bs, 1H), 7.67 (s, 1H), 7.48 (d, J=8.3 Hz, 1H), 6.79-6.75 (m, 2H), 3.79 (s, 3H), 2.04 (s, 3H); LC-MS: m/z 190.2 (M+1)$^+$.

Step-d: Synthesis of 6-bromo-7-methoxy-3-methylquinolin-2(1H)-one

The process of this step was adopted from step-b of Intermediate-2. The desired compound obtained as an off white solid (0.06 g, 53%); $^1$H NMR (400 MHz, DMSO-d$_6$): δ 11.72 (bs, 1H), 7.84 (s, 1H), 7.66 (s, 1H), 6.91 (s, 1H), 3.87 (s, 3H), 2.04 (s, 3H); LC-MS: m/z 268.0 (M+1)$^+$.

Alternative Procedure: Synthesis of 6-bromo-7-methoxy-3-methylquinolin-2(1H)-one

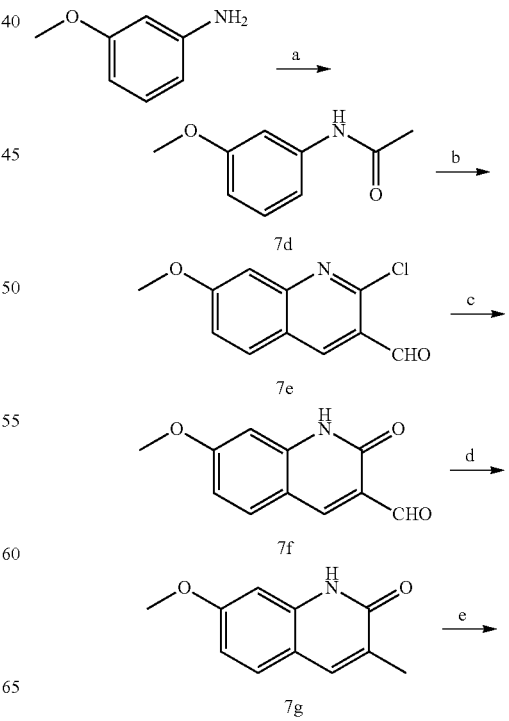

-continued

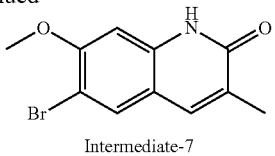

Intermediate-7

Step-a: Synthesis of N-(3-methoxyphenyl)acetamide

To an ice-cooled solution of 3-methoxyaniline (40 g, 325.0 mmol) in AcOH (40 mL) was added aceticanhydride (40 mL) drop wise and stirred at RT for 2 h. Reaction mixture was poured into ice water; solid was filtered off and washed with water, dried under reduced pressure for overnight to give title compound as off white solid (60 g). $^1$H NMR (400 MHz, DMSO-d$_6$) δ 9.89 (s, 1H), 7.27 (s, 1H), 7.18 (t, J=8.0 Hz, 1H), 7.09 (d, J=8.3 Hz, 1H), 6.60 (dd, J=2.2 Hz, 8.2 Hz, 1H), 3.71 (s, 3H), 2.02 (s, 3H); LC-MS: m/z 166.2 (M+1)$^+$.

Step-b: Synthesis of 2-chloro-7-methoxyquinoline-3-carbaldehyde

POCl$_3$ (339 mL, 3636.0 mmol) was added drop wise to DMF (112 mL, 1454.4 mmol) at 0° C., after stirred for 5 min, N-(3-methoxyphenyl)acetamide (60 g, 363.6 mmol) was added and resulting solution was heated to 100° C. for 3 h. The reaction mixture was cooled to room temperature and poured into ice water; solid was filtered off and washed with water, dried under reduced pressure for overnight to give title compound as pale yellow solid (88 g). $^1$H NMR (400 MHz, DMSO-d$_6$) δ 10.34 (s, 1H), 8.88 (s, 1H), 8.18 (d, J=8.8 Hz, 1H), 7.45 (d, J=2.5 Hz, 1H), 7.39 (dd, J=2.5 Hz, 9.3 Hz, 1H), 3.98 (s, 3H); LC-MS: m/z 222.1 (M+1)$^+$.

Step-c: Synthesis of 7-methoxy-2-oxo-1,2-dihydroquinoline-3-carbaldehyde

A suspension of 2-chloro-7-methoxyquinoline-3-carbaldehyde (8.0 g, 36.2 mmol) in 70% acetic acid (370 mL) was heated to 110° C. for 16 h. Upon cooling the reaction mixture to room temperature and poured into crushed ice; solid was filtered off and washed with water, dried under reduced pressure for overnight to give title compound as pale yellow solid (5.6 g, 76%). $^1$H NMR (400 MHz, DMSO-d$_6$) δ 12.07 (s, 1H), 10.18 (s, 1H), 8.43 (s, 1H), 7.84 (d, J=8.9 Hz, 1H), 6.89 (dd, J=2.5 Hz, 8.8 Hz, 1H), 6.82 (d, J=1.9 Hz, 1H), 3.86 (s, 3H): LC-MS: m/z 204.1 (M+1)$^+$.

Step-d: Synthesis of 7-methoxy-3-methylquinolin-2(1H)-one

To an ice-cooled solution of 7-methoxy-2-oxo-1,2-dihydroquinoline-3-carbaldehyde (6 g, 29.55 mmol) in TFA (110 mL) was added triethyl silane (13.2 mL) drop wise and stirred at RT for 16 h. Reaction mixture was poured into ice water: solid was filtered off and washed with water, dried under reduced pressure for overnight to give title compound as pale yellow solid crude (6 g). $^1$H NMR (400 MHz, DMSO-d$_6$) δ 11.59 (s, 1H), 7.67 (s, 1H), 7.48 (d, J=8.8 Hz, 1H), 6.78-6.75 (m, 2H), 3.78 (s, 3H), 2.04 (s, 3H); LC-MS: m/z 190.1 (M+1)$^+$.

Step-e: Synthesis of 6-bromo-7-methoxy-3-methylquinolin-2(1H)-one

The process of this step was adopted from step-b of Intermediate-2.

Intermediate-7.1: Synthesis of 6-bromo-3-cyclohexyl-7-methoxyquinolin-2(1H)-one

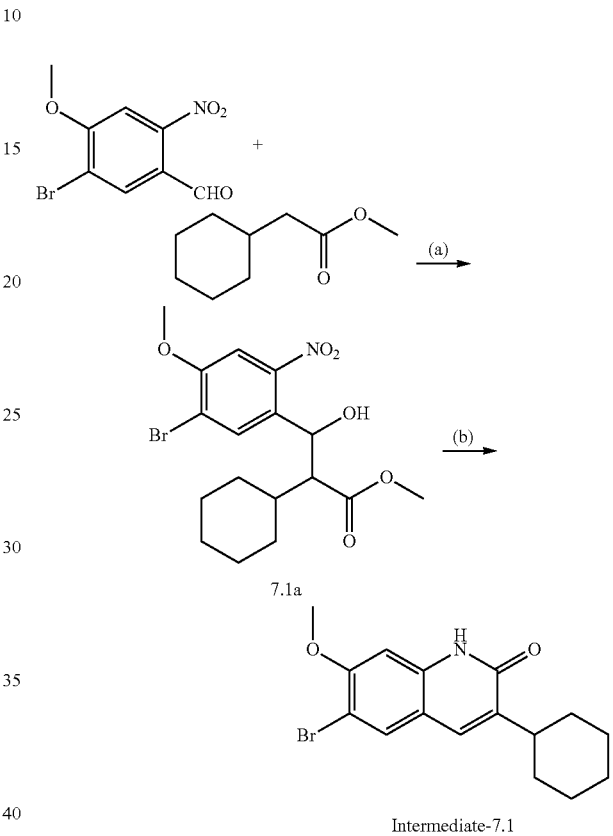

Intermediate-7.1

Step-a: Synthesis of methyl 3-(5-bromo-4-methoxy-2-nitrophenyl)-2-cyclohexyl-3-hydroxy propanoate To a solution of methyl 2-cyclohexylacetate (0.39 g, 2.49 mmol) in THF (20 mL) at −78° C. was added LDA 2.0 M in THF (2.4 mL, 4.80 mmol) and stirred for 1 h at same conditions, then added 5-bromo-4-methoxy-2-nitrobenzaldehyde (0.5 g, 1.92 mmol) in THF and stirred at −78° C. for 2 h. The reaction mixture quenched with sat NH$_4$Cl and extracted with EtOAc (150 mL) and washed with water (150 mL), dried over sodium sulphate and concentrated under reduced pressure. The residue was used for further step without purification (0.07 g crude).

Step-b: Synthesis of 6-bromo-3-cyclohexyl-7-methoxyquinolin-2(1H)-one

To a solution of methyl 3-(5-bromo-4-methoxy-2-nitrophenyl)-2-cyclohexyl-3-hydroxy propanoate (0.5 g, 1.29 mmol) in AcOH (10 mL) was added iron powder (0.2 g, 3.88 mmol) and stirred at 80° C. for 1 h. Reaction mixture filtered through celite, washed with EtOAc combined filtrate was concentrated, the residue was diluted with water and extracted with EtOAc (100 mL), washed with brine (100 mL), dried over sodium sulphate and concentrated. The residue was used for further step without purification (crude-0.4 g). $^1$H NMR (400 MHz, DMSO-d$_6$): δ 11.70 (s, 1H), 7.89 (s, 1H), 7.59 (s, 1H), 6.89 (s, 1H), 3.86 (s, 3H), 2.67-2.55 (m, 1H), 1.83-1.77 (m, 6H), 1.34-1.23 (m, 4H); LC-MS: m/z 336.1 (M+1)$^+$.

Intermediate-8: Synthesis of 6-bromo-7-methoxy-4-methylquinolin-2(1H)-one

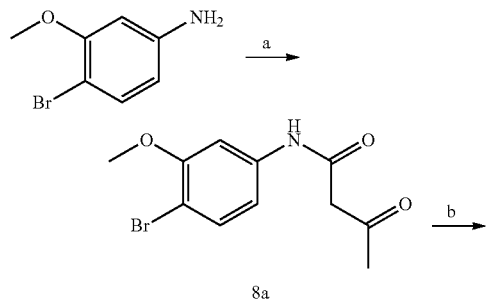

8a

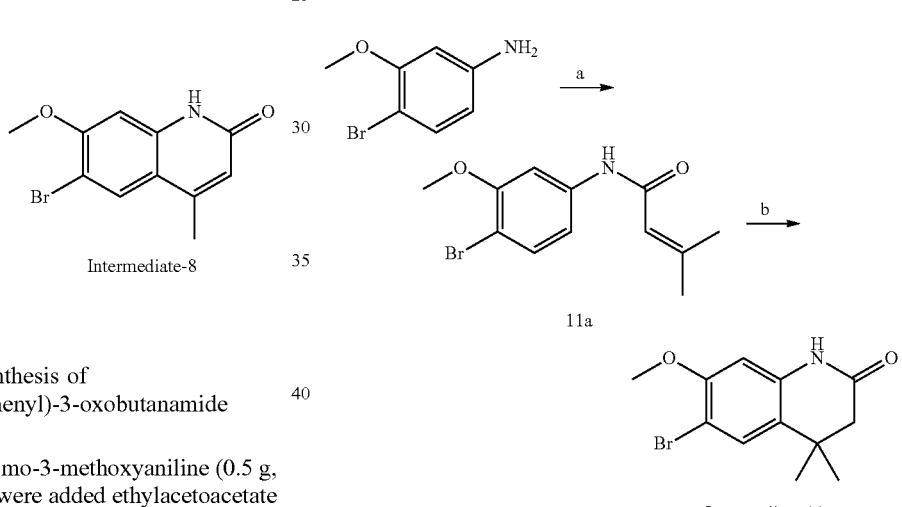

Intermediate-8

Step-a: Synthesis of N-(4-bromo-3-methoxyphenyl)-3-oxobutanamide

To a stirred solution of 4-bromo-3-methoxyaniline (0.5 g, 2.47 mmol) in toluene (5 mL) were added ethylacetoacetate (0.5 mL, 3.71), sodium ethoxide (0.34 g, 4.94 mmol), and heated to 110° C. for 16 h. After completion of the reaction, the reaction mixture was diluted with EtOAC (100 mL), washed with water (100 mL), brine (100 mL), dried over sodium sulphate and concentrated. The residue was purified by column chromatography by using silica gel (60-120 mesh) to afford the title product as yellow solid (0.4 g, 90%). $^1$H NMR (400 MHz, DMSO-d$_6$): δ 10.21 (s, 1H), 7.48-7.43 (m, 2H), 7.11-7.08 (m, 1H), 3.83 (s, 3H), 3.54 (s, 2H), 2.20 (s, 3H); ES-MS: m/z 286.1 (M+1)$^+$.

Step-b: Synthesis of 6-bromo-7-methoxy-4-methylquinolin-2(1H)-one

The process of this step was adopted from step-d of intermediate-5. The desired compound obtained as a pale yellow solid (0.33 g, 90%); $^1$H NMR (400 MHz, DMSO-d$_6$): δ 11.56 (bs, 1H), 7.86 (s, 1H), 6.93 (s, 1H), 6.26 (s, 1H), 3.88 (s, 3H), 2.37 (s, 3H); LC-MS: m/z 268.1 (M+1)$^+$.

The below Intermediates 9 and 10 were prepared according to the above protocol.

| Int No. | Structure | Characterization data |
|---|---|---|
| 9 | 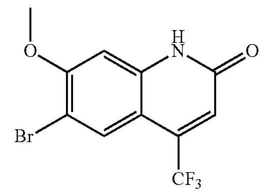 [SMILES: COc1cc2[nH]c(=O)cc(C(F)(F)F)c2cc1Br] | LC-MS: m/z 323.3 (M + 1)$^+$. |
| 10 | 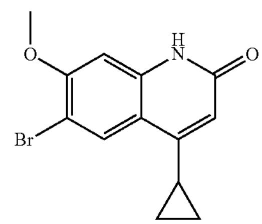 | LC-MS: m/z 297.0 (M + 1)$^+$. |

Intermediate-11: Synthesis of 6-bromo-7-methoxy-4,4-dimethyl-3,4-dihydroquinolin-2(1H)-one 11a Intermediate-11

Step-a: Synthesis of N-(4-bromo-3-methoxyphenyl)-3-methylbut-2-enamide

A solution of 4-bromo-3-methoxyaniline (2.0 g, 9.90 mmol) in chloroform (20 mL) was added 3-methylbut-2-enoyl chloride and refluxed for 3 h. After completion of the reaction, the reaction mixture was poured over cold aq. NaHCO$_3$ solution and extracted with EtOAC (50 mL), washed with water (50 mL), brine (50 mL), dried over sodium sulphate and concentrated. The residue was used for next step without further purification (1.7 g). $^1$H NMR (400 MHz, DMSO-d$_6$): δ 9.95 (s, 1H), 7.56 (d, J=2.5 Hz, 1H), 7.44 (d, J=8.3 Hz, 1H), 7.11 (dd, J=2.2, 8.4 Hz, 1H), 5.84 (s, 1H), 3.80 (s, 3H), 2.14 (s, 3H), 1.84 (s, 3H); LC-MS: m/z 284.0 (M+1)$^+$.

Step-b: Synthesis of 6-bromo-7-methoxy-4,4-dimethyl-3,4-dihydroquinolin-2(1H)-one N-(4-bromo-3-methoxyphenyl)-3-methylbut-2-enamide (0.5 g, 1.76 mmol) was heated at 130° C. before aluminum chloride (0.35 g, 2.64 mmol) was added portion wise over a period of 1.5 h. After completion of the reaction, the reaction mixture was diluted with H₂O (50 mL), extracted with EtOAc (100 mL×2). The combined organic layers were washed with water (50 mL), brine (50 mL), dried over sodium sulphate and concentrated. The residue was purified by column chromatography by using silica gel (100-200 mesh) to afford the title product as a off-white solid. (0.15 g, 31%). $^1$H NMR (400 MHz, DMSO-d$_6$): δ 10.14 (bs, 1H), 7.38 (s, 1H), 6.62 (s, 1H), 3.77 (s, 3H), 2.32 (s, 2H), 1.19 (s, 6H); ES-MS: m/z 285.0 (M+1)$^+$.

Intermediate-12: Synthesis of 6-bromo-7-methoxy-3,3-dimethylquinoline-2,4(1H,3H)-dione

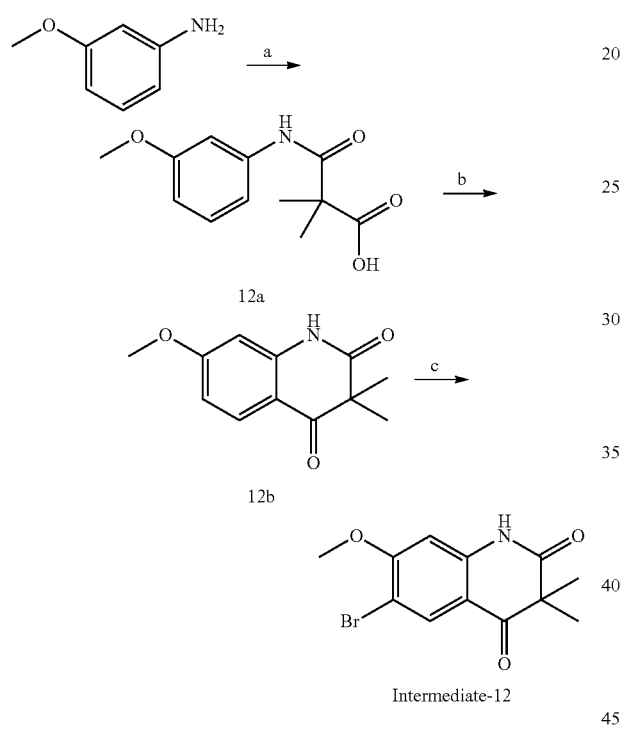

Intermediate-12

Step-a: Synthesis of 3-((3-methoxyphenyl)amino)-2,2-dimethyl-3-oxopmpanoicacid

A solution of 2,2-dimethylmalonic acid (5.3 g, 40.65 mmol) and thionyl chloride (3.5 mL, 48.78 mmol) in THF (20 mL) was refluxed for 2 h and then concentrated. The residue was dissolved in THF (20 mL) and solution was slowly added into a solution of 3-methoxy aniline (5 g, 40.65 mmol) and triethylamine (5.6 mL, 40.65 mmol) in THF (20 mL) at 0° C., then the reaction mixture allowed to stir at RT for 1 h. After completion of the reaction, the reaction mixture concentrated and diluted with 5N NaOH solution (p$^H$~9-11), washed with EtOAc. The aqueous layer was acidified with Conc. HCl and the resulting precipitate was collected and washed with water to afford the title product as a white solid (2.5 g, 29%). $^1$H NMR (400 MHz, DMSO-d$_6$): δ 12.65 (bs, 1H), 9.41 (s, 1H), 7.33 (t, J=1.9 Hz, 1H), 7.24-715 (m, 2H), 6.63-6.60 (m, 1H), 3.71 (s, 3H), 1.40 (s, 6H), ES-MS: m/z 236.1 (M−1)$^-$.

Step-b: Synthesis of 7-methoxy-3,3-dimethylquinoioline-2,4(1H,3H)-dione

A solution of 3-((3-methoxyphenyl) amino)-3-oxopropanoic acid (0.5 g, 2.39 mmol) in poly phosphoric acid (5 mL) was heated to 130° C. for 4 h. After completion of the reaction, the reaction mixture was poured into ice water and extracted with EtOAc (100 mL). The organic layer was washed with brine (100 mL), dried over sodium sulphate and concentrated. The residue was purified on silica gel (60-120 mesh) to afford the title product as a yellow solid (0.25 g, 54%); ES-MS: m/z 220.1 (M+1)$^+$.

Step-c: Synthesis of 6-bromo-7-methoxy-3,3-dimethylquinoline-2,4(1H,3H)-dione

The process of this step was adopted from step-b of intermediate-2. The desired compound obtained as white solid 0.15 g (73%); $^1$H NMR (400 MHz, DMSO-d$_6$): δ 10.80 (s, 1H), 7.84 (s, 1H), 6.74 (s, 1H), 3.91 (s, 3H), 1.33 (s, 6H); LC-MS: m/z 299.1 (M+1)$^+$.

Intermediate-13: Synthesis of 6-bromo-7-methoxy-3,3-dimethyl-3,4-dihydroquinolin-2(1H)-one

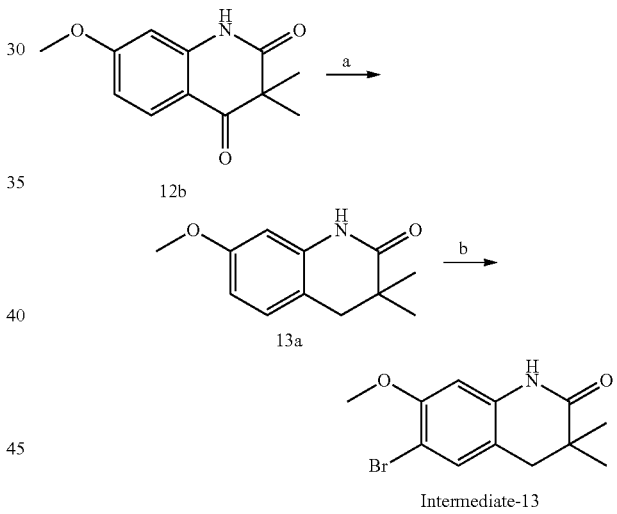

Intermediate-13

Step-a: Synthesis of 7-methoxy-3,3-dimethyl-3,4-dihydroquinolin-2(1H)-one

To a stirred solution of 7-methoxy-3,3-dimethylquinoline-2,4(1H,3H)-dione (0.25 g, 1.14 mmol) in AcOH (28 mL), were added Ac₂O (0.12 mL), Conc. H₂SO₄ (0.02 mL). 10% Pd—C then hydrogenated using hydrogen bladder pressure at RT for 16 h. Then the reaction mixture filtered, powdered NaHCO₃ was added to the filtrate and extracted with EtOAc (100 mL) and organic layer washed with water (100 mL), dried over sodium sulphate and concentrated. The residue was purified by column chromatography by using silica gel (60-120 mesh) to afford the title product as a pale yellow solid (0.15 g, 65%). $^1$H NMR (400 MHz, DMSO-d$_6$): δ 9.91 (s, 1H), 7.04 (d, J=8.3 Hz, 1H), 6.50-6.43 (m, 2H), 3.68 (s, 3H), 2.65 (s, 2H), 1.03 (s, 6H); LC-MS: m/z 206.2 (M+1)$^+$.

Step-b: Synthesis of 6-bromo-7-methoxy-3,3-dimethyl-3,4-dihydroquinolin-2(1H)-one The process of this step was adopted from step-b of intermediate-2. The desired compound obtained as a white solid (0.09 g, 60%). $^1$H NMR (400 MHz, DMSO-$d_6$): δ 10.03 (s, 1H), 7.34 (s, 1H), 6.60 (s, 1H), 3.76 (s, 3H), 2.68 (s, 2H), 1.03 (s, 6H); LC-MS: m/z 286.1 (M+1)$^+$.

Intermediate-14: Synthesis of 6-(3,5-dimethylisoxazol-4-yl)-7-methoxy-3,4-dihydroquinolin-2(1H)-one

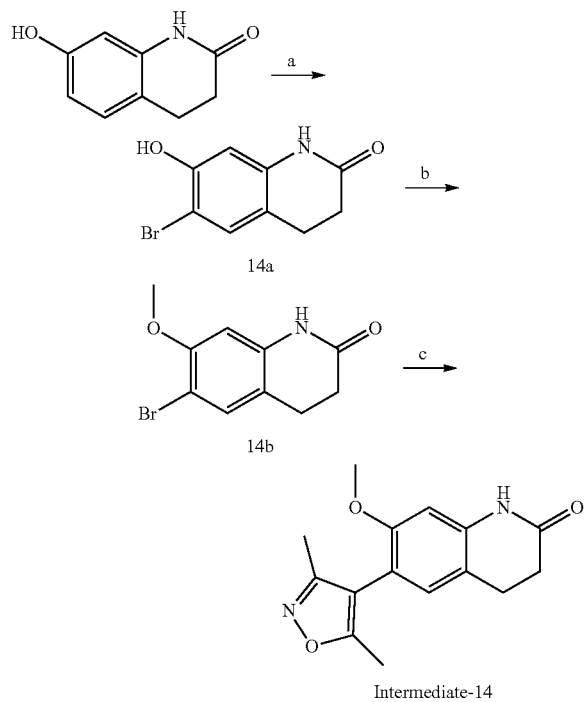

Intermediate-14

Step-a: Synthesis of 6-bromo-7-hydroxy-3,4-dihydroquinolin-2(1H)-one

The process of this step was adopted from step-b of intermediate-2. The desired compound obtained as a white solid (2.2 g, 75%); $^1$H NMR (400 MHz DMSO-de) δ 9.46 (bs, 1H), 9.39 (bs, 1H), 7.18 (s, 1H), 6.56 (s, 1H), 2.82 (t, J=7.3 Hz, 2H), 2.52 (t, J=7.3 Hz, 2H); ES-MS m/z 244.1 (M+1)$^+$.

Step-b: Synthesis of 6-bromo-7-methoxy-3,4-dihydroquinolin-2(1H)-one

To a stirred suspension of 6-bromo-7-hydroxy-3,4-dihydroquinolin-2(1H)-one (2.2 g, 9 mmol) in ethanol was added K$_2$CO$_3$ (2.49 g, 18.1 mmol). The resulting mixture was refluxed for 2 h, then reaction mixture cooled to 0° C. and methyl iodide (2.5 g, 18.1 mmol), KI (0.075 g, 18.1 mmol) were added. The reaction mixture was refluxed for 12 h, filtered, concentrated under reduced pressure. The residue was purified by chromatography on silica (10% EtOAc in hexanes) to give the desired product as a off-white solid (1.7 g, 73%). $^1$H NMR (400 MHz DMSO-$d_6$) δ 10.07 (bs, 1H), 7.30 (s, 1H), 6.60 (s, 1H), 3.76 (s, 3H), 2.81-2.78 (m, 2H), 2.43-2.40 (m, 2H); ES-MS m/z 256.1 (M+1)$^+$.

Step-c: Synthesis of 6-(3,5-dimethylisoxazol-4-yl)-7-methoxy-3,4-dihydroquinolin-2(1H)-one The process of this step was adopted from step-f of intermediate-1. The desired compound obtained as an off white solid (0.150 g, 47%). $^1$H NMR (400 MHz DMSO-$d_6$) δ 10.09 (s, 1H), 6.99 (s, 1H), 6.62 (s, 1H), 3.69 (s, 3H), 3.82 (t, J=7.6 Hz, 2H), 2.45 (t, J=7.6 Hz, 2H), 2.23 (s, 3H), 2.05 (s, 3H); ES-MS m/z 273.1 (M+1)$^+$.

Intermediate-15: Synthesis of 1-(pyridin-4-yl)ethylmethanesulfonate

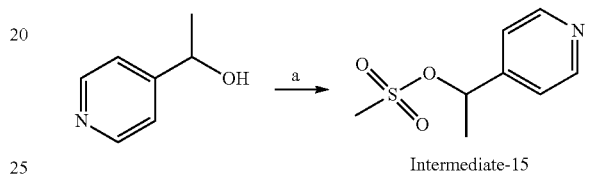

Intermediate-15

Step-a

To an ice cooled solution of 1-(pyridin-4-yl)ethanol (0.25 g, 2.07 mmol) in DCM (5 mL) were added triethylamine (0.58 mL, 4.14 mmol) followed by methanesulfonylchloride (0.32 mL, 4.14 mmol) and stirred at RT for 4 h. After completion of the reaction, the reaction mixture was diluted with DCM (50 mL) and washed with water (50 mL), brine (20 mL), dried over sodium sulphate and concentrated. The residue was used for next step without further purification (0.42 g, 100%). $^1$H NMR (400 MHz, DMSO-$d_6$): δ 8.61 (d, J=6.0 Hz, 2H), 7.44 (d, J=6.0 Hz, 2H), 5.80 (qt, J=6.8 Hz, 1H), 3.20 (s, 3H), 1.60 (d, J=6.8 Hz, 3H); LC-MS: m/z 202.1 (M+1)$^+$.

The below Intermediates 16 to 26, 26a, 26b, 26c and 26 d were prepared according to the above protocol.

| Int No. | Structure | Characterization data |
|---|---|---|
| 16 | 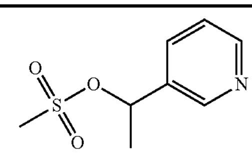 | — |
| 17 | 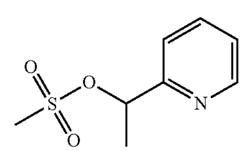 | LC-MS: m/z 202.1 (M + 1)$^+$. |
| 18 | 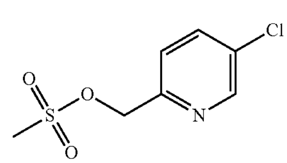 | LC-MS: m/z 221.1 (M + 1)$^+$. |

-continued

| Int No. | Structure | Characterization data |
|---|---|---|
| 19 | (5-fluoropyridin-2-yl)methyl methanesulfonate | — |
| 20 | (3-fluoropyridin-2-yl)methyl methanesulfonate | LC-MS: m/z 206.1 (M + 1)+. |
| 21 | (6-methylpyridin-3-yl)methyl methanesulfonate | — |
| 22 | 1-(4-chlorophenyl)ethyl methanesulfonate | — |
| 23 | 2-(pyridin-2-yl)ethyl methanesulfonate | ES-MS: m/z 202.1 (M + 1)+. |
| 24 | (1-Boc-piperidin-4-yl)methyl methanesulfonate | — |
| 25 | pyrazin-2-ylmethyl methanesulfonate | ES-MS: m/z 189.1 (M + 1)+. |
| 26 | thiazol-2-ylmethyl methanesulfonate | ES-MS: m/z 194.1 (M + 1)+. |
| 26a | (5-methoxypyridin-2-yl)methyl methanesulfonate | LC-MS: m/z 218.1 (M + 1)+. |
| 26b | 2-(4-chlorophenyl)ethyl methanesulfonate (MsO) | — |
| 26c | 2-(4-Boc-piperazin-1-yl)ethyl methanesulfonate | — |
| 26d | (5-bromopyridin-2-yl)methyl methanesulfonate | — |

Intermediate-27: Synthesis of 2-(iodomethyl)-5-(trifluoromethyl)pyridine

<chemical scheme: (5-(trifluoromethyl)pyridin-2-yl)methanol → Intermediate-27 (2-(iodomethyl)-5-(trifluoromethyl)pyridine)>

To a stirred solution of (5-(trifluoromethyl)pyridin-2-yl)methanol (0.9 g, 5.02 mmol) in anhydrous THF (10 mL), triphenylphosphine (1.97 g, 7.54 mmol), imidazole (1.02 g, 15.08 mmol) and iodine (1.92 g, 7.54 mmol) were added sequentially at RT. The reaction mixture was stirred for 30 min at room temperature. After complete of the reaction, the reaction mixture was quenched with an aqueous sodium thiosulfate (20 mL). The organic solvent was separated and aqueous layer was extracted with diethyl ether. The combined organic layer were washed with brine solution and dried over anhydrous $Na_2SO_4$. The solvents were removed under reduced pressure. The residue was purified by column chromatography (60-120 silica gel and 2% EtOAc in hexane as eluent) to yield the title compound (0.30 g, 20%). $^1$H NMR, $CDCl_3$, 300 MHz: δ 8.82 (s, 1H), 7.86 (dd, J=8.1 & 1.8 Hz, 1H), 7.51 (d, J=8.1 Hz, 1H), 4.55 (s, 2H); LC-MS: m/z 287.8 (M+1)+.

Intermediate-28: Synthesis of 7-bromo-6-methoxy-4-(pyridin-4-ylmethyl)-2H-benzo[b][1.4]oxazin-3(4H)-one (Method-A)

<chemical scheme: Intermediate-2 + 4-(bromomethyl)pyridine·HBr →>

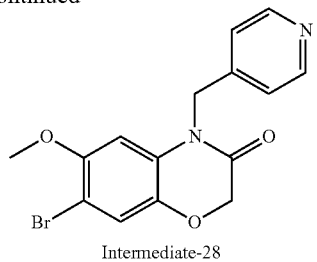

Intermediate-28

To a solution of intermediate-2 (0.5 g, 1.98 mmol) in CH₃CN (20 mL) were added cesium carbonate (1.58 g, 4.85 mmol) followed by 4-(bromomethyl)pyridine.HBr (0.73 g, 2.91 mmol) and stirred at 60° C. for 6 h. After completion of the reaction, the reaction mixture was concentrated, diluted with water and extracted with EtOAc (200 mL×2) twice. The combined organic layers were washed with water (200 mL), brine (100 mL), dried over sodium sulphate and concentrated under reduced pressure. The residue was purified on silica gel (100-200 mesh) to afford the titled product as off-white solid (0.52 g, 74%). ¹H NMR (400 MHz, DMSO-d₆) δ 8.52 (d, J=4.4 Hz, 2H), 7.31-7.30 (m, 3H), 6.89 (s, 1H), 5.26 (s, 2H), 4.78 (s, 2H), 3.66 (s, 3

Intermediate-29: Synthesis of 6-bromo-1-((6-chloropyridin-3-yl) methyl)-7-methoxyquinolin-2(1H)-one (Method-B)

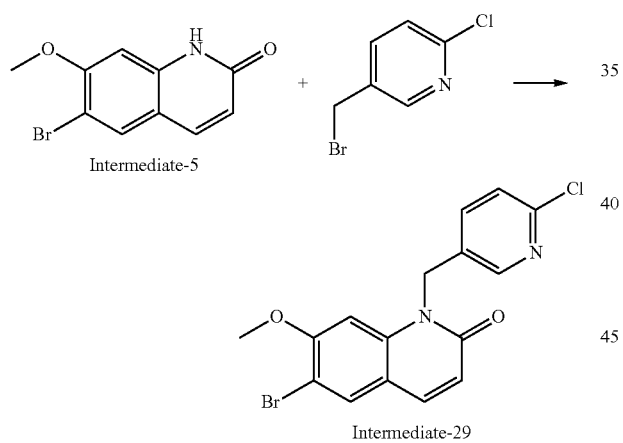

Intermediate-29

To a solution of intermediate-5 (0.2 g, 0.78 mmol) in DMF (5 mL) were add potassium carbonate (0.32 g, 0.99 mmol) followed by 2-chloro-5-(chloromethyl)pyridine (0.33 g, 2.36 mmol) and stirred at RT for 16 h. After completion of the reaction, the reaction mixture was diluted with water and extracted with EtOAc (200 mL×2). The combined organic layers were washed with water (200 mL), brine (100 mL), dried over sodium sulphate and concentrated. The residue was purified by preparative TLC to afford the title product as an off white solid (0.05 g, 17%). ¹H NMR (400 MHz, DMSO-d₆): δ 8.44 (d, J=2.5 Hz, 1H), 8.04 (s, 1H), 7.90 (d, J=9.3 Hz, 1H), 7.67 (dd, J=5.9 & 2.4 Hz, 1H), 7.46 (d, J=8.3 Hz, 1H), 6.98 (s, 1H), 6.60 (d, J=9.3 Hz, 1H), 5.60 (s, 2H), 3.86 (s, 3H); LC-MS: m/z 379.0 (M+1)⁺.

Intermediate-30: Synthesis of 6-bromo-7-methoxy-1-(pyrimidin-4-ylmethyl)quinolin-2(1H)-one (Method-C)

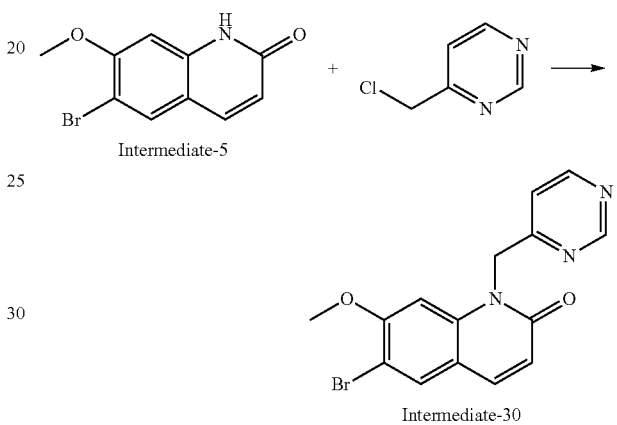

Intermediate-30

To a stirred solution of intermediate-5 (0.15 g, 0.59 mmol) in DMF (5 mL) were added 60% NaH (0.035 g, 0.088 mmol). 4-(chloromethyl)pyrimidine (0.113 g, 0.88 mmol), and stirred at RT for 16 h. After completion of the reaction, the reaction mixture was poured on ice water, diluted with EtOAC (30 mL), washed with water (50 mL), brine (50 mL), dried over sodium sulphate and concentrated. The residue was purified on silica gel (100-200 mesh) to afford the titled product as off-white solid (0.08 g, 39%). ¹H NMR (400 MHz, DMSO-d₆): δ 9.07-9.06 (m, 1H), 8.73 (d, J=4.8 Hz, 1H), 8.04 (s, 1H), 7.94-7.90 (m, 1H), 7.41-7.39 (m, 1H), 6.94 (s, 1H), 6.57 (d, J=9.8 Hz, 1H), 5.66 (s, 2H), 3.80 (s, 3H); LC-MS: m/z 346.1 (M+1)⁺.

The below intermediates were prepared by using the above three different methods. This N-alkylation reaction can be carried out by using the appropriate reactant having alkylhalide/mesylate in presence of suitable base.

| Int No. | Structure | Method | Characterization data |
|---|---|---|---|
| 31 | 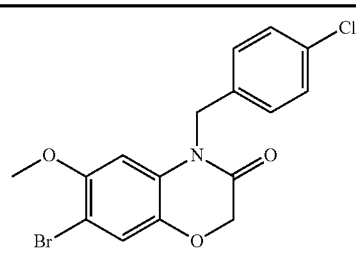 | A | ¹H NMR (400 MHz, CDCl₃) δ 7.40-7.10 (m, 5H), 6.39 (s, 1H), 5.12 (s, 2H), 4.67 (s, 2H), 3.67 (s, 3H); ES-MS: m/z 382.1 (M + H)⁺. |

| Int No. | Structure | Method | Characterization data |
|---|---|---|---|
| 32 | 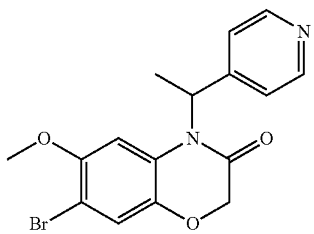 [SMILES: COc1cc2c(cc1Br)OCC(=O)N2C(C)c1ccncc1] | A | $^1$H NMR (400 MHz, DMSO-d$_6$): δ 8.56 (d, J = 6.0 Hz, 2H), 7.36 (d, J = 5.2 Hz, 2H), 7.32 (s, 1H), 6.37 (s, 1H), 6.15-60.5 (m, 1H), 4.74-4.65 (m, 2H), 3.52 (s, 3H), 1.79 (d, J = 6.8 Hz, 3H); LC-MS: m/z 364.1.0 (M + 1)$^+$. |
| 33 | 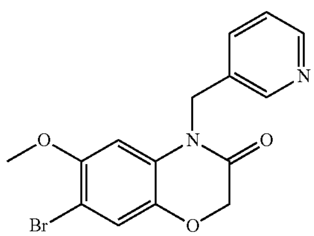 [SMILES: COc1cc2c(cc1Br)OCC(=O)N2Cc1cccnc1] | A | $^1$H NMR (400 MHz, CDCl$_3$) δ 8.63-8.56 (m, 2H), 7.59 (d, J = 8.0 Hz, 1H), 7.31-7.29 (m, 1H), 7.21 (s, 1H), 6.41 (s, 1H), 5.18 (s, 2H), 4.68 (s, 2H), 3.69 (s, 3H); LC-MS: m/z 351.0 (M + 1)$^+$. |
| 34 | 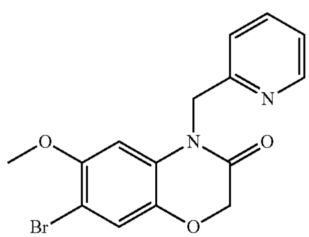 [SMILES: COc1cc2c(cc1Br)OCC(=O)N2Cc1ccccn1] | A | $^1$H NMR (400 MHz, CDCl$_3$) δ 8.56 (d, J = 4.0 Hz, 1H), 7.66 (td, J = 7.6 & 2.0 Hz, 1H), 7.32 (d, J = 7.6 Hz, 1H), 7.23-7.20 (m, 1H), 7.17 (s, 1H), 6.89 (s, 1H), 5.26 (s, 2H), 4.66 (s, 2H), 3.74 (s, 3H); LC-MS: m/z 349.0 (M + 1)$^+$. |
| 35 | 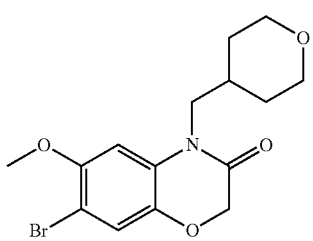 [SMILES: COc1cc2c(cc1Br)OCC(=O)N2CC1CCOCC1] | A | $^1$H NMR (400 MHz, DMSO-d$_6$): δ 7.26 (s, 1H), 6.94 (s, 1H), 4.60 (s, 2H), 3.92 (d, J = 7.2 Hz, 2H), 3.86 (s, 3H), 3.81 (dd, J = 11.6 & 2.8 Hz, 2H), 3.21 (t, J = 5.8 Hz, 2H), 1.94-1.89 (m, 1H), 1.52-1.48 (m, 2H), 1.30-1.18 (m, 2H); LC-MS: m/z 358.1 (M + 1)$^+$. |
| 36 | 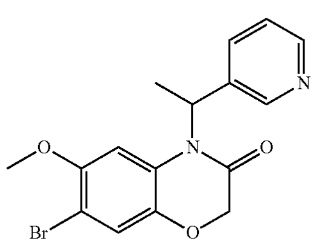 [SMILES: COc1cc2c(cc1Br)OCC(=O)N2C(C)c1cccnc1] | A | $^1$H NMR (400 MHz, DMSO-d$_6$): δ 8.60 (d, J = 2.4 Hz, 1H), 8.50 (d, J = 4.4 Hz, 1H), 7.77 (d, J = 7.6 Hz, 1H), 7.40 (dd, J = 8.4 & 3.6 Hz, 1H), 7.30 (s, 1H), 6.45 (s, 1H), 6.14 (q, J = 7.6 Hz, 1H), 4.73-4.63 (m, 2H), 3.54 (s, 3H), 1.83 (d, J = 7.6 Hz, 3H); LC-MS: m/z 364.0 (M + 1)$^+$. |
| 37 | 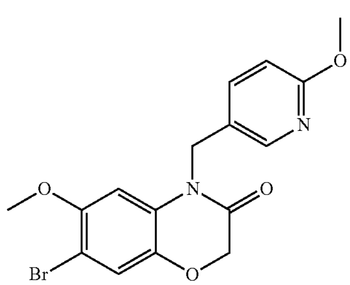 | A | 1H NMR (400 MHz, CDCl$_3$): δ 8.13 (d, J = 2.4 Hz, 1H), 7.50 (dd, J = 8.8 & 2.8 Hz, 1H), 7.19 (s, 1H), 6.72 (d, J = 8.4 Hz, 1H), 6.51 (s, 1H), 5.08 (s, 2H), 4.64 (s, 2H), 3.91 (s, 3H), 3.74 (s, 3H). LC-MS: m/z 381.0 (M + 1)$^+$. |

| Int No. | Structure | Method | Characterization data |
|---|---|---|---|
| 38 | 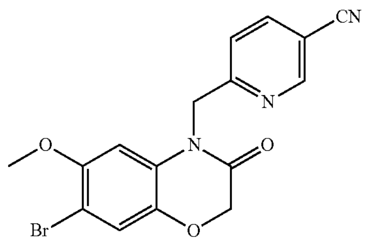 [SMILES: COc1cc2c(cc1Br)OCC(=O)N2Cc1ccc(C#N)cn1] | A | ¹H NMR (400 MHz, CDCl₃): δ 8.84 (d, J = 2.0 Hz, 1H), 7.95 (dd, J = 7.6 & 2.0 Hz, 1H), 7.49 (d, J = 6.0 Hz, 1H), 7.21 (s, 1H), 6.76 (s, 1H), 5.29 (s, 2H), 4.66 (s, 2H), 3.77 (s, 3H); LC-MS: m/z 376.0 (M + 1)⁺. |
| 39 | 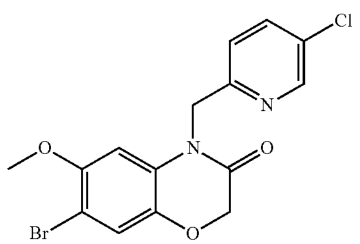 [SMILES: COc1cc2c(cc1Br)OCC(=O)N2Cc1ccc(Cl)cn1] | A | ¹H NMR (400 MHz, CDCl₃): δ 8.51 (d, J = 2.4 Hz, 1H), 7.64 (dd, J = 8.8 & 2.4 Hz, 1H), 7.32 (d, J = 8.4 Hz, 1H), 7.17 (s, 1H), 6.90 (s, 1H), 5.21 (s, 2H), 4.64 (s, 2H), 3.70 (s, 3H); LC-MS: m/z 384.0 (M + 1)⁺. |
| 40 | 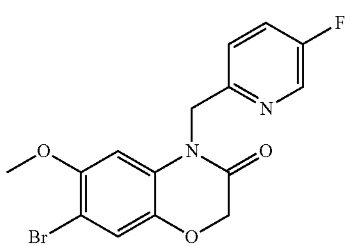 [SMILES: COc1cc2c(cc1Br)OCC(=O)N2Cc1ccc(F)cn1] | A | ¹H NMR (400 MHz, CDCl₃) δ 8.41 (s, 1H), 7.45-735 (m, 2H), 7.17 (s, 1H), 6.95 (s, 1H), 5.23 (s, 2H), 4.64 (s, 2H), 3.79 (s, 3H); LC-MS: m/z 367.0 (M + 1)⁺. |
| 41 | 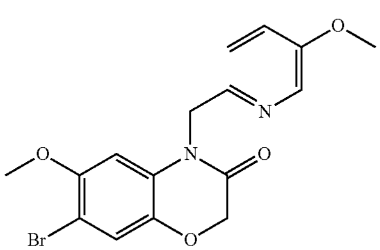 | A | ¹H NMR (400 MHz, CDCl₃) δ 8.23 (d, J = 2.8 Hz, 1H), 7.29 (d, J = 8.8 Hz, 1H), 7.18-7.15 (m, 2H), 7.03 (s, 1H), 5.19 (s, 2H), 4.63 (s, 2H), 3.84 (s, 3H), 3.79 (s, 3H); LC-MS: m/z 381.0 (M + 1)⁺. |
| 42 | 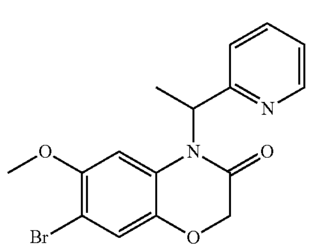 [SMILES: COc1cc2c(cc1Br)OCC(=O)N2C(C)c1ccccn1] | A | ¹H NMR (400 MHz, CDCl₃) δ 8.59-8.58 (m, 1H), 7.81-7.77 (m, 1H), 7.43-7.41 (m, 1H), 7.33-7.26 (m, 1H), 7.13 (s, 1H), 6.61 (s, 1H), 6.23-6.18 (m, 1H), 4.66 (s, 2H), 3.54 (s, 3H), 1.80 (d, J = 6.9 Hz, 3H); LC-MS: m/z 365.0 (M + 1)⁺. |
| 43 | 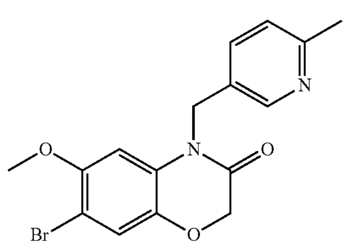 | A | LC-MS: m/z 363.0 (M + 1)⁺. |

| Int No. | Structure | Method | Characterization data |
|---|---|---|---|
| 44 | 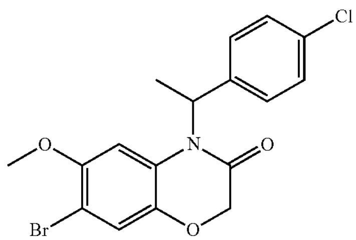 [SMILES: COc1cc2c(cc1Br)OCC(=O)N2C(C)c1ccc(Cl)cc1] | A | ¹H NMR (400 MHz, DMSO-d₆): δ 7.45-7.35 (m, 4H), 6.40 (s, 1H), 6.13-6.11 (m, 1H), 4.72-4.63 (m, 2H), 4.04-4.02 (m, 1H), 3.51 (s, 3H), 1.78 (d, J = 6.9 Hz, 3H); ES-MS: m/z 398.1 (M + 1)⁺. |
| 45 | 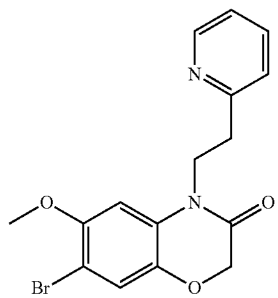 [SMILES: COc1cc2c(cc1Br)OCC(=O)N2CCc1ccccn1] | A | ¹H NMR (400 MHz, DMSO-d₆): δ 8.52 (d, J = 4.4 Hz, 1H), 7.71-7.67 (m, 1H), 7.29-7.21 (m, 3H), 6.94 (s, 1H), 4.57 (s, 2H), 4.30 (t, J = 7.0 Hz, 2H), 3.86 (s, 3H), 3.05 (t, J = 7.0 Hz, 2H); LC-MS: m/z 363.0 (M + 1)⁺. |
| 46 | 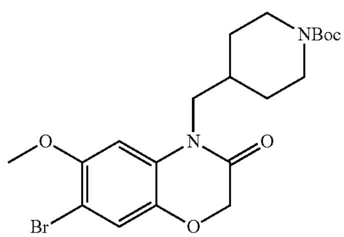 [SMILES: COc1cc2c(cc1Br)OCC(=O)N2CC1CCN(C(=O)OC(C)(C)C)CC1] | A | ¹H NMR (400 MHz, CDCl₃) δ 7.32 (s, 1H), 6.59 (s, 1H), 4.60 (s, 2H), 4.25-4.14 (m, 2H), 4.15-3.80 (m, 5H), 2.75-2.60 (m, 2H), 2.00-1.90 (m, 1H), 1.75-1.70 (m, 2H), 1.47 (s, 9H), 1.40-1.25 (m, 2H). |
| 47 | 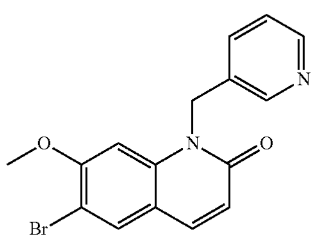 [SMILES: COc1cc2c(ccc(=O)n2Cc2cccnc2)cc1Br] | A | ¹H NMR (400 MHz, DMSO-d₆): δ 8.59 (d, J = 1.5 Hz, 1H), 8.46 (dd, J = 3.9 & 1.0 Hz, 1H), 8.04 (s, 1H), 7.90 (d, J = 8.1 Hz, 1H), 7.60 (d, J = 7.8 Hz, 1H), 7.35-7.32 (m, 1H), 6.99 (s, 1H), 6.60 (d, J = 9.8 Hz, 1H), 5.61 (s, 2H), 3.84 (s, 3H); LC-MS: m/z 346.0 (M + 1)⁺. |
| 48 | 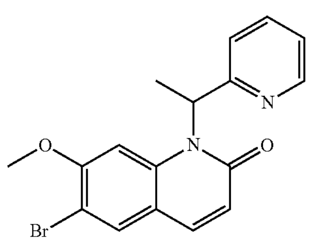 [SMILES: COc1cc2c(ccc(=O)n2C(C)c2ccccn2)cc1Br] | A | ¹H NMR (400 MHz, DMSO-d₆): δ 8.57-8.55 (m, 1H), 8.18-8.15 (m, 2H), 7.79-7.75 (m, 1H), 7.49 (d, J = 7.6 Hz, 1H), 7.32-7.27 (m, 1H), 7.18 (s, 1H), 6.99 (d, J = 8.8 Hz, 1H), 6.45-6.44 (m, 1H), 3.95 (s, 3H), 1.67 (d, J = 6.8 Hz, 3H); LC-MS: m/z 361.0 (M + 1)⁺. |
| 49 | 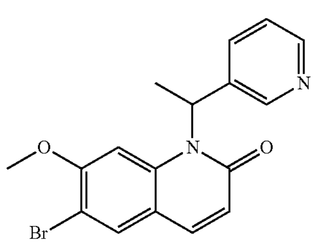 [SMILES: COc1cc2c(ccc(=O)n2C(C)c2cccnc2)cc1Br] | A | ¹H NMR (400 MHz, DMSO-d₆): δ 8.75 (s, 1H), 8.50-8.48 (m, 1H), 8.18-8.14 (m, 2H), 7.93-7.90 (m, 1H), 7.41-7.38 (m, 1H), 7.22 (s, 1H), 6.95 (d, J = 8.8 Hz, 1H), 6.48-6.42 (m, 1H), 3.97 (s, 3H), 1.68 (d, J = 6.4 Hz, 3H); LC-MS: m/z 359.0 (M + 1)⁺. |

| Int No. | Structure | Method | Characterization data |
|---|---|---|---|
| 50 | 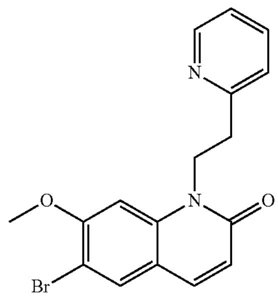 [SMILES: COc1cc2c(ccc(=O)n2CCc2ccccn2)cc1Br] | A | LC-MS: m/z 359.1 (M + 1)+. |
| 51 | 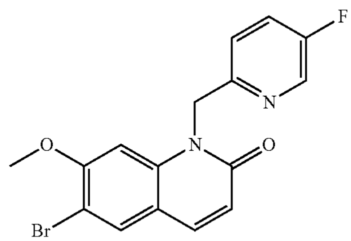 [SMILES: COc1cc2c(ccc(=O)n2Cc2ccc(F)cn2)cc1Br] | A | $^1$H NMR (400 MHz, DMSO-d$_6$): δ 8.49 (d, J = 3.0 Hz, 1H), 8.01 (s, 1H), 7.87 (d, J = 9.6 Hz, 1H), 7.72-7.67 (m, 1H), 7.42-7.38 (m, 1H), 7.07 (s, 1H), 6.57 (d, J = 9.6 Hz, 1H), 5.63 (s, 2H), 3.82 (s, 3H); LC-MS: m/z 365.0 (M + 1)+. |
| 52 | 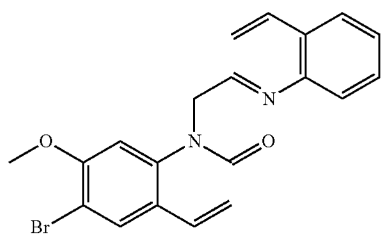 | A | $^1$H NMR (400 MHz, DMSO-d$_6$): δ 8.41 (d, J = 8.8 Hz, 1H), 8.23-8.21 (m, 2H), 8.01 (t, J = 9.3 Hz, 2H), 7.80-7.78 (m, 1H), 7.69 (d, J = 8.3 Hz, 1H), 7.63 (m, 1H), 7.27 (s, 1H), 7.08 (d, J = 8.8 Hz, 1H), 5.76 (s, 2H), 3.97 (s, 3H); LC-MS: m/z 395.0 (M + 1)+. |
| 53 | 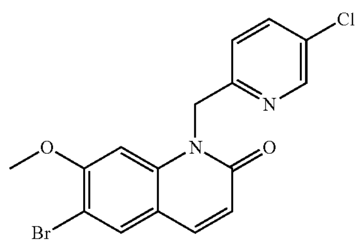 [SMILES: COc1cc2c(ccc(=O)n2Cc2ccc(Cl)cn2)cc1Br] | B | $^1$H NMR (400 MHz, DMSO-d$_6$): δ 8.50 (d, J = 2.5 Hz, 1H), 8.01 (s, 1H), 7.90-7.87 (m, 2H), 7.36 (d, J = 8.8 Hz, 1H), 7.04 (s, 1H), 6.57 (d, J = 9.8 Hz, 1H), 5.63 (s, 2H), 3.81 (s, 3H); LC-MS: m/z 380.1 (M + 1)+. |
| 54 | 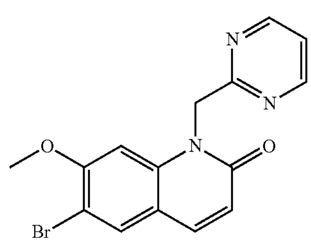 [SMILES: COc1cc2c(ccc(=O)n2Cc2ncccn2)cc1Br] | B | $^1$H NMR (400 MHz, DMSO-d$_6$): δ 8.74-8.73 (m, 1H), 8.02 (s, 2H), 7.86 (d, J = 9.2 Hz, 1H), 7.41-7.38 (m, 1H), 6.88 (s, 1H), 6.54 (d, J = 8.8 Hz, 1H), 5.73 (s, 2H), 3.75 (s, 3H); LC-MS: m/z 348.0 (M + 1)+. |
| 55 | 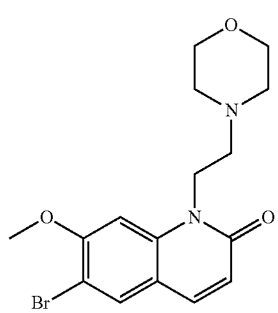 [SMILES: COc1cc2c(ccc(=O)n2CCN2CCOCC2)cc1Br] | B | ES-MS: m/z 367.1 (M + 1)+. |

| Int No. | Structure | Method | Characterization data |
|---|---|---|---|
| 56 | 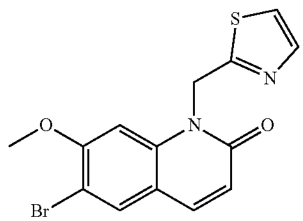 [SMILES: COc1cc2c(ccc(=O)n2Cc2nccs2)cc1Br] | B | LC-MS: m/z 353.0 (M + 1)+. |
| 57 | 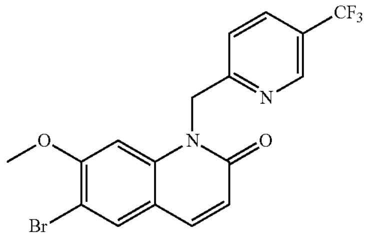 [SMILES: COc1cc2c(ccc(=O)n2Cc2ccc(C(F)(F)F)cn2)cc1Br] | B | $^1$H NMR (CDCl$_3$, 300 MHz): δ 8.82 (s, 1H), 7.85 (d, J = 7.2 Hz, 1H), 7.71 (s, 1H), 7.59 (d, J = 9.6 Hz, 1H), 7.47 (d, J = 8.1 Hz, 1H), 7.11 (s, 1H), 6.66 (d, J = 9.6 Hz, 1H), 5.71 (bs, 2H), 3.91 (s, 3H); LC-MS: m/z 414.8 (M + 1)+. |
| 58 | 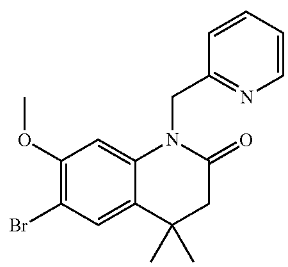 [SMILES: COc1cc2c(cc1Br)C(C)(C)CC(=O)N2Cc1ccccn1] | B | $^1$H NMR (400 MHz, DMSO-d$_6$): δ 8.50 (d, J = 7.2 Hz, 1H), 7.77-7.73 (m, 1H), 7.40 (s, 1H), 7.34-7.25 (m, 2H), 6.81 (s, 1H), 5.28 (s, 2H), 3.67 (s, 3H), 2.55 (s, 2H), 1.23 (s, 6H); LC-MS: m/z 377.1 (M + 1)+. |
| 59 | 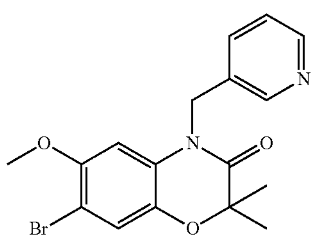 [SMILES: COc1cc2c(cc1Br)OC(C)(C)C(=O)N2Cc1cccnc1] | B | ES-MS: m/z 377.0 (M + 1)+. |
| 60 | 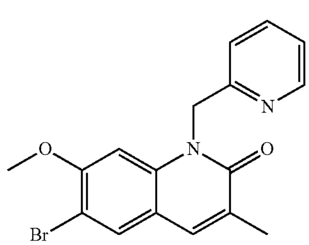 [SMILES: COc1cc2c(cc1Br)cc(C)c(=O)n2Cc1ccccn1] | B | $^1$H NMR (400 MHz, CDCl$_3$): δ 8.56 (d, J = 4.9 Hz, 1H), 7.63-7.58 (m, 2H), 7.46 (s, 1H), 7.26-7.24 (m, 1H), 7.20-7.18 (m, 1H), 7.12 (s, 1H), 5.68 (s, 2H), 3.86 (s, 3H), 2.29 (s, 3H); LC-MS: m/z 361.0 (M + 1)+. |
| 61 | 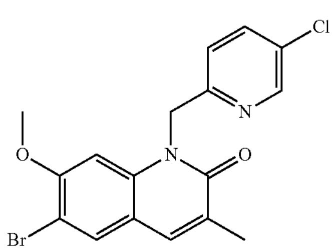 [SMILES: COc1cc2c(cc1Br)cc(C)c(=O)n2Cc1ccc(Cl)cn1] | B | $^1$H NMR (400 MHz, DMSO-d$_6$): δ 8.55 (d, J = 2.0 Hz, 1H), 7.91-7.87 (m, 2H), 7.75 (d, J = 1.0 Hz, 1H), 7.35 (d, J = 8.8 Hz, 1H), 7.02 (s, 1H), 5.65 (s, 2H), 3.80 (s, 3H), 2.13 (s, 3H); LC-MS: m/z 393.0 (M + 1)+. |

-continued

| Int No. | Structure | Method | Characterization data |
|---|---|---|---|
| 62 | (structure) | B | ¹H NMR (400 MHz, CDCl₃): δ 7.67 (s, 1H), 7.43 (s, 1H), 7.30-7.26 (m, 2H), 7.22 (d, J = 8.3 Hz, 2H), 6.66 (s, 1H), 4.45 (t, J = 7.9 Hz, 2H), 3.93 (s, 3H), 3.02 (t, J = 7.8 Hz, 2H), 2.24 (s, 3H); LC-MS: m/z 406.0 (M + 1)⁺. |
| 63 | (structure) | B | LC-MS: m/z 427.1 (M + H, 97.56%). |
| 64 | (structure) | B | LC-MS: m/z 429.1 (M + 2)²⁺. |
| 65 | (structure) | B | ¹H NMR (400 MHz, DMSO-d₆): δ 8.50 (d, J = 4.4 Hz, 1H), 7.92 (s, 1H), 7.79-7.75 (m, 1H), 7.39-7.37 (m, 1H), 7.31-7.28 (m, 1H), 6.90 (s, 1H), 5.38 (s, 2H), 3.80 (s, 3H), 2.40 (s, 6H); LC-MS: m/z 391.0 (M + 1)⁺. |
| 66 | (structure) | B | LC-MS: m/z 375.1 (M + 1)⁺. |

| Int No. | Structure | Method | Characterization data |
|---|---|---|---|
| 67 | 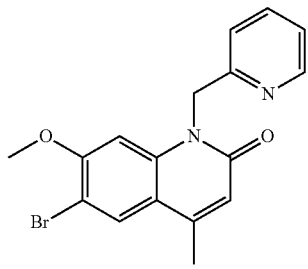 [SMILES: COc1cc2c(cc1Br)c(C)cc(=O)n2Cc1ccccn1] | B | $^1$H NMR (400 MHz, DMSO-d$_6$): δ 8.50 (d, J = 4.4 Hz, 1H), 7.92 (s, 1H), 7.76-7.72 (m, 1H), 7.29-7.24 (m, 2H), 7.07 (s, 1H), 6.50 (s, 1H), 5.61 (s, 2H), 3.78 (s, 3H), 2.42 (s, 3H); LC-MS: m/z 359.1 (M + 1)$^+$. |
| 68 | 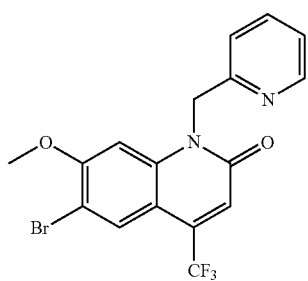 [SMILES: COc1cc2c(cc1Br)c(C(F)(F)F)cc(=O)n2Cc1ccccn1] | B | $^1$H NMR (400 MHz, DMSO-d$_6$): δ 8.49-8.48 (m, 1H), 7.81-7.77 (m, 2H), 7.42-7.40 (m, 1H), 7.31-7.29 (m, 1H), 7.22 (s, 1H), 7.10 (s, 1H), 5.71 (s, 2H), 3.84 (s, 3H); LC-MS: m/z 413.0 (M + 1)$^+$. |
| 69 | 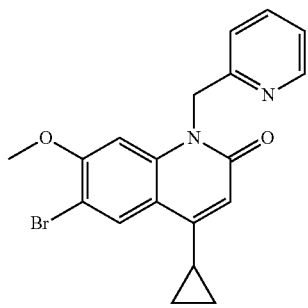 [SMILES: COc1cc2c(cc1Br)c(C1CC1)cc(=O)n2Cc1ccccn1] | B | $^1$H NMR (400 MHz, CDCl$_3$): δ 8.55 (d, J = 4.5 Hz, 1H), 8.18 (s, 1H), 7.59 (dt, J = 7.8, 1.8 Hz, 1H), 7.25 (s, 1H), 7.20-7.17 (m, 2H), 7.15 (s, 1H), 5.64 (bs, 2H), 3.87 (s, 3H), 2.10-2.00 (m, 1H), 1.23-1.07 (m, 2H), 0.83-0.78 (m, 2H); LC-MS: m/z 385.1 (M + 1)$^+$. |
| 70 | 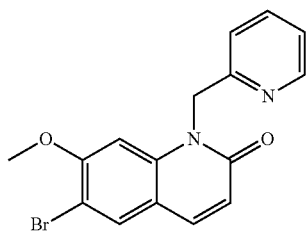 [SMILES: COc1cc2c(ccc(=O)n2Cc2ccccn2)cc1Br] | C | $^1$H NMR (400 MHz, DMSO-d$_6$): δ 8.49 (d, J = 4.4 Hz, 1H), 8.01 (s, 1H), 7.87 (d, J = 9.2 Hz, 1H), 7.78-7.77 (m, 1H), 7.29-7.26 (m, 2H), 7.08 (s, 1H), 6.58 (d, J = 9.2 Hz, 1H), 5.62 (s, 2H), 3.79 (s, 3H); MS (ES) m/e 347.0 (M + 2)$^{2+}$. |
| 71 | 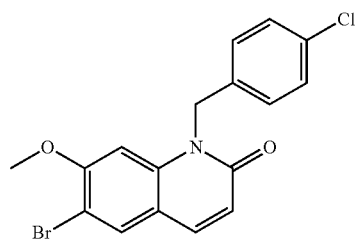 | C | $^1$HNMR 400 MHz (DMSO-d$_6$) δ 8.02 (s, 1H), 7.96 (S, 1H), 7.40-7.39 (m, 2H), 7.38-7.30 (m, 2H), 6.93 (S, 1H), 6.60 (d, J = 9.2 Hz, 1H), 5.56 (s, 2H), 3.82 (S, 3H); MS (LC) m/e 378.0 (M + 1)$^+$. |

Intermediate-72: Synthesis of tert-butyl 3,5-dimethyl-4-(4,4,5,5-tetramethyl-1,3,2-dioxaborolan-2-yl)-1H-pyrazole-1-carboxylate

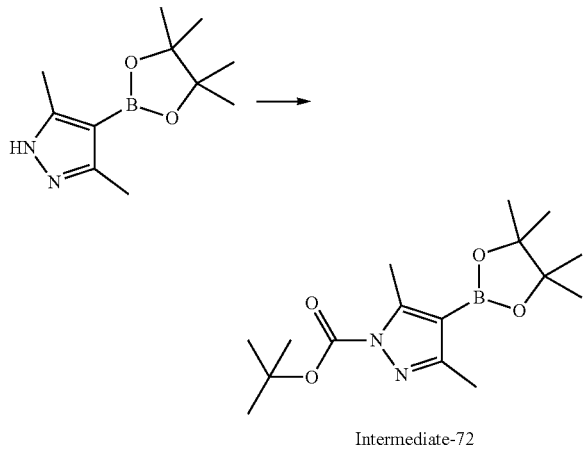

Intermediate-72

To a stirred solution of 3,5-dimethyl-4-(4,4,5,5-tetramethyl-1,3,2-dioxaborolan-2-yl)-1H-pyrazole (0.5 g, 2.25 mmol) in 1,4-dioxane (10.0 mL) and 2M $Na_2CO_3$ solution (2.5 mL) was added Boc-anhydride (0.62 mL, 2.70 mmol) and stirred at RT for 48 h. After completion of the reaction, the reaction mixture was diluted with EtOAc (200 mL), washed with water (100 mL), brine (50 mL), dried over sodium sulphate and concentrated. The residue was purified on silica gel (100-200 mesh) to isolate the title compound as off-white solid (0.45 g, 62%). $^1$H NMR (400 MHz, DMSO-$d_6$) δ 3.31 (s, 3H), 2.21 (s, 3H), 1.55 (s, 9H), 1.26 (s, 12H); LC-MS: m/z 323.2 (M+1)$^+$.

Intermediate-73: Synthesis of 3-bromo-1-(3,4-dimethoxybenzyl)-4-methyl-1H-pyrrole-2,5-dione

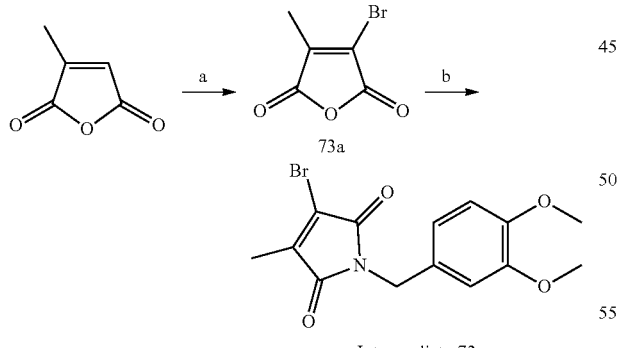

Intermediate-73

Step-a: Synthesis of 3-bromo-4-methylfuran-2,5-dione

A stirred mixture of 3-methyl-2,5-furandione (2.0 g, 17.85 mmol), $AlBr_3$ (0.11 g, 3.18 mmol) and $Br_2$ (1.6 mL. 71.4 mmol) was heated overnight at 120° C. Upon completion of reaction, the reaction mixture was cooled to RT and diluted with ethyl acetate (100 mL). The organic phase was washed with 0.1% HCl and brine. The organic phase were dried over anhydrous $Na_2SO_4$ and concentrated under reduced pressure to obtain crude compound, which was used in next step without any purification (3.20 g, crude). $^1$H NMR (300 MHz. $CDCl_3$): δ 2.21 (s, 3

Step-b: Synthesis of 3-bromo-1-(3,4-dimethoxybenzyl)-4-methyl-1H-pyrrole-2,5-dione A stirred solution of 3-bromo-4-methyl-2,5-furandione (1.0 g, 5.29 mmol) in acetic acid (10 mL) was treated with 1-[3,4-bis(methyloxy)phenyl]methanamine (0.8 g, 5.29 mmol) at RT. The resulting mixture was heated overnight at 100° C. Upon completion of the reaction (TLC), the reaction mixture was concentrated under reduced pressure. The obtained residue was taken in AcOH (20 mL) and AcONa (0.315 g, 4.23 mmol) was added to the above solution. The reaction mixture was refluxed for 2 h. The reaction mixture was cooled to RT and diluted with cold water, before extracting with DCM (3×50 mL). The combined organic phase was dried over anhydrous $Na_2SO_4$ and concentrated under reduced pressure. The obtained residue was purified by silica gel column chromatography (elution 10% EtOAc/hexanes) to give the title compound as off-white solid (1.0 g, 55.8%). $^1$H NMR (300 MHz, $CDCl_3$): δ 6.95-6.92 (m, 2H), 6.81-6.77 (m, 1H), 4.62 (s, 2H), 3.87 (s, 3H), 3.85 (s, 3H), 2.03 (s, 3H); LC-MS: m/z 341.8 (M+1)$^+$.

Intermediate-74: Synthesis of 3-cyclopropyl-5-methyl-4-(4,4,5,5-tetramethyl-1,3,2-dioxaborolan-2-yl)isoxazole

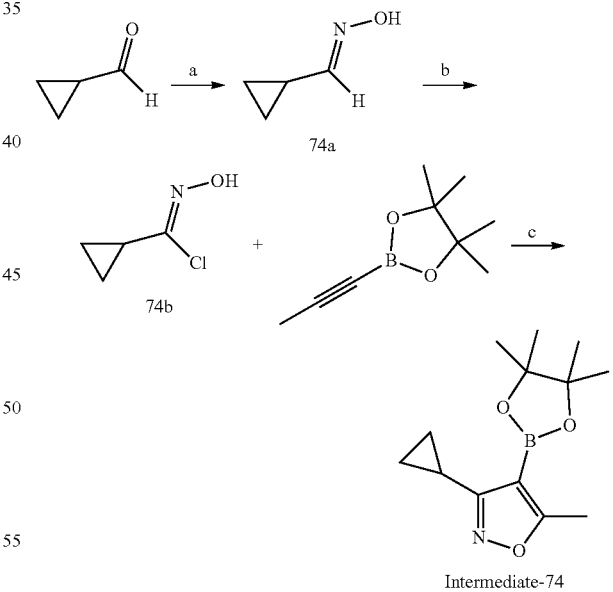

Intermediate-74

Intermediate-74

Step-a: Synthesis of cyclopropanecarbaldehydeoxime

To a stirred solution of hydroxylamine hydrochloride (3.0 g, 45 mmol) in water (10 mL) were added $Na_2CO_3$ (2.4 g, 18 mmol) and a solution of cyclopropanecarboxaldehyde (2.1 g, 30 mmol) in ethyl alcohol (9 mL) at RT. Then the reaction mixture was stirred at room temperature for 2 h and was extracted with ethyl acetate. The combined organic extracts were washed with brine, dried over anhydrous sodium sulfate and concentrated. The product was re-crystallized with hexane as white crystalline needles (2.20 g. 99%). $^1$H NMR (400 MHz, CDCl$_3$): δ 8.60 (bs, 1H), 6.03 (d, J=8.8 Hz, 1H), 2.31-2.27 (m, 1H), 0.97-0.83 (m, 2H), 0.65-0.61 (m, 2H): LC-MS: m/z 86.2 (M+1)$^+$.

Step-b: Synthesis of N-hydroxycyclopropanecarbimidoyl chloride

To a stirred solution of cyclopropanecarbaldehyde oxime (1.0 g. 11.75 mmol) in DMF (10 mL) maintained at RT, NCS (1.50 g, 27.74 mmol) was added under argon atmosphere at RT and stirred for 2 h. The reaction mixture was diluted with water and extracted with DCM (3×50 mL). The combined organic extract was washed with brine and concentrated under reduced pressure. The residue obtained was used in next step without further purification (1.00 g. crude): $^1$H NMR (400 MHz, CDCl$_3$): δ 9.92 (bs. 1H), 1.91-1.87 (m, 1H), 0.94-0.90 (m, 2H), 0.80-0.75 (m, 2

Step-c: Synthesis of 3-cyclopropyl-5-methyl-4-(4,4,5,5-tetramethyl-1,3,2-dioxaborolan-2-yl)isoxazole A stirred solution of N-hydroxycyclopropanecarbimidoyl chloride (0.5 g, 4.20 mmol) in DME (16 mL) was treated with 4,4,5,5-tetramethyl-2-(prop-1-yn-1-yl)-1,3,2-dioxaborolane (0.69 g. 4.2 mmol) and KHCO$_3$ (0.84 g, 8.4 mmol) at RT under a nitrogen atmosphere. The reaction mixture was heated at 50° C. for 12 h. The mixture was cooled to room temperature and filtered through celite pad. The filtrate was concentrated under reduced pressure. The obtained oily residue was purified by silica gel (100-200 mesh) column chromatography (using 10-20% EtOAc/Hexane as eluent) to give the title compound as a white solid (0.5 g); LC-MS: m/z 249.8 (M+1)$^+$.

Intermediate-75: Synthesis of 3-methyl-4-(4,4,5,5-tetramethyl-1,3,2-dioxaborolan-2-yl)-5-(trimethylsilyl)isoxazole Step-a: Synthesis of trimethyl((4,4,5,5-tetramethyl-1,3,2-dioxaborolan-2-yl)ethynyl)silane To a stirred solution of trimethylsilylacetylene (5.27 g, 53.76 mmol) in THF (100 mL) at −78° C., 2.5 M of n-BuLi in n-hexane (35.3 mL, 53.76 mmol) was added drop wise under nitrogen atmosphere. After 15 min, 2-isopropoxy-4,4,5,5-tetramethyl-1,3,2-dioxaborolane (10.0 g, 53.76 mmol) was slowly added and the reaction mixture was stirred at −78° C. After 2 h, the reaction mixture was allowed to warm to −30° C., and the p$^H$ was adjusted to 3 using anhydrous HCl. The reaction mixture was filtered, and the filtrate was distilled to give the title product (10.00 g, crude). $^1$H NMR (400 MHz, DMSO-d$_6$): δ 1.17 (s, 12H), 0.14 (s, 9

Step-b: Synthesis of 3-methyl-4-(4,4,5,5-tetramethyl-1,3,2-dioxaborolan-2-yl)-5-(trimethylsilyl)isoxazole A solution of chloroacetaldoxime (0.5 g, 4.62 mmol), trimethyl((4,4,5,5-tetramethyl-1,3,2-dioxaborolan-2-yl)ethynyl)silane (0.833 g, 3.73 mmol) and KHCO$_3$ (0.934 g, 9.35 mmol) in DME (16 mL) was heated at 50° C. for 12 h. After completion of the reaction, the reaction mixture was cooled to room temperature, solids were filtered through celite. The filtrate was concentrated under reduced pressure to give yellow oil, which was purified by flash column chromatography (10% EtOAc/Hexane as eluent) to give the title compound as a white solid (0.60 g, 45.5%). $^1$H NMR (CDCl$_3$, 300 MHz): δ2.40 (s, 3H), 1.31 (s, 12H), 0.37 (s, 9H); LC-MS: m/z 282.3 (M+1)$^+$.

Intermediate-76: Synthesis of 7-methoxy-1-(pyridin-2-ylmethyl)-6-(4,4,5,5-tetramethyl-1,3,2-dioxaborolan-2-yl)quinolin-2(1H)-one

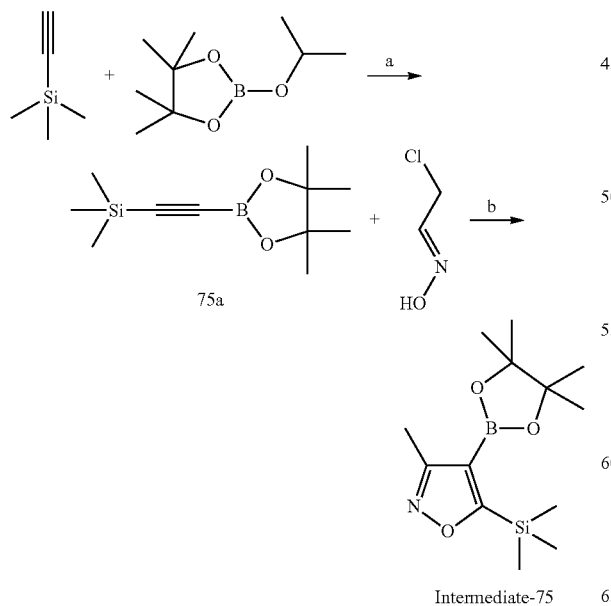

Intermediate-75

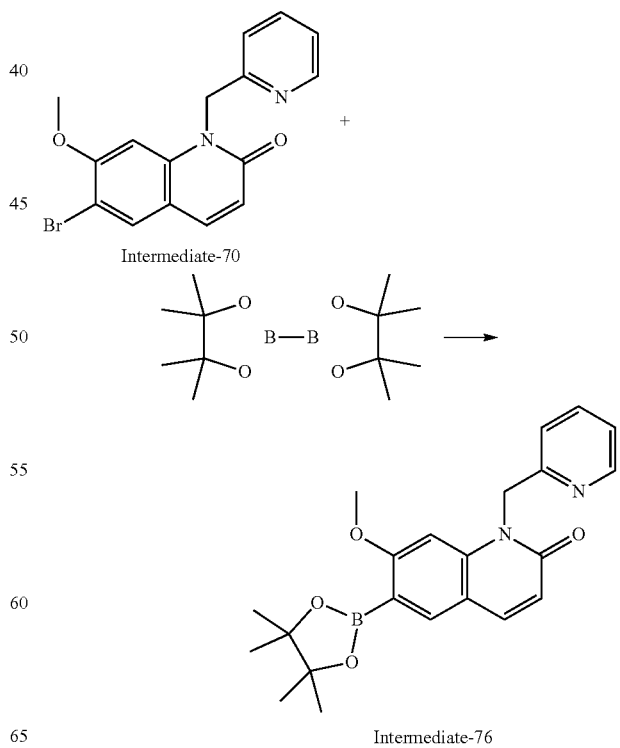

Intermediate-76

In a resealable reaction tube, to a solution of 6-bromo-7-methoxy-1-(pyridin-2-ylmethyl)quinolin-2(1H)-one (1.0 g, 2.90 mmol) in 1,4-dioxane, was added 4,4,4',4',5,5,5',5'-octamethyl-2,2'-bi(1,3,2-dioxaborolane) (1.1 g, 4.30 mmol), Pd(dppf)Cl$_2$.DCM (0.23 g, 0.29 mmol), and KOAc (0.85 g, 8.7 mmol) under nitrogen atmosphere. The solution was degassed with nitrogen gas for 15 min, later gradually heated to 100° C. and stirred at same temperature until the completion of reaction. The reaction mixture was cooled to room temperature, was diluted with cold water and extracted with ethyl acetate (3×30 mL). The combined organic layers were washed with brine and concentrated under reduced pressure. The residue obtained was purified by column chromatography (60-120 mesh, 50-100% EtOAc-hexanes as eluent) to yield the title compound as a pale brown solid (0.80 g, 70.7%). $^1$H NMR (400 MHz, DMSO-d$_6$): δ 8.50 (s, 1H), 7.94-7.90 (m, 2H), 7.78 (m, 1H), 7.3-7.19 (m, 2H), 6.87 (s, 1H), 6.56-6.45 (m, 1H), 5.60 (d, J=18.8 Hz, 2H), 3.93 (s, 3H), 1.26 (s, 12H): LC-MS: m/z 393.2 (M+1)$^+$.

Intermediate-77: Synthesis of 6-(3,5-dimethylisoxazol-4-yl)-7-methoxyquinoxalin-2(1H)-one

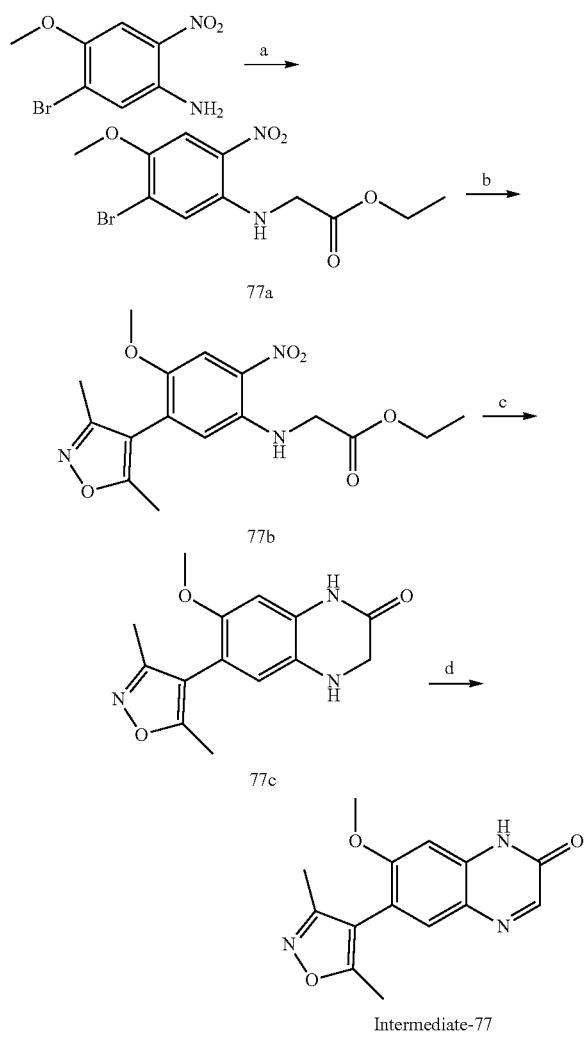

Intermediate-77

Step-a: Synthesis of ethyl 2-((5-bromo-4-methoxy-2-nitrophenyl)amino)acetate

To a suspension of 5-bromo-4-methoxy-2-nitroaniline (1 g, 4.0 mmol) in ethylbromo acetate (8 g, 4.7 mmol) was added K$_2$CO$_3$ (0.838 g, 6.1 mmol). The reaction mixture was heated to 150° C. and maintained for 3 h at same temperature. The reaction mixture was diluted with ethyl acetate and washed with water (50 mL×3) and dried over Na$_2$SO$_4$ and concentration. The obtained residue was purified by column chromatography on silica (2-5% EtOAc in hexane) to give the desired product as an off white solid (0.600 g, 45%). $^1$HNMR (400 MHz, DMSO-d$_6$) δ 8.25 (bs, 1H), 7.63 (s, 1H), 7.32 (s, 1H), 4.29 (d, J=6.0 Hz, 2H), 4.17 (q, J=7.0 Hz, 2H), 3.84 (s, 3H), 1.22 (t, J=7.0 Hz, 3H). MS (ES) m/e 333.1 (M+1)$^+$.

Step-b: Synthesis of ethyl 2-((5-(3,5-dimethylisoxazol-4-yl)-4-methoxy-2-nitrophenyl)amino) acetate To a stirred solution of ethyl 2-((5-bromo-4-methoxy-2-nitrophenyl) amino) acetate (1 g, 3.0 mmol) in 10 mL of 1,4-Dioxane:H$_2$O (7:3) was added 3,5-dimethylisoxazole-4-boronic acid (0.847 g, 6.0 mmol), K$_2$CO$_3$ (1.243 g, 9.0 mmol), followed by Pd(PPh$_3$)$_2$Cl$_2$ (0.210 g, 0.3 mmol). The reaction mixture was heated to 100° C. and maintained for 1.5 h at same temperature. Then allowed to RT and reaction mixture was diluted with ethyl acetate and washed with water (50 mL×3), dried over Na$_2$SO$_4$ and concentration to gave the desired product as a white solid (0.7 g, 67%); MS (ES) m/e 350.2 (M+1)$^+$.

Step-c: Synthesis of 6-(3,5-dimethylisoxazol-4-yl)-7-methoxy-3,4-dihydroquinoxalin-2(1H)-one A stirred solution of ethyl 2-((5-(3,5-dimethylisoxazol-4-yl)-4-methoxy-2-nitrophenyl) amino)acetate (0.07 g, 2.0057 mmol) in 10 mL of ethanol was added SnCl$_2$.2H$_2$O (2.25 g, 10.028 mmol). The reaction mixture was heated to reflux and maintained for 1 h. The reaction mixture was basified with aq. Na$_2$CO$_3$, extracted with ethyl acetate and dried under reduced pressure to afford the title compound (0.500 g, 97%) as pale brown solid. $^1$HNMR (400 MHz, DMSO-d$_6$) δ 12.4 (bs, 1H), 10.3 (s, 1H), 8.03 (s, 1H), 7.64 (s, 1H), 3.85 (s, 3H), 3.63 (s, 2H), 2.28 (s, 3H), 2.23 (s, 3H). MS (ES) m/e 274.2 (M+1)$^+$.

Step-d: Synthesis of 6-(3,5-dimethylisoxazol-4-yl)-7-methoxyquinoxalin-2(1H)-one A stirred solution of 6-(3,5-dimethylisoxazol-4-yl)-7-methoxy-3,4-dihydroquinoxalin-2(1H)-one (0.200 g, 0.7782 mmol) in 8% NaOH (2.64 mL) solution was added 30% H$_2$O$_2$(2.34 mL) at room temperature. The reaction mixture was heated to 80° C. and maintained for 4 h at same temperature. The reaction mixture was cooled and acetic acid (0.3 mL) was added drop wise. The suspension was stirred over night at room temperature and the precipitated solid was collected by filtration to afford the title compound as an off white solid (0.117 g, 59%). $^1$HNMR (400 MHz, DMSO-d$_6$) δ 12.4 (s, 1H), 8.03 (s, 1H), 7.64 (s, 1H), 6.90 (s, 1H), 3.85 (s, 3H), 2.27 (s, 3H), 2.08 (s, 3H). MS (ES) m/e 272.1 (M+1)$^+$.

Intermediate-78: Synthesis of 6-(3,5-dimethylisoxazol-4-yl)-7-methoxy-2-oxo-1-(pyridin-2-ylmethyl)-1,2-dihydroquinoline-3-carbaldehyde

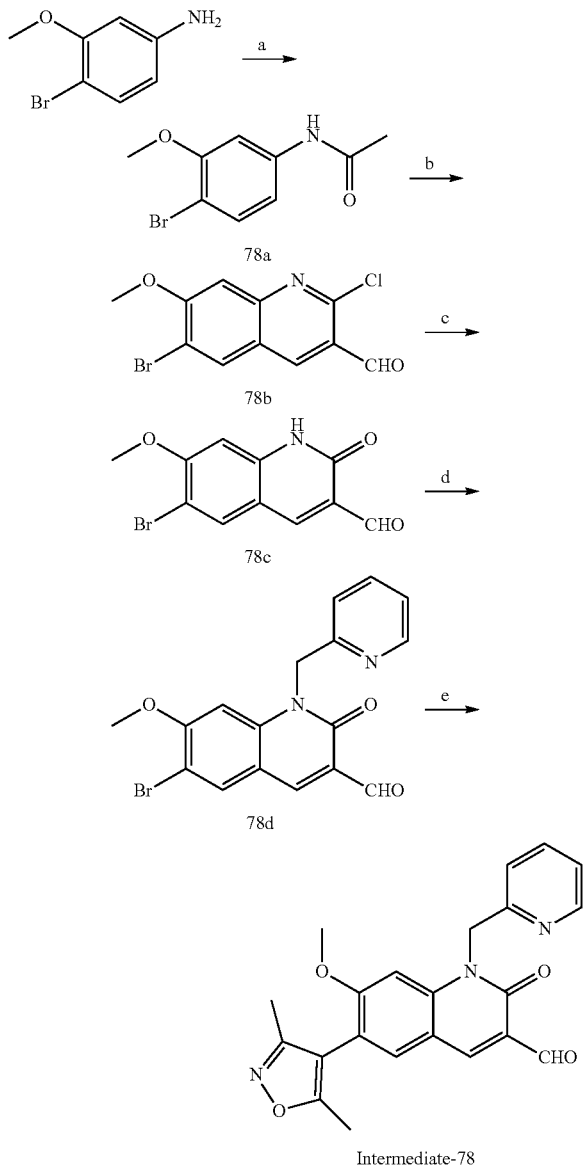

Intermediate-78

Step-a: Synthesis of N-(4-bromo-3-methoxyphenyl)acetamide

To an ice-cooled solution of 4-bromo-3-methoxyaniline (2.0 g, 9.90 mmol) in DCM (25 mL) was added triethylamine (4.1 mL, 29.7 mmol), after stirred for 5 min, acetyl chloride (1.05 mL, 14.85 mmol) was added. After completion of reaction, the reaction mixture was quenched with aq. NaHCO$_3$ solution (up to pH~8) extracted with DCM (200 mL×2). The combined organic layers were washed with water (200 mL), brine (200 mL), dried over sodium sulphate and concentrated. The residue was directly used for the next step without further purification (2.5 g). $^1$H NMR (400 MHz, DMSO-d$_6$) δ 10.06 (s, 1H), 7.45-7.43 (m, 2H), 7.10 (dd, J$_1$=2.0 Hz, J$_2$=8.3 Hz, 1H), 3.79 (s, 3H), 2.04 (s, 3H); LC-MS: m/z 244.1 (M+1)$^+$.

Step-b: Synthesis of 6-bromo-2-chloro-7-methoxyquinoline-3-carbaldehyde

POCl$_3$ (7.6 mL, 81.96 mmol) was added drop wise to DMF (2.5 mL, 32.78 mmol) at 0° C., after stirred for 5 min, N-(4-bromo-3-methoxyphenyl) acetamide (2.0 g, 8.19 mmol) was added and resulting solution was heated to 80° C. for 6 h. The reaction mixture was cooled to room temperature and poured into crushed ice and extracted with EtOAc (200 mL×2) twice. The combined organic layers were washed with water (200 mL), brine (200 mL), dried over sodium sulphate and concentrated. The residue was directly used for the next step without further purification (2.0 g). $^1$H NMR (400 MHz, DMSO-d$_6$) δ 10.33 (s, 1H), 8.88 (s, 1H), 8.64 (s, 1H), 7.59 (s, 1H), 4.07 (s, 3H); LC-MS: m/z 300 (M+1)$^+$.

Step-c: Synthesis of 6-bromo-7-methoxy-2-oxo-1,2-dihydroquinoline-3-carbaldehyde A suspension of 6-bromo-2-chloro-7-methoxyquinoline-3-carbaldehyde (2.0 g, 6.65 mmol) in 70% acetic acid (40 mL) was heated to reflux for 6 h. Upon cooling the reaction mixture to room temperature a solid product was precipitated out which was filtered and washed with water and dried invacuo to afford the title compound as brown solid (1.5 g, 80%). $^1$H NMR (400 MHz, DMSO-d$_6$) δ 12.18 (s, 1H), 10.17 (s, 1H), 8.42 (s, 1H), 8.22 (s, 1H), 6.93 (s, 1H), 3.94 (s, 3H); LC-MS: m/n 284 (M+1)$^+$.

Step-d: Synthesis of 6-bromo-7-methoxy-2-oxo-1-(pyridin-2-ylmethyl)-1,2-dihydroquinoline-3-carbaldehyde To a solution of 6-bromo-7-methoxy-2-oxo-1,2-dihydroquinoline-3-carbaldehyde (9 g, 31.91 mmol) in DMF (80 mL) were added potassium carbonate (13.2 g. 95.73 mmol) followed by 2-(chloromethyl) pyridine hydrochloride (6.4 g, 35.1 mmol) and stirred at 80° C. for 16 h. After completion of reaction, the reaction mixture was diluted with water and extracted with EtOAc (400 mL×2). The combined organic layers were washed with water (400 mL), brine (300 mL), dried over sodium sulphate and concentrated. The residue was directly used for the next step without further purification (7.5 g, 63%). $^1$H NMR (400 MHz, DMSO-d$_6$) δ 10.25 (s, 1H), 8.51-8.48 (m, 2H), 8.31 (s, 1H), 7.78 (t, J=7.9 Hz, 1H), 7.40 (d, J=8.4 Hz, 1H), 7.31-7.28 (m, 1H), 7.13 (s, 1H), 5.70 (s, 2H), 3.86 (s, 3H); LC-MS: m/z 373.0 (M)$^+$.

Step-e: Synthesis of 6-(3,5-dimethylisoxazol-4-yl)-7-methoxy-2-oxo-1-(pyridin-2-ylmethyl)-1,2-dihydroquinoline-3-carbaldehyde To a stirred solution of 6-bromo-7-methoxy-2-oxo-1-(pyridin-2-ylmethyl)-1,2-dihydroquinoline-3-carbaldehyde (4.0 g, 10.72 mmol) in 1,4-dioxane (40 mL) and H$_2$O (10 mL) were added 3,5-dimethylisoxazoleboronic acid (2.30 g. 16.08 mmol), sodium carbonate (3.41 g, 32.16 mmol) and degassed with nitrogen purging for 20 min. Then tetrakis triphenylphosphine palladium (2.47 g, 2.14 mmol) was added and heated at 100° C. for 8 h. After completion of reaction, the reaction mixture was concentrated and the residue was diluted with EtOAc (200 ml), washed with water (200 mL), brine (200 mL), dried over sodium sulphate and concentrated. The residue was washed with hexane to give title compound as yellow solid (3.2 g, 76%). $^1$H NMR (400 MHz, DMSO-$d_6$) δ 10.28 (s, 1H), 8.54 (s, 1H), 8.52 (d, J=4.4 Hz, 1H), 7.94 (s, 1H), 7.82-7.77 (m, 1H), 7.44 (d, J=7.8 Hz, 1H), 7.33-7.29 (m, 1H), 7.17 (s, 1H), 5.72 (s, 2H), 3.81 (s, 3H), 2.27 (s, 3H), 208 (s, 3H); LC-MS: m/z 390.1 (M+1)$^+$.

Intermediate-79: Synthesis of 6-(3,5-dimethyl-4H-1,2,4-triazol-4-yl)-7-methoxyquinolin-2(1H)-one

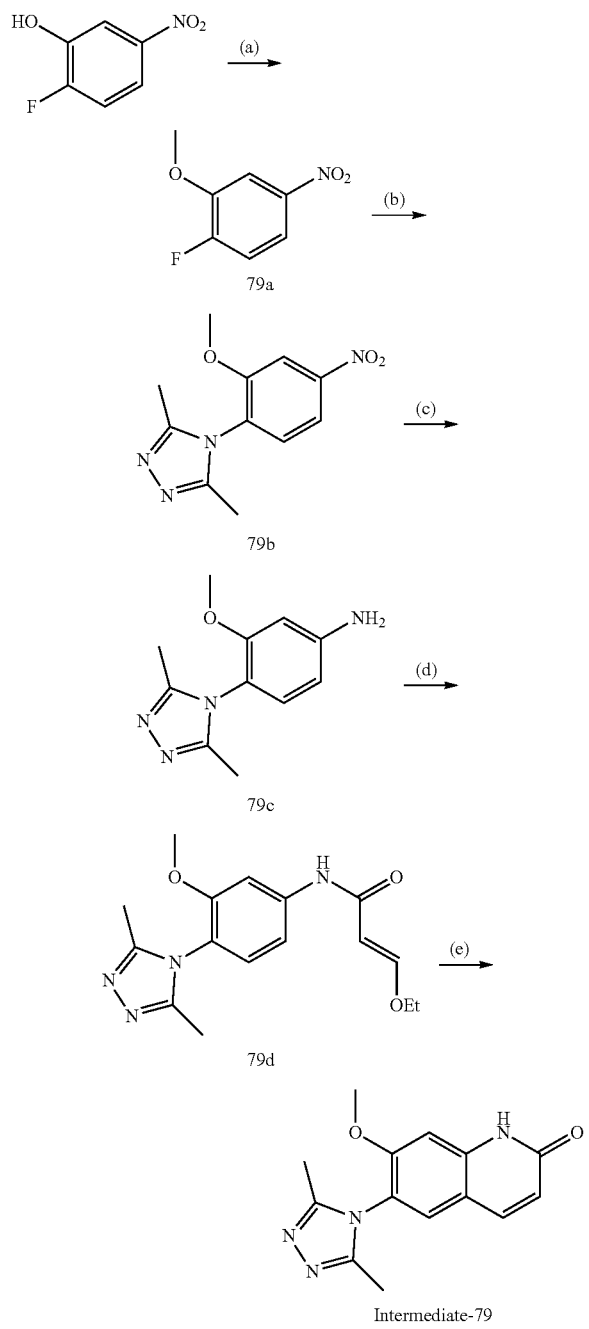

Step-a: Synthesis of 1-fluoro-2-methoxy-4-nitrobenzene

To a solution of 2-fluoro-5-nitrophenol (5.0 g, 31.84 mmol) in DMF (50 mL) was added $K_2CO_3$ (5.27 g, 38.1 mmol), after stirring at room temperature for 15 min was added methyl iodide (3 mL, 47.7 mmol) and the reaction mixture stirred at room temperature for 2 h. Reaction mixture was poured into ice water, separated solids were filtered, washed the solid thoroughly with water and vacuum dried to afford an off white solid (4.0 g, 73.5%). $^1$H NMR (300 MHz, CDCl3) 7.89-7.84 (m, 2H), 7.25-7.17 (m, 1H), 3.98 (s, 3H).

Step-b: Synthesis of 4-(2-methoxy-4-nitrophenyl)-3,5-dimethyl-4H-1,2,4-triazole

To a solution of 3,5-dimethyl-4H-1,2,4-triazole (0.44 g, 4.49 mmol) in DMF (10 mL) was added NaH (60%)(0.33 g, 8.18 mmol), after stirring at room temperature for 15 min, was added 1-fluoro-2-methoxy-4-nitrobenzene (0.7 g, 4.09 mmol) and heated at 80° C. for 3 h. The reaction mixture diluted with cold water and extracted with ethyl acetate (100 mL), and washed with water (50 mL), brine (50 mL), dried over sodium sulphate and concentrated invacuo to afford yellow oil which was used further step without purification (0.8 g); LC-MS: m/z 249.0 (M+H).

Step-c: Synthesis of 4-(3,5-dimethyl-4H-1,2,4-triazol-4-yl)-3-methoxyaniline

In a 50 mL round bottom flask, a stirred solution of 4-(2-methoxy-4-nitrophenyl)-3,5-dimethyl-4H-1,2,4-triazole (800 mg, 3.22 mmol) in Ethanol (20 mL) was added Fe powder (1.26 g, 22.5 mmol) and $NH_4Cl$ (1.2 g, 22.5 mmol) the reaction mixture and heated at 90° C. for 2 h. After completion of the reaction, the reaction mixture was diluted with ethyl acetate and filtered over celite bed and bed was washed with ethyl acetate (2×50 mL). The filtrate was washed sequentially with water, dried over Na2SO4 and concentrated to give title compound as a brown color solid. The crude product was taken to next step without any purification. (600 mg, crude). LC-MS m/z: 219.1 (M+1)$^+$.

Step-d: Synthesis of (E)-N-(4-(3,5-dimethyl-4H-1,2,4-triazol-4-yl)-3-methoxyphenyl)-3-ethoxyacrylamide The process of this step was adopted from step-b of intermediate-2. LC-MS: m/z 317.0 (M+1)$^+$.

Step-e: Synthesis of 6-(3,5-dimethyl-4H-1,2,4-triazol-4-yl)-7-methoxyquinolin-2(1H)-one The process of this step was adopted from intermediate-2 of step-c. LC-MS: m/z 271.1 (M+1)$^+$.

The present invention is further exemplified, but not limited, by the following examples that illustrate the preparation of compounds according to the invention.

Example-I: Synthesis of 4-(4-chlorobenzyl)-7-(3,5-dimethylisoxazol-4-yl)-6-methoxy-3,4-dihydro-2H-benzo[b][1,4]oxazine (Compound-1)

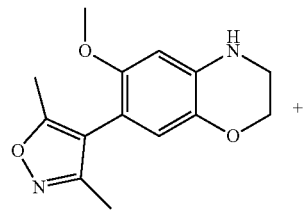

Intermediate-1

+

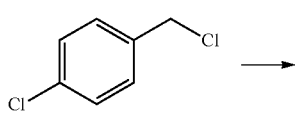

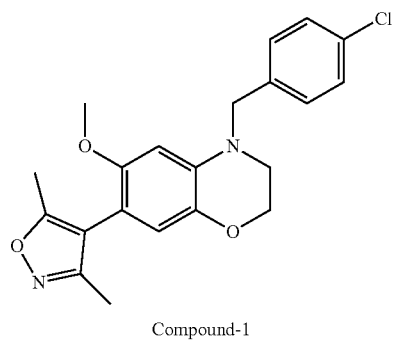

Compound-1

To a solution of intermediate-1 (0.04 g, 0.15 mmol) in DMF (5 mL) were added $K_2CO_3$ (0.064 g, 0.46 mmol), 4-chloro benzyl bromide (0.038 g. 0.18 mmol), and stirred at RT for 24 h. After completion of the reaction, the reaction mixture was diluted with EtOAC (50 mL), washed with water (50 mL), brine (50 mL), dried over sodium sulphate and concentrated. The residue was purified on preparative TLC plate to afford the title product as off-white semisolid (0.010 g, 72%). $^1$H NMR (400 MHz, DMSO-$d_6$): δ 7.44-7.39 (m, 4H), 6.53 (s, 1H), 6.39 (s, 1H), 4.55 (s, 2H), 4.17 (t, J=4.4 Hz, 2H), 3.55 (s, 3H), 3.40 (s, 2H), 2.19 (s, 3H), 2.02 (s, 3H); ES-MS: m/z 385.2 (M+1)$^+$.

The below compounds were prepared using the procedure similar to that for Compound-1 (Example-I).

| Compound No. | Structure | Characterization data |
|---|---|---|
| 2 | 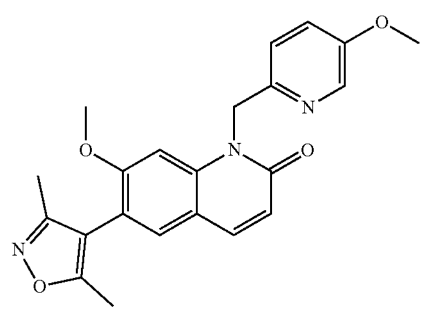 [SMILES: COc1ccc(Cn2c(=O)ccc3cc(-c4c(C)noc4C)c(OC)cc32)nc1] | $^1$H NMR (400 MHz, DMSO-$d_6$): δ 8.24 (d, J = 2.9 Hz, 1H), 7.88 (d, J = 9.8 Hz, 1H), 7.60 (s, 1H), 7.39-7.36 (m, 1H), 7.31-7.29 (m, 1H), 7.22 (s, 1H), 6.57 (d, J = 9.3 Hz, 1H), 5.57 (s, 2H), 3.79 (s, 3H), 3.78 (s, 3H), 2.24 (s, 3H), 2.05 (s, 3H); LC-MS: m/z 392.1 (M + 1)$^+$ |
| 3 | 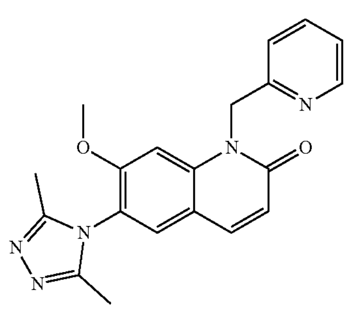 [SMILES: COc1cc2c(ccc(=O)n2Cc2ccccn2)cc1-n1c(C)nnc1C] | 1H NMR (300 MHz, CDCl3): 8.63 (m, 1H), 8.03-7.96 (m, 2H) 7.86 (s, 1H), 7.52-7.49 (m, 2H), 7.26 (s, 1H), 6.74 (d, J = 9.6 Hz, 1H), 5.83 (s, 2H), 3.85 (s, 3H), 2.43 (s, 3H), 2.36 (s, 3H); LC-MS; m/z 362.0 (M + 1)$^+$. |

Example-II: Synthesis of 1-(4-chlorobenzyl)-6-(3,5-dimethylisoxazol-4-yl)-7-methoxy quinoxalin-2(1H)-one (Compound-4)

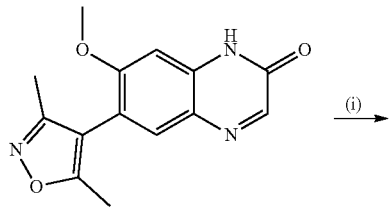

Intermediate-77

(i)

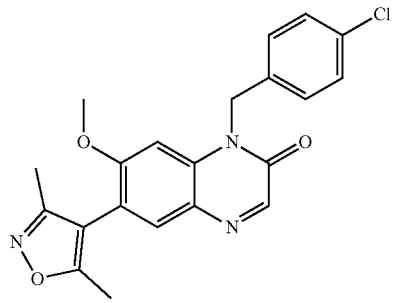

Compound-4

To a stirred solution of 6-(3,5-dimethylisoxazol-4-yl)-7-methoxyquinoxalin-2(1H)-one (0.117 g, 0.4317 mmol) in 2 mL of DMF at 0° C. was added 60% NaH (0.025 g, 1.0869 mmol), followed by 4-chlorobenzylbromide (0.098 g, 0.4780 mmol). Then the reaction mixture was allowed to stir for 1 h at room temperature. After completion of reaction, the reaction mixture was quenched with methanol and diluted with ethyl acetate and water. Layers were separated, washed with water (50 mL×3), dried over $Na_2SO_4$ and concentration. The obtained crude was purified by column chromatography on silica (2% MeOH in DCM) to give the desired product as an off white solid (0.017 g, 11%). $^1$HNMR (400 MHz, DMSO-$d_6$) δ 8.21 (s, 1H), 7.72 (s, 1H), 7.43 (s, 4H), 7.01 (s, 1H), 5.56 (s, 2H), 3.81 (s, 3H), 2.25 (s, 3H), 2.06 (s, 3H); MS (ES) m/z 396.1 (M+1)$^+$.

Example-III: Synthesis of 1-(4-chlorobenzyl)-6-(3,5-dimethylisoxazol-4-yl)-7-methoxy-3,4-dihydroquinolin-2(1H)-one (Compound-5)

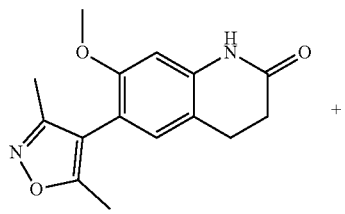

Intermediate-14

+

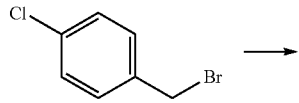

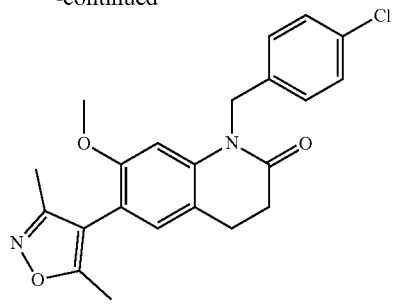

Compound-5

To a stirred suspension of 6-(3,5-dimethylisoxazol-4-yl)-7-methoxy-3,4-dihydroquinolin-2(1H)-one (0.180 g, 0.629 mmol) in DMF (8 mL) was added potassium t-butoxide (0.140 g, 1.25 mmol). The resulting mixture was refluxed for 2 h, was cooled to 0° C. and 1-(bromo methyl)-4-chlorobenzene (0.194 g, 0.94 mmol) and KI (0.005 g, 0.031 mmol) were added. Subsequently, the reaction mixture was refluxed for 12 h, diluted with ethyl acetate and washed with water (50 mL), dried over $Na_2SO_4$ and concentration under reduced pressure, followed by chromatography on silica gel (10% EtOAc in hexane) to give the desired product as a white solid (0.020 g, 8%): $^1$H NMR (400 MHz DMSO-$d_6$) δ 7.41-7.34 (m, 4H), 7.07 (s, 1H), 6.64 (s, 1H), 5.21 (s, 2H), 3.59 (s, 3H), 2.89 (t, J=7.2 Hz, 2H), 2.20 (t, J=7.1 Hz, 2H), 2.21 (s, 3H), 2.03 (s, 3H). MS (ES) m/e 397.3 (M+1)$^+$.

Example-IV: Synthesis of 4-(1-(4-chlorophenyl)ethyl)-7-(3,5-dimethylisoxazol-4-yl)-6-methoxy-1,3,4-dihydro-2H-benzo[b][1,4]oxazine (Compound-6)

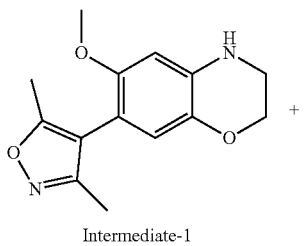

Intermediate-1

+

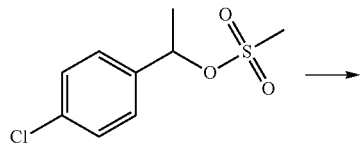

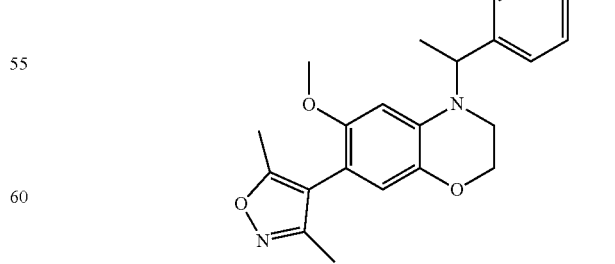

Compound-6

To a solution of intermediate-1 (0.020 g, 0.076 mmol) in $CH_3CN$ (10 mL) were added $Cs_2CO_3$ (0.050 g, 0.15 mmol), benzyltriethylammoniumchloride (0.017 mg, 0.007 mmol) followed by 1-(4-chlorophenyl)ethylmethanesulfonate (0.018 g, 0.076 mmol), and stirred at 65° C. for 16 h. After completion of reaction, the reaction mixture was diluted with EtOAC (50 mL), washed with water (50 mL), brine (50 mL), dried over sodium sulphate and concentrated. The residue was purified on preparative HPLC plate to afford the title product as brown solid (0.003 g, 11%). $^1$H NMR (400 MHz, DMSO-$d_6$): δ 7.50-7.30 (m, 4H), 6.53 (s, 1H), 6.52 (s, 1H), 5.22-5.18 (m, 1H), 4.18-3.95 (m, 2H), 3.60 (s, 3H), 3.35-3.28 (m, 1H), 3.15-3.05 (m, 1H), 2.20 (s, 3H), 1.98 (s, 3H), 1.53 (d, J=6.8 Hz, 3H); LC-MS: m/z 399.2 (M+1)$^+$.

The below compounds were prepared according to the above protocol by using the given starting intermediate and reactant at suitable reaction conditions.

| Compound No. | Structure | Characterization data |
|---|---|---|
| 7 | 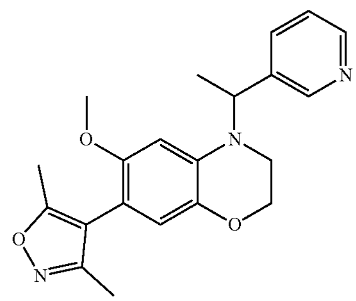 [SMILES: COc1cc2c(cc1-c1c(C)noc1C)OCCN2C(C)c1cccnc1] | $^1$H NMR (400 MHz, CDCl$_3$): δ 8.68 (s, 1H), 8.56 (d, J = 4.4 Hz, 1H), 7.71 (d, J = 7.6 Hz, 1H), 7.34-30 (m, 1H), 6.58 (s, 1H), 6.39 (s, 1H), 5.20-5.10 (m, 1H), 4.22-4.17 (m, 2H), 3.63 (s, 3H), 3.40-3.25 (m, 1H), 3.18-3.05 (m, 1H), 2.30 (s, 3H), 2.17 (s, 3H), 1.66 (d, J = 6.8 Hz, 3H); LC-MS: m/z 366.2 (M + 1)$^+$. |
| 8 | 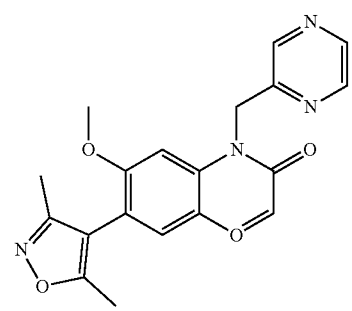 | $^1$H NMR (400 MHz, DMSO-$d_6$): δ 8.74 (s, 1H), 8.56 (s, 2H), 7.91 (d, J = 9.3 Hz, 1H), 7.63 (s, 1H), 7.12 (s, 1H), 6.56 (d, J = 9.3 Hz, 1H), 5.74 (s, 2H), 3.77 (s, 3H), 2.25 (s, 3H), 2.06 (s, 3H); LC-MS: m/z 363.2 (M + 1)$^+$. |
| 9 | 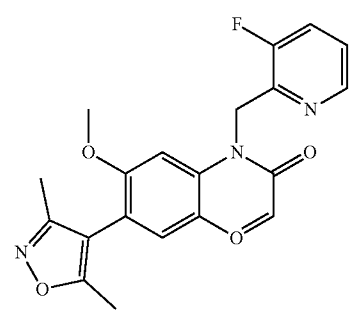 | $^1$H NMR (400 MHz, DMSO-$d_6$): δ 8.27 (d, J = 4.4 Hz, 1H), 7.89 (d, J = 9.2 Hz 1H), 7.80-7.60 (m, 1H), 7.62 (s, 1H), 7.41-7.39 (m, 1H), 7.03 (s, 1H), 6.52 (d, J = 9.2 Hz, 1H), 5.74 (s, 2H), 3.74 (s, 3H), 2.26 (s, 3H), 2.07 (s, 3H); LC-MS: m/z 380.2 (M + 1)$^+$. |
| 10* | 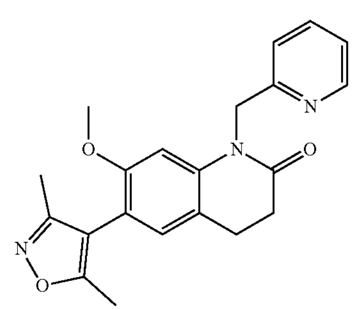 [SMILES: COc1cc2c(cc1-c1c(C)noc1C)CCC(=O)N2Cc1ccccn1] | $^1$H NMR (400 MHz, DMSO-$d_6$): δ 8.54-8.53 (m, 1H), 7.78-7.76 (m, 1H), 7.33-7.27 (m, 2H), 7.07 (s, 1H), 6.78 (s, 1H), 5.25 (s, 2H), 3.57 (s, 3H), 2.92-2.88 (m, 2H), 2.70-2.67 (m, 2H), 2.21 (s, 3H), 2.03 (s, 3H); LC-MS: m/z 364.2 (M + 1)$^+$. |

*Compound-10 was prepared from intermediate-14 and 2-(chloromethyl)pyridine hydrochloride using the procedure similar to the one depicted for Compound-6 (Example-IV).

Example-V: Synthesis of 4-((3-chlorophenyl) sulfonyl)-7-(3,5-dimethylisoxazol-4-yl)-6-methoxy-3,4-dihydro-2H-benzo[b][1,4]oxazine (Compound-11)

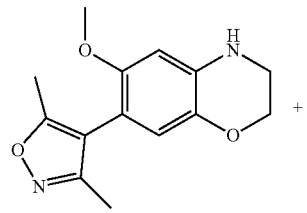

Intermediate-1

+

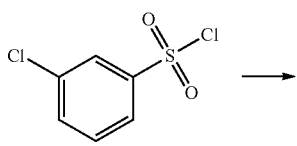

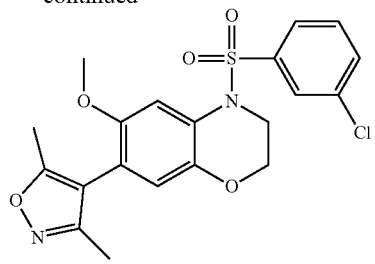

Compound-11

To a solution of 3-chlorobenzene-1-sulfonyl chloride (0.052 g, 0.25 mmol) in DCM (3 mL) were added pyridine (0.03 mL, 0.38 mmol) followed by intermediate-1 (0.050 g, 0.19 mmol), and stirred at RT for 5 h. After completion of reaction, the reaction mixture was diluted with EtOAc (50 mL), washed with water (50 mL), brine (50 mL), dried over sodium sulphate and concentrated. The residue was purified on preparative TLC plate to afford the title product (0.020 g, 24%). $^1$H NMR (400 MHz, DMSO-$d_6$): δ 7.83-7.80 (m, 1H), 7.75-7.63 ( m, 3H), 7.38 (s, 1H), 6.77 (s, 1H), 3.98-3.95 ( m, 2H), 3.78-3.74 (m, 2H), 3.74 (s, 3H), 2.23 (s, 3H), 2.05 (s, 3H); LC-MS: m/z 435.1 (M+1)$^+$.

The below compounds were prepared according to the above protocol by using the given 1) starting intermediate and reactant at suitable reaction conditions.

| Compound No. | Structure | Characterization data |
|---|---|---|
| 12 | 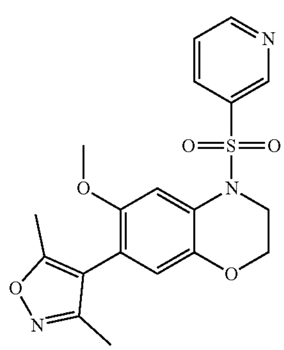 [SMILES: COc1cc2c(cc1-c1c(C)noc1C)OCCN2S(=O)(=O)c1cccnc1] | $^1$H NMR (400 MHz, DMSO-$d_6$): δ 8.96 (d, J = 2.0 Hz, 1H), 8.89-8.88 (m, 1H), 8.20 (d, J = 8.4 Hz, 1H), 7.69-7.65 (m, 1H), 7.40 (s, 1H), 6.76 (s, 1H), 4.01-3.99 (m, 2H), 3.81-3.79 (m, 2H), 3.75 (s, 3H), 2.23 (s, 3H), 1.99 (s, 3H); LC-MS: m/z 402.1 (M + 1)$^+$. |
| 13 | 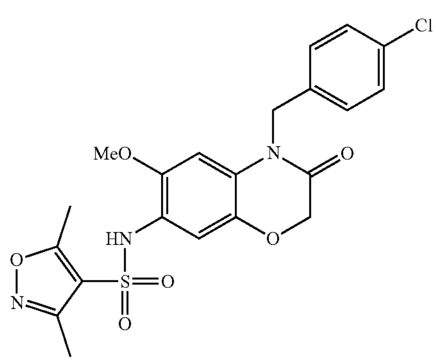 [SMILES: COc1cc2c(cc1NS(=O)(=O)c1c(C)noc1C)OCC(=O)N2Cc1ccc(Cl)cc1] | $^1$H NMR (400 MHz, DMSO-$d_6$): δ 9.74 (bs, 1H). 7.40 (d, J = 8.3 Hz, 2H), 7.29 (d, J = 8.3 Hz, 2H), 6.87 (s, 1H), 6.64 (s, 1H), 5.20 (s, 2H), 4.72 (s, 2H), 3.34 (s, 3H), 2.14 (s, 3H), 2.09 (s, 3H); LC-MS: m/z 479.1 (M + 1)$^+$. |

| Compound No. | Structure | Characterization data |
|---|---|---|
| 14 | 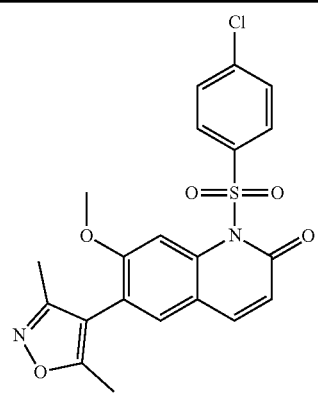 | $^1$H NMR (400 MHz, DMSO-d$_6$): δ 8.45 (d, J = 8.8 Hz, 1H), 8.16 (d, J = 8.3 Hz, 2H), 7.94 (s, 1H), 7.81 (d, J = 8.4 Hz, 2H), 7.33 (s, 1H), 7.19 (d, J = 8.4 Hz, 1H), 3.95 (s, 3H), 2.30 (s, 3H), 2.10 (s, 3H); LC-MS: m/z 445.1 (M + 1)$^+$. |
| 15 | 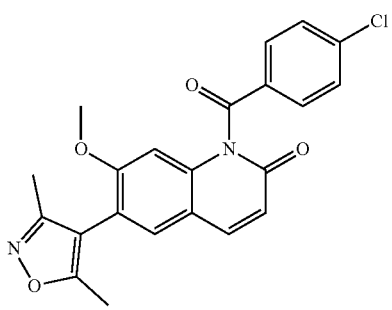 [SMILES: COc1cc2c(ccc(=O)n2C(=O)c2ccc(Cl)cc2)cc1-c1c(C)noc1C] | $^1$H NMR (400 MHz, DMSO-d$_6$): δ 8.50 (d, J = 8.3 Hz, 1H), 8.21 (d, J = 8.3 Hz, 2H), 7.98 (s, 1H), 7.73 (d, J = 8.3 Hz 2H), 7.50 (s, 1H), 7.41 (d, J = 8.8 Hz, 1H), 3.94 (s, 3H), 2.33 (s, 3H), 2.13 (s, 3H); LC-MS: m/z 409 (M + 1)$^+$. |
Example-VI: Synthesis of 2-((7-(3,5-dimethylisoxazol-4-yl)-6-methoxy-2H-benzo[b][1,4]oxazin-4(3H)-yl)methyl)aniline (Compound-16)
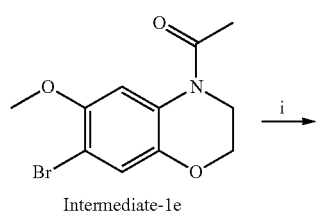
Intermediate-1e
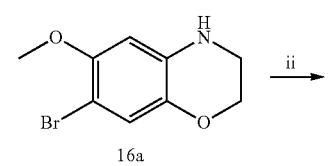
16a
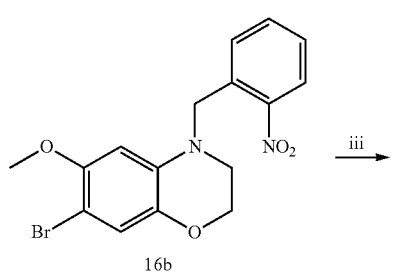
16b
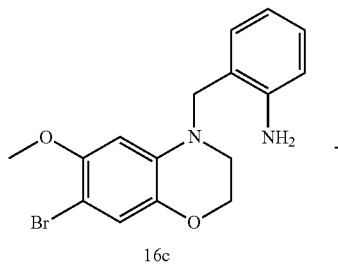
16c
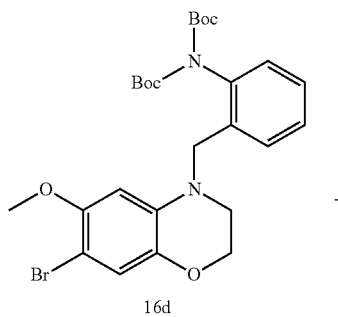
16d -continued

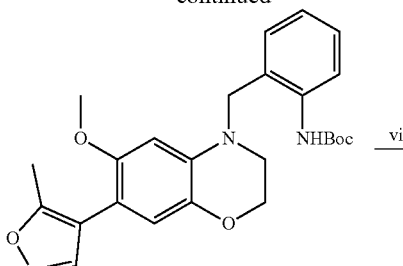

16e

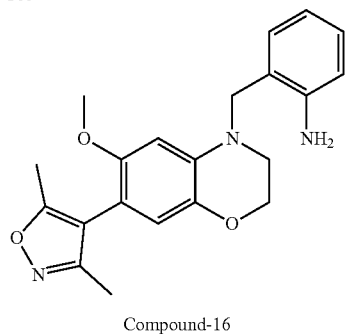

Compound-16

Step-i: Synthesis of 7-bromo-6-methoxy-3,4-dihydro-2H-benzo[b][1,4]oxazine

To a solution of intermediate-1e (2.00 g, 6.99 mmol) in MeOH (10 mL) and H$_2$O (5 mL) was added KOH (1.17 g, 20.9 mmol) and stirred at reflux temperature for 2 h. After completion of reaction, the reaction mixture was diluted with EtOAC (50 mL), washed with water (50 mL), brine (50 mL), dried over sodium sulphate and concentrated. The residue was as such taken forward for the next step without further purification (1.2 g, 70%). LC-MS: m/z 246.0 (M+2)$^{2+}$.

Step-ii: Synthesis of 7-bromo-6-methoxy-4-(2-nitrobenzyl)-3,4-dihydro-2H-benzo[b][1,4]oxazine To a solution of 7-bromo-6-methoxy-3,4-dihydro-2H-benzo[b][1,4]oxazine (1.00 g, 4.09 mmol) in DMF (10 mL) were added K$_2$CO$_3$ (1.13 g. 8.18 mmol), 2-nitro benzylbromide (1.32 g, 6.14 mmol) and stirred at RT for 24 h. After completion of reaction, the reaction mixture was diluted with EtOAC (100 mL), washed with water (50 mL), brine (50 mL), dried over sodium sulphate and concentrated. The residue was as such taken forward for next step without further purification (0.60 g, 37%). $^1$H NMR (400 MHz, DMSO-d$_6$): δ 8.09-8.07 (m, 1H), 7.73-7.69 (m, 1H), 7.57-7.48 (m, 2H), 6.88 (s, 1H), 6.23 (s, 1H), 4.86 (s, 2H), 4.17-4.15 (m, 2H), 3.53 (s, 3H), 3.38-3.36 (m, 2H); LC-MS: m/z 379.1 (M+1)$^+$.

Step-iii: Synthesis of 2-((7-bromo-6-methoxy-2H-benzo[b][1,4]oxazin-4(3H)-yl)methyl)aniline To a ice cooled solution of 7-bromo-6-methoxy-4-(2-nitrobenzyl)-3,4-dihydro-2H-benzo[b][1,4]oxazine (0.5 g, 1.26 mmol) in MeOH (20 mL) were added NiCl$_2$.6H$_2$O (0.3 g, 1.26 mmol) followed by NaBH$_4$ (0.23 g, 6.32 mmol) and stirred at the same temperature for 2 h. After completion of reaction, the reaction mixture was concentrated, the residue was treated with aq. saturated ammonium chloride solution and extracted with ethyl acetate (100 mL). The organic layer was washed with water (50 mL), brine (50 mL), dried over sodium sulphate and concentrated. The residue was taken forward for next step without further purification (0.2 g, 44%). $^1$H NMR (400 MHz, DMSO-d$_6$): δ 7.00-6.90 (m, 2H), 6.88 (s, 1H), 6.75-6.68 (m, 1H), 6.58-6.50 (m, 1H), 6.24 (s, 1H), 4.92 (s, 2H), 4.29 (s, 2H), 4.20-4.10 (m, 2H), 3.62 (s, 3H), 3.30-3.20 (m, 2H); LC-MS: m/z 349.0 (M+1)$^+$.

Step-iv: Synthesis of Compound-16 d

To a solution of 2-((7-bromo-6-methoxy-2H-benzo[b][1,4]oxazin-4(3H)-yl)methyl) aniline (0.2 g, 0.27 mmol) in DCM (2 mL) and DIPEA (0.08 mL, 0.54 mmol) was added Boc anhydride (0.071 mL, 0.33 mmol) and stirred at RT for 4 h. After completion of reaction, the reaction mixture was diluted with EtOAC (50 mL), washed with water (50 mL), brine (50 mL), dried over sodium sulphate and concentrated. The residue was taken forward to next step without further purification (0.1 g, 32%). $^1$H NMR (400 MHz, DMSO-d$_6$): δ 7.40-7.25 (m, 3H), 7.22-7.18 (m, 1H), 6.87 (s, 1H), 6.20 (s, 1H), 4.29 (s, 2H), 4.20-4.15 (m, 2H), 3.53 (s, 3H), 3.35-3.25 (m, 2H), 1.36 (s, 18H).

Step-v: Synthesis of tert-butyl (2-((7-(3,5-dimethylisoxazol-4-yl)-6-methoxy-2H-benzo[b][1,4]oxazin-4(3H)-yl)methyl)phenyl)carbamate To a solution of compound-16 d (0.1 g, 1.17 mmol) in toluene (3 mL), EtOH (1.0 mL) and H$_2$O (1.0 mL) were added 3,5-dimethylisoxazoleboronic acid (0.099 g, 0.35 mmol), sodium carbonate (0.056 g, 0.53 mmol). The resulting suspension was degassed with nitrogen purging for 20 min. Then tetrakis triphenylphosphine palladium (0.02 g, 0.01 mmol) was added and heated at 100° C. for 16 h. After completion of reaction, the reaction mixture was diluted with EtOAc (50 mL), washed with water (50 mL), brine (50 mL), dried over sodium sulphate and concentrated. The residue was directly used for next step, without further purification 0.1 g (crude). $^1$H NMR (400 MHz, DMSO-d$_6$): δ 8.73 (bs, 1H), 7.36-7.12 (m, 4H), 6.53 (s, 1H), 6.27 (s, 1H), 4.48 (s, 2H), 4.19 (bs, 2H), 3.50 (s, 3H), 3.39 (bs, 2H), 2.19 (s, 3H), 2.06 (s, 3H), 1.49 (s, 9H); LC-MS: m/z 466.3 (M+1)$^+$.

Step-vi: Synthesis of 2-((7-(3,5-dimethylisoxazol-4-yl)-6-methoxy-2H-benzo[b][1,4]oxazin-4(3H)-yl)methyl)aniline To an ice-cooled solution of tert-butyl (2-((7-(3,5-dimethylisoxazol-4-yl)-6-methoxy-2H-benzo[b][1,4]oxazin-4(3H)-yl)methyl)phenyl)carbamate (0.1 g, 0.21 mmol) was added methanolic HCl (2 mL) and stirred at RT for 3 h. After completion of reaction, the reaction mixture was diluted with EtOAC (50 mL), neutralized with aq. NaHCO$_3$ solution, washed with water (50 mL), brine (50 mL), dried over sodium sulphate and concentrated. The residue was purified on preparative TLC plate to afford the title product as brown solid (0.020 g, 39%). $^1$H NMR (400 MHz, DMSO-d$_6$+D$_2$O): δ 7.06-6.99 (m, 2H), 6.72-6.70 (m, 1H), 6.60-6.58 (m, 1H), 6.57 (s, 1H), 6.42 (s, 1H), 4.32 (s, 2H), 4.19-4.17 (m, 2H), 3.54 (s, 3H), 3.28-3.26 (m, 2H), 2.20 (s, 3H), 2.03 (s, 3H); LC-MS: m/z 366.2 (M+1)$^+$.

Example-VII: Synthesis of 7-(3,5-dimethylisoxazol-4-yl)-6-methoxy-4-(pyridin-4-ylmethyl)-2H-benzo[b][1,4]oxazin-3(4H)-one (Compound-17)

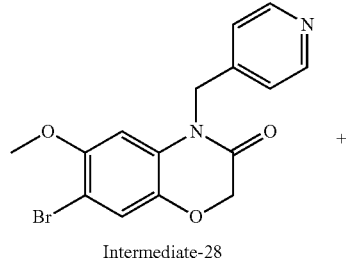

Intermediate-28

+

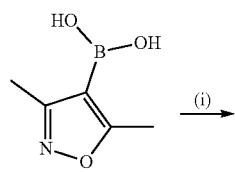

(i)

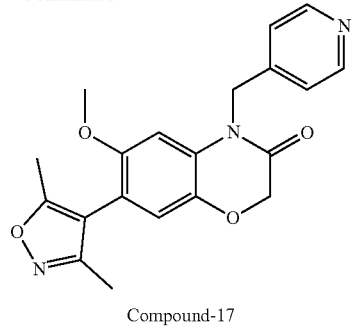

Compound-17

To a stirred solution of intermediate-28 (0.10 g, 0.29 mmol) in 1,2-DME (4.0 mL) and H$_2$O (1.0 mL) were added 3,5-dimethylisoxazoleboronic acid (0.123 g, 0.87 mmol), sodium carbonate (0.077 g, 0.73 mmol) and degassed with nitrogen purging for 20 min. Then tetrakis triphenylphosphine palladium (0.017 g, 0.015 mmol) was added and heated at 90° C. for 16 h. After completion of reaction, the reaction mixture was diluted with EtOAc (50 mL), washed with water (50 mL), brine (50 mL), dried over sodium sulphate and concentrated. The residue was purified by prep. TLC to afford the title compound as a brown solid (0.04 g, 38%). $^1$H NMR (400 MHz, DMSO-d$_6$) δ 8.55 (d, J=4.9 Hz, 2H), 7.36 (d, J=4.9 Hz, 2H), 6.96 (s, 1H), 6.66 (s, 1H), 5.27 (s, 2H), 4.80 (s, 2H), 3.58 (s, 3H), 2.22 (s, 3H), 2.04 (s, 3H); LC-MS: m/z 366.1 (M+1)$^+$.

The below compounds were prepared by procedure similar to the one described in Example-VII with appropriate variations in reactants, quantities of reagents and reaction conditions. The physiochemical characteristics of the compounds are summarized herein below table.

| Compound No. | Structure | Characterization Data |
|---|---|---|
| 18 | 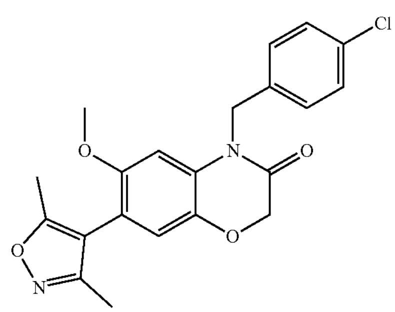 [SMILES: COc1cc2c(cc1-c1c(C)noc1C)OCC(=O)N2Cc1ccc(Cl)cc1] | $^1$H NMR (400 MHz, DMSO-d$_6$) δ 7.45-7.38 (m, 4H), 6.93 (s, 1H), 6.75 (s, 1H), 5.23 (s, 2H), 4.77 (s, 2H), 3.62 (s, 3H), 2.21 (s, 3H), 2.03 (s, 3H); ES-MS: m/z 399.1 (M + 1)$^+$. |
| 19 & 20 | 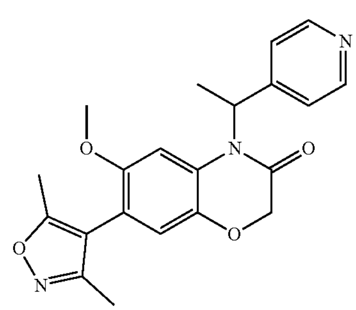 [SMILES: COc1cc2c(cc1-c1c(C)noc1C)OCC(=O)N2C(C)c1ccncc1] | Compound 19 (Isomer-1): $^1$H NMR (400 MHz, CDCl$_3$): δ 8.63 (dd, J = 4.4 & 2.4 Hz, 2H), 7.30 (d, J = 4.8 Hz, 2H), 6.79 (s, 1H), 6.40-6.30 (m, 1H), 6.14 (s, 1H), 4.75-4.60 (m, 2H), 3.37 (s, 3H), 2.26 (s, 3H), 2.11 (s, 3H), 1.88 (d, J = 7.2 Hz, 3H); LC-MS: m/z 380.2 (M + 1)$^+$.<br>Compound 20 (Isomer-2): $^1$H NMR (400 MHz, CDCl$_3$): δ 8.64 (d, J = 5.6 Hz, 2H), 7.30 (d, J = 4.8 Hz, 2H), 6.79 (s, 1H), 6.42-6.30 (m, 1H), 6.14 (s, 1H), 4.80-4.60 (m, 2H), 3.37 (s, 3H), 2.26 (s, 3H), 2.12 (s, 3H), 1.88 (d, J = 7.2 Hz, 3H); LC-MS: m/z 380.2 (M + 1)$^+$. |

| Compound No. | Structure | Characterization Data |
|---|---|---|
| 21 | 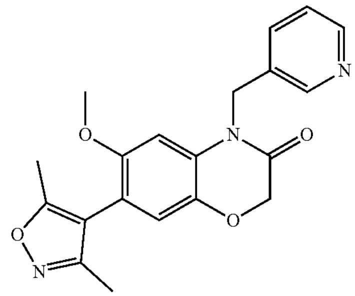 [SMILES: COc1cc2c(cc1-c1c(C)noc1C)OCC(=O)N2Cc1cccnc1] | ¹H NMR (400 MHz, DMSO-d₆) δ 8.66 (s, 1H), 8.57 (d, J = 4.4 Hz, 1H), 7.66 (d, J = 7.6 Hz, 1H), 7.33-7.30 (m, 1H), 6.78 (s, 1H), 6.47 (s, 1H), 5.22 (s, 2H), 4.72 (s, 2H), 3.60 (s, 3H), 2.27 (s, 3H), 2.13 (s, 3H); LC-MS: m/z 366.2 (M + 1)⁺. |
| 22 | 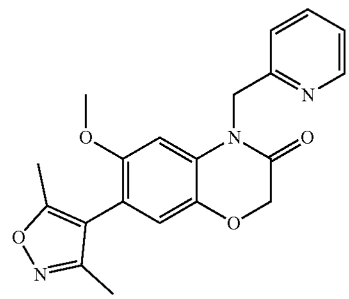 [SMILES: COc1cc2c(cc1-c1c(C)noc1C)OCC(=O)N2Cc1ccccn1] | ¹H NMR (400 MHz, CDCl₃) δ 8.59 (d, J = 4.8 Hz, 1H), 8.69 (td, J = 8.0 & 2.0 Hz, 1H), 7.39 (d, J = 8.0 Hz, 1H), 7.24-7.22 (m, 1H), 6.95 (s, 1H), 6.75 (s, 1H), 5.30 (s, 2H), 4.71 (s, 2H), 3.66 (s, 3H), 2.27 (s, 3H), 2.13 (s, 3H); LC-MS: m/z 366.1 (M + 1)⁺. |
| 23 | 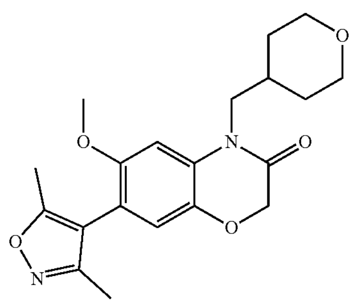 [SMILES: COc1cc2c(cc1-c1c(C)noc1C)OCC(=O)N2CC1CCOCC1] | ¹H NMR (400 MHz, CDCl₃) δ 6.79 (s, 1H), 6.60 (s, 1H), 4.60 (s, 2H), 4.00 (dd, J = 4.2 & 2.4 Hz, 2H), 3.90 (d, J = 7.2 Hz, 2H), 3.77 (s, 3H), 3.36 (t, J = 11.2 Hz, 2H), 2.31 (s, 3H), 2.18 (s, 3H), 2.08-2.00 (m, 1H), 1.64-1.60 (m, 2H), 1.58-1.40 (m, 2H); LC-MS: m/z 373.2 (M + 1)⁺. |
| 24 & 25 | 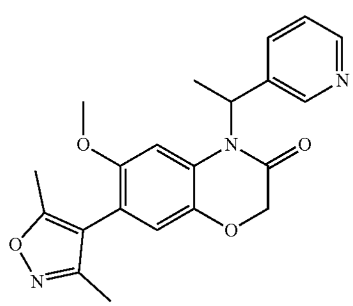 [SMILES: COc1cc2c(cc1-c1c(C)noc1C)OCC(=O)N2C(C)c1cccnc1] | Compound 24 (Isomer-1): ¹H NMR (400 MHz, CDCl₃): δ 8.69 (s, 1H), 8.58 (d, J = 4.4 Hz, 1H), 7.70 (d, J = 7.6 Hz, 1H), 7.35-7.31 (m, 1H), 6.78 (s, 1H), 6.41 (s, 1H), 6.25 (q, J = 7.2 Hz, 1H), 4.72-4.62 (m, 2H), 3.40 (s, 3H), 2.26 (s, 3H), 2.12 (s, 3H), 1.93 (d, J = 6.8 Hz, 3H). LC-MS: m/z 380.2 (M + 1)⁺.<br>Compound 25 (Isomer-2): ¹H NMR (400 MHz, CDCl₃): δ 8.70 (s, 1H), 8.58 (d, J = 4.4 Hz, 1H), 7.70 (d, J = 7.6 Hz, 1H), 7.35-7.32 (m, 1H), 6.78 (s, 1H), 6.41 (q, J = 7.2 Hz, 1H), 6.25 (s, 1H), 4.72-4.62 (m, 2H), 3.40 (s, 3H), 2.26 (s, 3H), 2.11 (s, 3H), 1.93 (d, J = 6.8 Hz, 3H); LC-MS: m/z 380.2 (M + 1)⁺. |
| 26 | 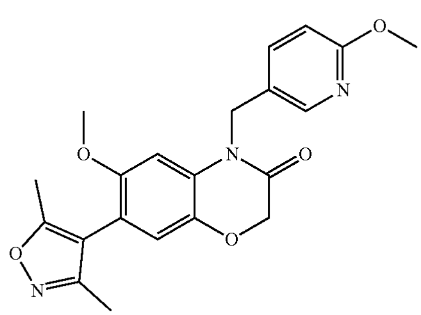 [SMILES: COc1ccc(CN2C(=O)COc3cc(-c4c(C)noc4C)c(OC)cc32)cn1] | ¹H NMR (400 MHz, CDCl₃): δ 8.18 (d, J = 2.4 Hz, 1H), 7.57 (dd, J = 8.8 & 2.4 Hz, 1H), 6.76 (s, 1H), 6.74 (s, 1H), 6.57 (s, 1H), 5.12 (s, 2H), 4.69 (s, 2H), 3.92 (s, 3H), 3.65 (s, 3H), 2.27 (s, 3H), 2.13 (s, 3H); LC-MS: m/z 396.1 (M + 1)⁺. |

| Compound No. | Structure | Characterization Data |
|---|---|---|
| 27 | 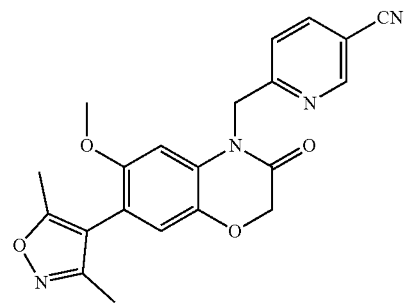 [SMILES: COc1cc2c(cc1-c1c(C)noc1C)OCC(=O)N2Cc1ccc(C#N)cn1] | $^1$H NMR (400 MHz, CDCl$_3$): δ 8.86 (d, J = 1.6 Hz, 1H), 7.97 (dd, J = 8.0 & 2.0 Hz, 1H), 7.55 (d, J = 8.4 Hz, 1H), 6.81 (s, 1H), 6.78 (s, 1H), 5.33 (s, 2H), 4.70 (s, 2H), 3.67 (s, 3H), 2.27 (s, 3H), 2.13 (s, 3H): LC-MS: m/z 391.2 (M + 1)$^+$. |
| 28 | 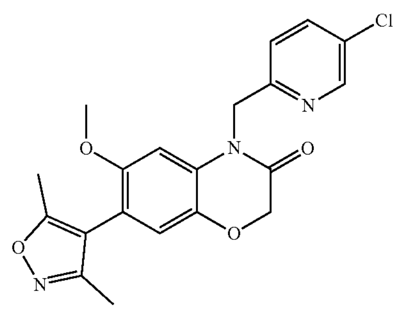 [SMILES: COc1cc2c(cc1-c1c(C)noc1C)OCC(=O)N2Cc1ccc(Cl)cn1] | $^1$H NMR (400 MHz, CDCl$_3$) δ 8.54 (d, J = 2.0 Hz, 1H), 7.67 (dd, J = 8.0, 2.4 Hz, 1H), 7.38 (d, J = 8.0 Hz, 1H), 6.96 (s, 1H), 6.75 (s, 1H), 5.26 (s, 2H), 4.69 (s, 2H), 3.69 (s, 3H), 2.27 (s, 3H), 2.13 (s, 3H); LC-MS: m/z 400.2 (M + 1)$^+$. |
| 29 | 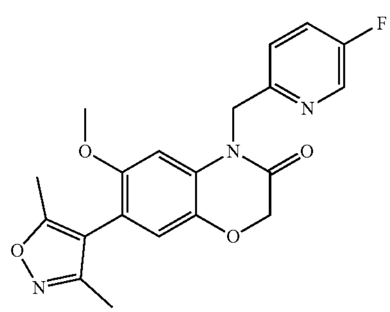 [SMILES: COc1cc2c(cc1-c1c(C)noc1C)OCC(=O)N2Cc1ccc(F)cn1] | $^1$H NMR (400 MHz, CDCl$_3$) δ 8.43 (d, J = 2.0 Hz, 1H), 7.45-7.26 (m, 2H), 7.00 (s, 1H), 6.75 (s, 1H), 5.27 (s, 2H), 4.69 (s, 2H), 3.69 (s, 3H), 2.27 (s, 3H), 2.13 (s, 3H); LC-MS: m/z 384.2 (M + 1)$^+$. |
| 30 | 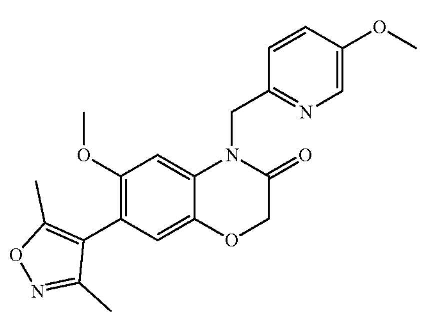 [SMILES: COc1ccc(CN2C(=O)COc3cc(-c4c(C)noc4C)c(OC)cc32)nc1] | $^1$H NMR (400 MHz, CDCl$_3$) δ 8.25 (d, J = 2.8 Hz, 1H), 7.36 (d, J = 8.8 Hz, 1H), 7.19 (dd, J = 8.8 & 2.0 Hz, 1H), 7.10 (s, 1H), 6.73 (s, 1H), 5.23 (s, 2H), 4.68 (s, 2H), 3.70 (s, 3H), 3.58 (s, 3H), 2.27 (s, 3H), 2.13 (s, 3H); LC-MS: m/z 396.2 (M + 1)$^+$. |
| 31 | 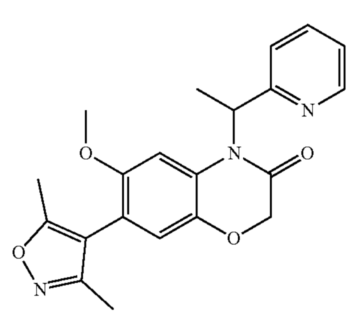 [SMILES: COc1cc2c(cc1-c1c(C)noc1C)OCC(=O)N2C(C)c1ccccn1] | $^1$H NMR (400 MHz, CDCl$_3$) δ 8.60 (bs, 1H), 7.82-7.79 (m, 1H), 7.62 (d, J = 8.4 Hz, 1H), 7.34-7.31 (m, 1H), 6.92 (s, 1H), 6.63 (s, 1H), 6.24-6.22 (m, 1H), 4.67 (s, 2H), 3.43 (s, 3H), 2.21 (s, 3H), 1.97 (s, 3H), 1.84 (d, J = 6.9 Hz, 3H); LC-MS: m/z 380.2 (M + 1)$^+$. |

| Compound No. | Structure | Characterization Data |
|---|---|---|
| 32 | 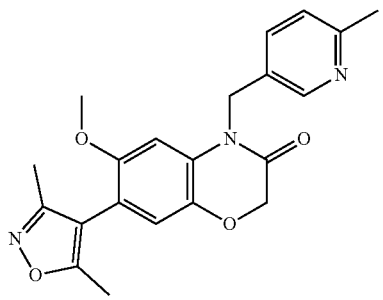 [SMILES: COc1cc2c(cc1-c1c(C)noc1C)OCC(=O)N2Cc1ccc(C)nc1] | ¹H NMR (400 MHz, CDCl₃): δ 8.58 (s, 1H), 7.56 (d, J = 7.4 Hz, 1H), 7.17 (d, J = 7.6 Hz, 1H), 6.77 (s, 1H), 6.51 (s, 1H), 5.17 (s, 2H), 4.70 (s, 2H), 3.61 (s, 3H), 2.55 (s, 3H), 2.26 (s, 3H), 2.12 (s, 3H); ES-MS: m/z 380.2 (M + 1)⁺. |
| 33 & 34 | 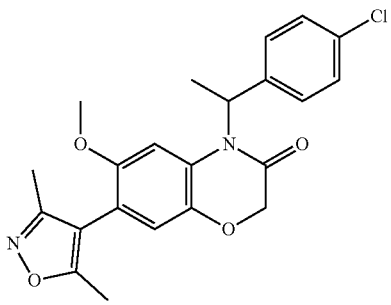 [SMILES: COc1cc2c(cc1-c1c(C)noc1C)OCC(=O)N2C(C)c1ccc(Cl)cc1] | Compound 33 (Isomer-1): ¹H NMR (400 MHz, CDCl₃): δ 7.37-7.30 (m, 4H), 6.76 (s, 1H), 6.45-6.35 (m, 1H), 6.27 (s, 1H), 4.72-4.60 (m, 2H), 3.38 (s, 3H), 2.25 (s, 3H), 2.12 (s, 3H), 1.84 (d, J = 7.4 Hz, 3H); LC-MS: m/z 413.0 (M + 1)⁺. Compound 34 (Isomer-2): ¹H NMR (400 MHz, CDCl₃): δ 7.31-7.27 (m, 4H), 6.69 (s, 1H), 6.35-6.28 (m, 1H), 6.20 (s, 1H), 4.65-4.54 (m, 2H), 3.32 (s, 3H), 2.19 (s, 3H), 2.05 (s, 3H), 1.78 (d, J = 6.9 Hz, 3H); LC-MS: m/z 413.0 (M + 1)⁺. |
| 35 | 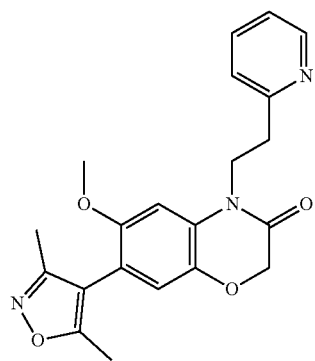 [SMILES: COc1cc2c(cc1-c1c(C)noc1C)OCC(=O)N2CCc1ccccn1] | ¹H NMR (400 MHz, DMSO-d₆): δ 8.57 (d, J = 3.4 Hz, 1H), 7.61 (t, J = 6.9 Hz, 1H), 7.26 (s, 1H), 7.21-7.14 (m, 1H), 6.89 (s, 1H), 6.74 (s, 1H), 4.60 (s, 2H), 4.37 (t, J = 7.3 Hz, 2H), 3.79 (s, 3H), 3.20 (t, J = 7.6 Hz, 2H), 2.30 (s, 3H), 2.15 (s, 3H); LC-MS: m/z 380.1 (M + 1)⁺. |
| 36 | 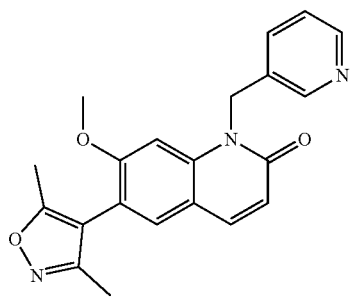 [SMILES: COc1cc2c(ccc(=O)n2Cc2cccnc2)cc1-c1c(C)noc1C] | ¹H NMR (400 MHz, DMSO-d₆): δ 8.64 (d, J = 2.0 Hz, 1H), 8.47 (d, J = 3.5 Hz, 1H), 7.92 (d, J = 9.3 Hz, 1H), 7.68 (d, J = 7.8 Hz, 1H), 7.64 (s, 1H), 7.36 (dd, J = 4.9 & 3.0 Hz, 1H), 7.01 (s, 1H), 6.60 (d, J = 9.3 Hz, 1H), 5.63 (s, 2H), 3.78 (s, 3H), 2.24 (s, 3H), 2.05 (s, 3H); LC-MS: m/z 362.2 (M + 1)⁺. |

| Compound No. | Structure | Characterization Data |
|---|---|---|
| 37 | 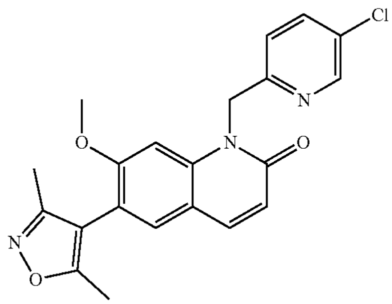 [SMILES: COc1cc2c(ccc(=O)n2Cc2ccc(Cl)cn2)cc1-c1c(C)noc1C] | $^1$H NMR (400 MHz, DMSO-d$_6$): δ 8.57 (d, J = 2.0 Hz, 1H), 7.90-7.78 (m, 2H), 7.62 (s, 1H), 7.41 (d, J = 7.3 Hz, 1H), 7.07 (s, 1H), 6.57 (d, J = 9.3 Hz, 1H), 5.65 (s, 2H), 3.76 (s, 3H), 2.25 (s, 3H), 2.06 (s, 3H); LC-MS: m/z 396.1 (M + 1)$^+$. |
| 38 | 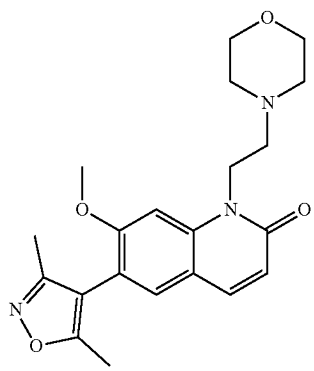 [SMILES: COc1cc2c(ccc(=O)n2CCN2CCOCC2)cc1-c1c(C)noc1C] | $^1$H NMR (400 MHz, DMSO-d$_6$): δ 7.83 (d, J = 9.0 Hz, 1H), 7.61 (s, 1H), 7.07 (s, 1H), 6.47 (d, J = 9.7 Hz, 1H), 4.43 (t, J = 7.3 Hz, 2H), 3.94 (s, 3H), 3.58 (t, J = 4.4 Hz, 4H), 2.61-2.54 (m, 6H), 2.49 (s, 3H), 2.09 (s, 3H); LC-MS: m/z 384.2 (M + 1)$^+$. |
| 39 | 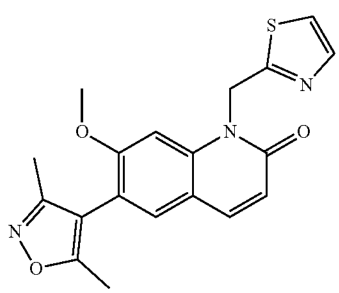 [SMILES: COc1cc2c(ccc(=O)n2Cc2nccs2)cc1-c1c(C)noc1C] | $^1$H NMR (400 MHz, DMSO-d$_6$): δ 7.92-7.90 (m, 1H), 7.78-7.77 (m, 1H), 7.71-7.70 (m, 1H), 7.63 (s, 1H), 7.36 (s, 1H), 6.57 (d, J = 9.7 Hz, 1H), 5.85 (s, 2H), 3.86 (s, 3H), 2.25 (s, 3H), 2.06 (s, 3H); LC-MS: m/z 368.1 (M + 1)$^+$. |
| 40 | 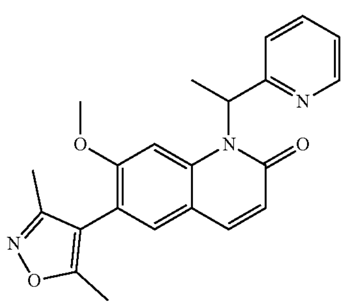 [SMILES: COc1cc2c(ccc(=O)n2C(C)c2ccccn2)cc1-c1c(C)noc1C] | $^1$H NMR (400 MHz, DMSO-d$_6$): δ 8.57-8.56 (m, 1H), 8.19-8.14 (m, 1H), 7.78 (dt, J = 7.8, 1.9 Hz, 1H), 7.73 (s, 1H), 7.49 (d, J = 8.0 Hz, 1H), 7.31-7.29 (m, 1H), 7.18 (s, 1H), 6.98 (d, J = 8.8 Hz, 1H), 6.49-6.44 (m, 1H), 3.88 (s, 3H), 2.32 (s, 3H), 2.08 (s, 3H), 1.67 (d, J = 6.4 Hz, 3H); LC-MS: m/z 376.2 (M + 1)$^+$. |

| Compound No. | Structure | Characterization Data |
|---|---|---|
| 41 | 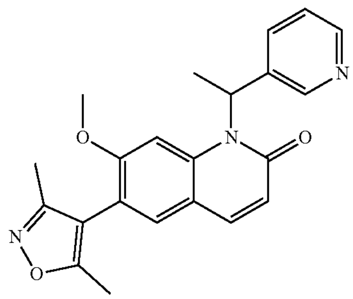 [SMILES: COc1cc2c(ccc(=O)n2C(C)c2cccnc2)cc1-c1c(C)noc1C] | ¹H NMR (400 MHz, DMSO-d₆): δ 8.76 (s, 1H), 8.50-8.48 (m, 1H), 8.16 (d, J = 8.8 Hz, 1H), 7.94-7.91 (m, 1H), 7.73 (s, 1H), 7.41-7.38 (m, 1H), 7.23 (s, 1H), 6.94 (d, J = 8.8 Hz, 1H), 6.51-6.46 (m, 1H), 3.89 (s, 3H), 2.27 (s, 3H), 2.08 (s, 3H), 1.69 (d, J = 6.0 Hz, 3H); LC-MS: m/z 376.2 (M + 1)⁺. |
| 42 | 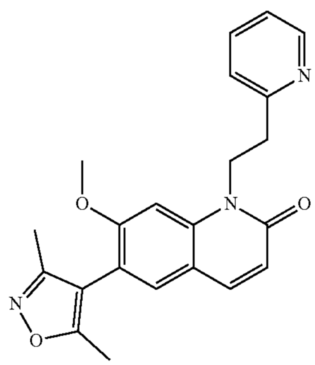 [SMILES: COc1cc2c(ccc(=O)n2CCc2ccccn2)cc1-c1c(C)noc1C] | ¹H NMR (400 MHz, DMSO-d₆): δ 8.53-8.50 (m, 1H), 8.13 (d, J = 8.8 Hz, 1H), 7.76-7.70 (m, 1H), 7.72 (s, 1H), 7.39-7.35 (m, 1H), 7.30 (s, 1H), 7.28-7.22 (m, 1H), 6.82 (d, J = 8.8 Hz, 1H), 4.79 (t, J = 6.8 Hz, 2H), 3.41 (s, 3H), 3.27 (t, J = 6.8 Hz, 2H), 2.29 (s, 3H), 2.08 (s, 3H); LC-MS: m/z 376.2 (M + 1)⁺. |
| 43 | 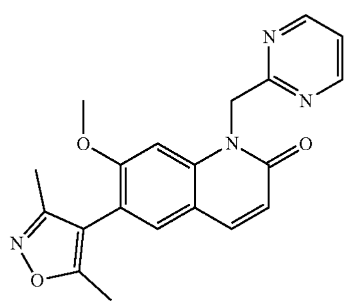 [SMILES: COc1cc2c(ccc(=O)n2Cc2ncccn2)cc1-c1c(C)noc1C] | ¹H NMR (400 MHz, DMSO-d₆): δ 8.76-8.73 (m, 2H), 7.90 (d, J = 9.2 Hz, 1H), 7.62 (s, 1H), 7.43-7.40 (m, 1H), 6.90 (s, 1H), 6.54 (d, J = 9.2 Hz, 1H), 5.75 (s, 2H), 3.69 (s, 3H), 2.25 (s, 3H), 2.06 (s, 3H); LC-MS: m/z 363.2 (M + 1)⁺. |
| 44 | 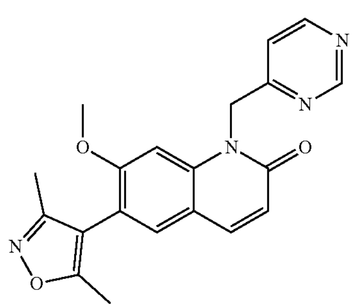 [SMILES: COc1cc2c(ccc(=O)n2Cc2ccncn2)cc1-c1c(C)noc1C] | ¹H NMR (400 MHz, DMSO-d₆): δ 9.10 (d, J =2.0 Hz, 1H), 8.75 (d, J = 7.2 Hz, 1H), 7.93 (d, J = 9.2 Hz, 1H), 7.65 (s, 1H), 7.45-7.43 (m, 1H), 6.97 (s, 1H), 6.57 (d, J = 9.4 Hz, 1H), 5.68 (s, 2H), 3.74 (s, 3H), 2.26 (s, 3H), 2.06 (s, 3H); LC-MS: m/z 363.2 (M + 1)⁺. |

| Compound No. | Structure | Characterization Data |
|---|---|---|
| 45 | 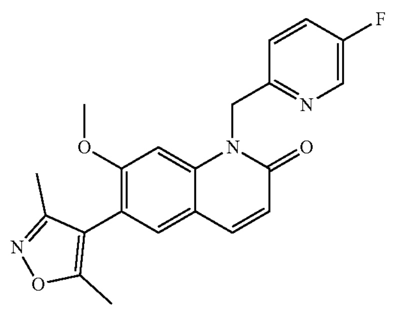 [SMILES: COc1cc2c(ccc(=O)n2Cc2ccc(F)cn2)cc1-c1c(C)noc1C] | ¹H NMR (400 MHz, DMSO-d₆): δ 8.53 (d, J = 3.0 Hz, 1H), 7.90 (d, J = 9.2 Hz, 1H), 7.74-7.69 (m, 1H), 7.62 (s, 1H), 7.46-7.43 (m, 1H), 7.11 (s, 1H), 6.57 (d, J = 9.2 Hz, 1H), 5.65 (s, 2H), 3.77 (s, 3H), 2.25 (s, 3H), 2.06 (s, 3H); LC-MS: m/z 380.2 (M + 1)⁺. |
| 46 | 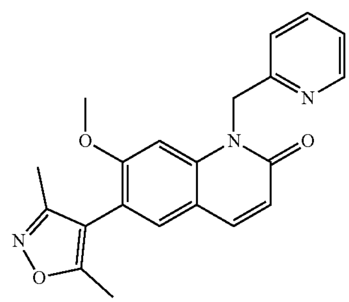 [SMILES: COc1cc2c(ccc(=O)n2Cc2ccccn2)cc1-c1c(C)noc1C] | ¹H NMR (400 MHz, DMSO-d₆): δ 8.52 (d, J = 4.4 Hz, 1H), 7.90 (d, J = 9.6 Hz, 1H), 7.79-7.75 (m, 1H), 7.62 (s, 1H), 7.33-7.28 (m, 2H), 7.12 (s, 1H), 6.58 (d, J = 9.6 Hz, 1H), 5.65 (s, 2H), 3.74 (s, 3H), 2.24 (s, 3H), 2.05 (s, 3H). MS (ES) m/z 362.3 (M + 1)⁺. |
| 47 | 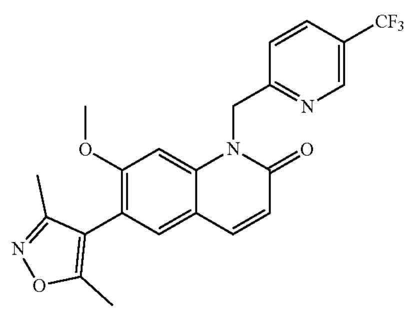 [SMILES: COc1cc2c(ccc(=O)n2Cc2ccc(C(F)(F)F)cn2)cc1-c1c(C)noc1C] | ¹H NMR (CDCl₃, 400 MHz): δ 8.83 (s, 1H), 7.85 (d, J = 7.6 Hz, 1H), 7.65 (d, J = 9.2 Hz, 1H), 7.52 (d, J = 8.0 Hz, 1H), 7.26 (s, 1H), 7.15 (s, 1H), 6.67 (d, J = 9.6 Hz, 1H), 5.73 (bs, 2H), 3.80 (s, 3H), 2.26 (s, 3H), 2.11 (s, 3H); LC-MS: m/z 430.1 (M + 1)⁺, |
| 48 | 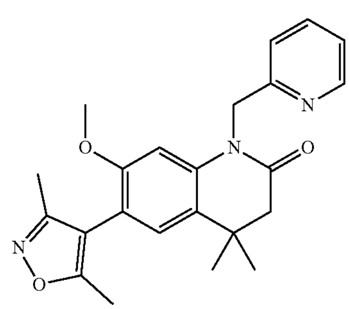 [SMILES: COc1cc2c(cc1-c1c(C)noc1C)C(C)(C)CC(=O)N2Cc1ccccn1] | ¹H NMR (400 MHz, DMSO-d₆) δ 8.53-8.52 (m, 1H), 7.77-7.73 (m, 1H), 7.37-7.25 (m, 2H), 7.11 (s, 1H). 6.81 (s, 1H), 5.29 (s, 2H), 3.59 (s, 3H), 2.59 (s, 2H), 2.22 (s, 3H), 2.04 (s, 3H), 1.25 (s, 6H); LC-MS: m/z 392.2 (M + 1)⁺. |
| 49 | 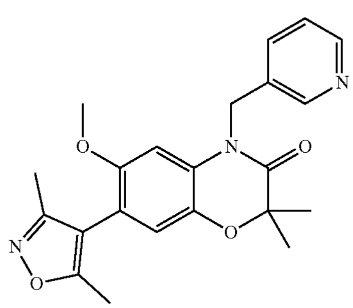 [SMILES: COc1cc2c(cc1-c1c(C)noc1C)OC(C)(C)C(=O)N2Cc1cccnc1] | ¹H NMR (400 MHz, DMSO-d₆): δ 8.62 (s, 1H), 8.56 (d, J = 3.9 Hz, 1H), 7.61 (d, J = 7.9 Hz, 1H), 7.32-7.29 (m, 1H), 6.75 (s, 1H), 6.42 (s, 1H), 5.18 (s, 2H), 3.59 (s, 3H), 2.27 (s, 3H), 2.13 (s, 3H), 1.58 (s, 6H); LC-MS: m/z 394.2 (M + 1)⁺. |

| Compound No. | Structure | Characterization Data |
|---|---|---|
| 50 | 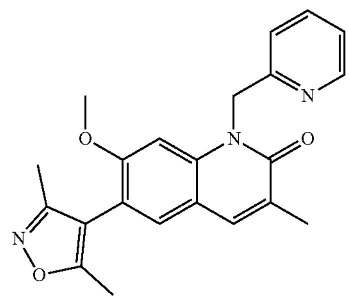 [SMILES: COc1cc2c(cc1-c1c(C)noc1C)cc(C)c(=O)n2Cc1ccccn1] | $^1$H NMR (400 MHz, CDCl$_3$): δ 8.58 (s, 1H), 7.64-7.61 (m, 1H), 7.54 (s, 1H), 7.34-7.32 (m, 1H), 7.20-7.17 (m, 3H), 5.71 (s, 2H), 3.77 (s, 3H), 2.31 (s, 3H), 2.31 (s, 3H), 2.26 (s, 3H); LC-MS: m/z 376.2 (M + 1)$^+$. |
| 51 | 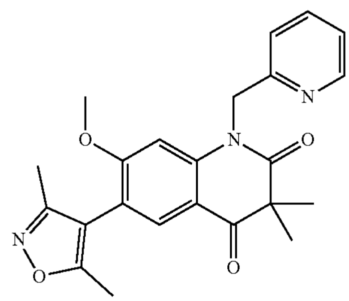 [SMILES: COc1cc2c(cc1-c1c(C)noc1C)C(=O)C(C)(C)C(=O)N2Cc1ccccn1] | $^1$H NMR (400 MHz, DMSO-d$_6$): δ 8.50 (d, J = 4.4 Hz, 1H), 7.79-7.75 (m, 1H), 6.55 (s, 1H), 7.41 (d, J = 7.9 Hz, 1H), 7.35-7.25 (m, 1H), 6.94 (s, 1H), 5.41 (s, 2H), 3.74 (s, 3H), 2.22 (s, 3H), 2.02 (s, 3H), 1.42 (s, 6H); LC-MS: m/z 406.2 (M + 1)$^+$. |
| 52 | 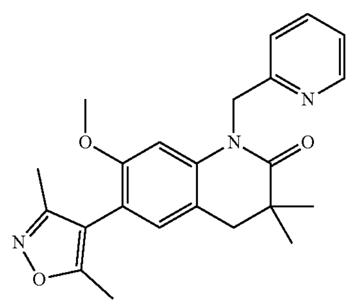 [SMILES: COc1cc2c(cc1-c1c(C)noc1C)CC(C)(C)C(=O)N2Cc1ccccn1] | $^1$H NMR (400 MHz, DMSO-d$_6$): δ 8.50 (d, J = 7.8 Hz, 1H), 7.66-7.62 (m, 1H), 7.30-7.18 (m, 2H), 6.84 (s, 1H), 6.78 (s, 1H), 5.30 (s, 2H), 3.63 (s, 3H), 2.79 (s, 2H), 2.26 (s, 3H), 2.12 (s, 3H), 1.27 (s, 6H); LC-MS: m/z 392.2 (M +1)$^+$. |
| 53 | 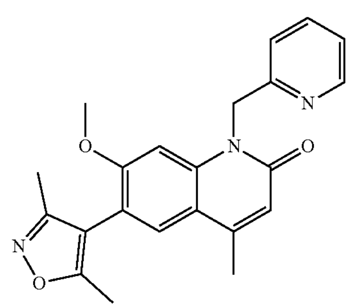 [SMILES: COc1cc2c(cc1-c1c(C)noc1C)c(C)cc(=O)n2Cc1ccccn1] | $^1$H NMR (400 MHz, DMSO-d$_6$): δ 8.50 (d, J = 3.9 Hz, 1H), 7.78-7.74 (m, 1H), 7.59 (s, 1H), 7.36-7.27 (m, 2H), 7.10 (s, 1H), 6.50 (s, 1H), 5.63 (s, 2H), 3.73 (s, 3H), 2.44 (s, 3H), 2.25 (s, 3H), 2.05 (s, 3H); LC-MS: m/z 376.2 (M + 1)$^+$. |
| 54 | 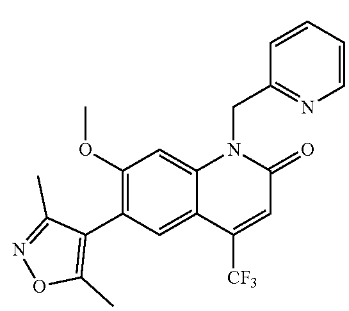 [SMILES: COc1cc2c(cc1-c1c(C)noc1C)c(C(F)(F)F)cc(=O)n2Cc1ccccn1] | $^1$H NMR (400 MHz, CDCl$_3$) δ 8.59 (d, J = 4.4 Hz, 1H), 7.67 (dt J = 8.0, 0.8 Hz, 1H), 7.54 (d, J = 0.8 Hz, 1H), 7.42-7.38 (m, 2H), 7.25-7.20 (m, 1H), 7.08 (s, 1H), 5.71 (bs, 2H), 3.85 (s, 3H), 2.28 (s, 3H), 2.14 (s, 3H); LC-MS: m/z 430.2 (M + 1)$^+$. |

| Compound No. | Structure | Characterization Data |
|---|---|---|
| 55 | 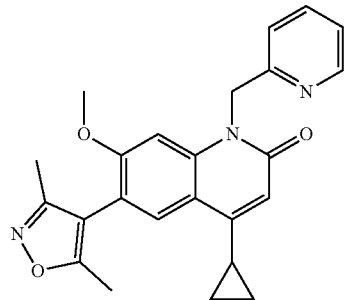 [SMILES: COc1cc2c(cc1-c1c(C)noc1C)c(C1CC1)cc(=O)n2Cc1ccccn1] | $^1$H NMR (400 MHz, DMSO-d$_6$) δ 8.54-8.52 (m, 1H), 7.94 (s, 1H), 7.77 (dt, J = 7.8, 2.0 Hz, 1H), 7.31-7.28 (m, 2H), 7.13 (s, 1H), 6.27 (s, 1H), 5.63 (s, 2H), 3.74 (s, 3H), 2.32-2.29 (m, 1H), 2.27 (s, 3H), 2.08 (s, 3H), 1.06-1.01 (m, 2H), 0.81-0.77 (m, 2H); LC-MS: m/z 402.2 (M + 1)$^+$. |
| 56 | 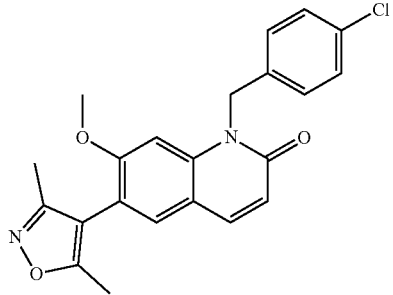 [SMILES: COc1cc2c(ccc(=O)n2Cc2ccc(Cl)cc2)cc1-c1c(C)noc1C] | $^1$HNMR 400 MHz (DMSO-d$_6$) δ 7.91 (d, J = 9.2 Hz, 1H), 7.63 (s, 1H), 7.40-7.36 (m, 4H), 6.96 (s, 1H), 6.60 (d, J = 9.2 Hz, 1H), 5.58 (s, 2H), 3.77 (s, 3H), 2.24 (s, 3H), 2.05 (s, 3H). MS (ES) m/e 395.3 (M + 1)$^+$. |
| 57 | 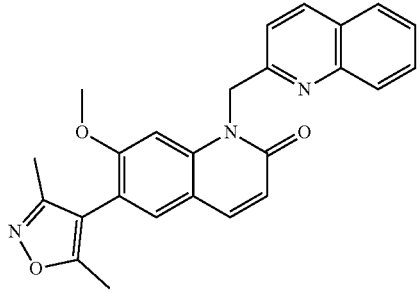 [SMILES: COc1cc2c(ccc(=O)n2Cc2ccc3ccccc3n2)cc1-c1c(C)noc1C] | $^1$H NMR (400 MHz DMSO-d$_6$): δ 8.41 (d, J = 8.8 Hz, 1H), 8.24 (d, J = 8.8 Hz, 1H), 8.01-7.98 (m, 2H), 7.81-7.77 (m, 2H), 7.69 (d, J = 8.3 Hz, 1H), 7.62 (t, J = 7.8 Hz, 1H), 7.27 (s, 1H), 7.08 (d, J = 8.8 Hz, 1H), 5.79 (s, 2H), 3.89 (s, 3H), 2.30 (s, 3H), 2.10 (s, 3H); LC-MS: m/z 412.2 (M +1)$^+$. |
| 58 | 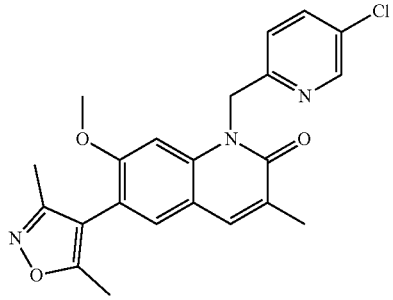 [SMILES: COc1cc2c(cc1-c1c(C)noc1C)cc(C)c(=O)n2Cc1ccc(Cl)cn1] | $^1$H NMR (400 MHz, DMSO-d$_6$): δ 8.58 (d, J = 2.4 Hz, 1H), 7.91 (dd, J1 = 2.4 Hz, J2 = 8.8 Hz, 1H), 7.79 (s, 1H), 7.53 (s, 1H), 7.39 (d, J = 8.8 Hz, 1H), 7.05 (s, 1H), 5.67 (s, 2H), 3.75 (s, 3H), 2.25 (s, 3H), 2.15 (s, 3H), 2.06 (s, 3H); LC-MS: m/z 410.2 (M + 1)$^+$. |

-continued

| Compound No. | Structure | Characterization Data |
|---|---|---|
| 59 | 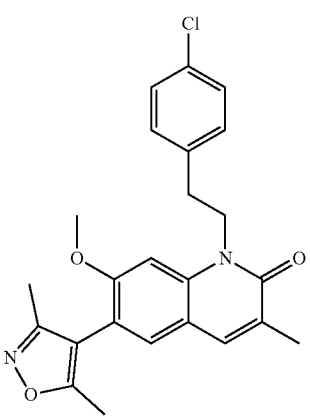 [SMILES: COc1cc2c(cc1-c1c(C)noc1C)cc(C)c(=O)n2CCc1ccc(Cl)cc1] | $^1$H NMR (400 MHz, CDCl$_3$): δ 7.52 (s, 1H), 7.35-7.23 (m, 5H), 6.72 (s, 1H), 4.50 (t, J = 7.8 Hz, 2H), 3.88 (s, 3H), 3.07 (t, J = 7.9 Hz, 2H), 2.27 (s, 3H), 2.26 (s, 3H), 2.16 (s, 3H); LC-MS: m/z 423.1 (M + 1)$^+$. |
| 60* | 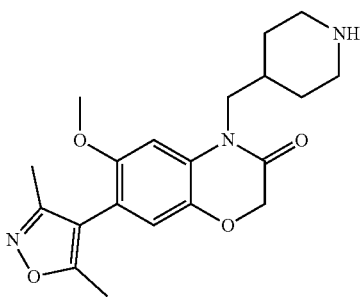 [SMILES: COc1cc2c(cc1-c1c(C)noc1C)OCC(=O)N2CC1CCNCC1] | $^1$H NMR (400 MHz, DMSO-d$_6$) δ 8.34 (bs, 1H), 6.93 (s, 1H), 6.89 (s, 1H), 4.63 (s, 2H), 3.94 (d, J = 7.7 Hz, 2H), 3.80 (s, 3H), 3.14 (d, J = 11.7 Hz, 2H), 2.75-2.60 (m, 2H), 2.33 (s, 3H), 2.08 (s, 3H), 2.05-1.80 (m, 1H), 1.75-1.55 (m, 2H), 1.42-1.28 (m, 2H); LC-MS: m/z 372.2 (M + 1)$^+$; |
| 61* | 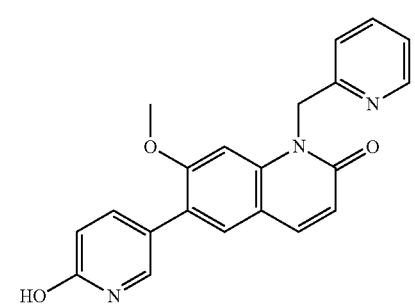 [SMILES: COc1cc2c(ccc(=O)n2Cc2ccccn2)cc1-c1ccc(O)nc1] | $^1$H NMR (300 MHz, CD$_3$OD): δ 8.53 (d, J = 5.1 Hz, 1H), 7.95 (d J = 9.6 Hz, 1H), 7.82-7.74 (m, 2H), 7.64 (s, 1H), 7.85 (d, J = 2.7 Hz, 1H), 7.34-7.25 (m, 2H), 7.04 (s, 1H), 6.6 (d, J = 9.3 Hz, 1H), 6.56 (d, J = 9.6 Hz, 1H), 5.74 (s, 2H), 3.78 (s, 3H); LC-MS: m/z 360.10 (M + 1)$^+$. |
| 62 | 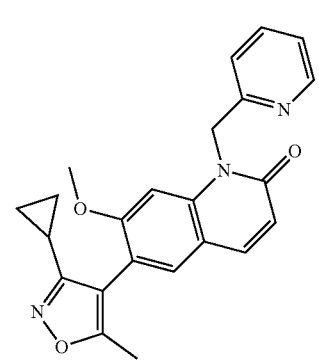 [SMILES: COc1cc2c(ccc(=O)n2Cc2ccccn2)cc1-c1c(C2CC2)noc1C] | $^1$H NMR (300 MHz, CDCl$_3$): δ 8.82 (s, 1H), 7.76-7.68 (m, 2H), 7.41-7.38 (m, 1H), 7.34-7.30 (m, 1H), 7.15 (s, 1H), 6.71 (d, J = 6.6 Hz, 2H), 5.78 (s, 2H), 3.80 (s, 3H), 2.24 (s, 3H), 1.55-1.50 (m, 1H), 1.02-0.96 (m, 2H), 0.88-0.81 (m, 2H). LCMS (ESI, m/z): 388.0 (M + 1)$^+$. |

| Compound No. | Structure | Characterization Data |
|---|---|---|
| 63 | 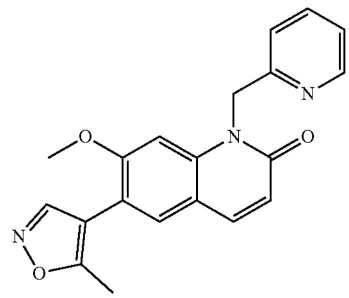 [SMILES: COc1cc2c(ccc(=O)n2Cc2ccccn2)cc1-c1cnoc1C] | ¹H NMR (CDCl₃, 300 MHz): δ 8.58 (d, J = 4.2 Hz, 1H), 8.31 (s, 1H), 7.65 (d, J = 9.3 Hz, 1H), 7.59 (dd, J = 7.8 Hz, J = 1.8 Hz, 1H), 7.35 (s, 1H), 7.31 (d, J = 7.8 Hz, 1H), 7.26-7.20 (m, 2H), 6.68 (d, J = 9.3 Hz, 1H), 5.70 (bs, 2H), 3.83 (s, 3H), 2.45 (s, 3H). LC-MS: m/z 348.1 (M + 1)⁺. |
| 64 | 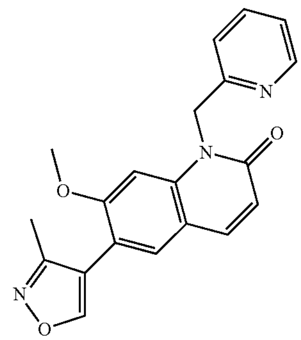 [SMILES: COc1cc2c(ccc(=O)n2Cc2ccccn2)cc1-c1conc1C] | ¹H NMR (CDCl₃, 300 MHz): δ 8.85-8.78 (m, 1H), 8.46 (s, 1H), 7.97 (dt, J = 8.1 & 1.5 Hz, 1H), 7.75 (d, J = 9.3 Hz, 1H), 7.56 (t, J = 6.0 Hz, 1H), 7.60 (d, J = 7.8 Hz, 1H), 7.48 (s, 1H), 6.99 (s, 1H), 6.74 (d, J = 9.3 Hz, 1H), 5.98 (s, 2H), 3.83 (s, 3H), 2.32 (s, 3H); LC-MS: m/z 348.2 (M + 1)⁺. |
| 65 | 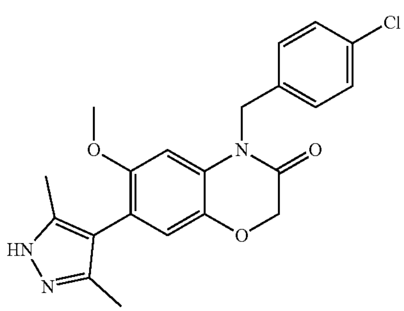 [SMILES: COc1cc2c(cc1-c1c(C)n[nH]c1C)OCC(=O)N2Cc1ccc(Cl)cc1] | ¹H NMR (400 MHz, DMSO-d₆): δ 12.30-12.10 (bs, 1H), 7.44-7.39 (m, 4H), 6.75 (s, 1H), 6.68 (s, 1H), 5.21 (s, 2H), 4.74 (s, 2H), 3.56 (s, 3H), 1.98 (s, 6H); LC-MS: m/z 398.2 (M + 1)⁺. |
| 66 | 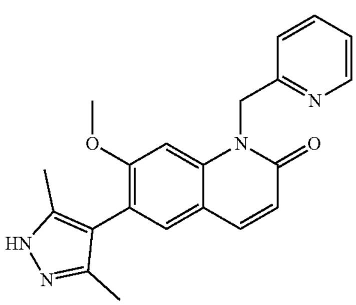 [SMILES: COc1cc2c(ccc(=O)n2Cc2ccccn2)cc1-c1c(C)n[nH]c1C] | ¹H NMR (400 MHz, DMSO-d₆): δ 12.19 (s, 1H), 8.53 (d, J = 3.4, 1H), 7.89 (d, J = 9.8 Hz, 1H), 7.76 (t, J = 7.8 Hz, 1H), 7.47 (s, 1H), 7.30 (d, J = 7.4 Hz, 2H), 7.05 (s, 1H), 6.54 (d, J = 9.3 Hz, 1H), 5.63 (s, 2H), 3.69 (s, 3H), 2.00 (s, 6H); LC-MS: m/z 361.2 (M + 1)⁺. |
| 67 | 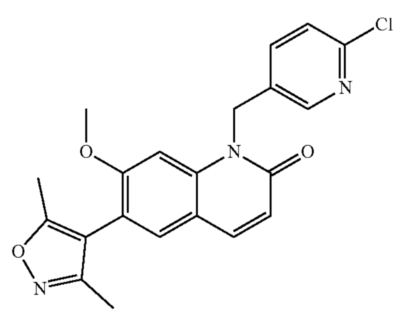 [SMILES: COc1cc2c(ccc(=O)n2Cc2ccc(Cl)nc2)cc1-c1c(C)noc1C] | ¹H NMR (400 MHz, DMSO-d₆): δ 8.50 (d, J = 8.5 Hz, 1H), 7.92 (d, J = 9.3 Hz, 1H), 7.74 (d, J = 6.9 Hz, 1H), 7.65 (s, 1H), 7.49 (d, J = 8.4 Hz, 1H), 7.00 (s, 1H), 6.60 (d, J = 9.2 Hz, 1H), 5.63 (s, 2H), 3.81 (s, 3H), 2.25 (s, 3H), 2.06 (s, 3H); LC-MS: m/z 396.2 (M + 1)⁺. |

| Compound No. | Structure | Characterization Data |
|---|---|---|
| 68 | 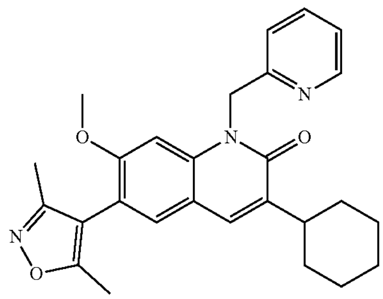 [SMILES: COc1cc2c(cc1-c1c(C)noc1C)cc(C1CCCCC1)c(=O)n2Cc1ccccn1] | $^1$H NMR (400 MHz, DMSO-d$_6$): δ 8.53 (d, J = 4.4 Hz, 1H), 7.78-7.74 (m, 1H), 7.72 (s, 1H), 7.58 (s, 1H), 7.31-7.27 (m, 2H), 7.10 (s, 1H), 5.66 (s, 2H), 3.72 (s, 3H), 2.86-2.81 (m, 1H), 2.24 (s, 3H), 2.05 (s, 3H), 1.90-1.72 (m, 6H), 1.41-1.28 (m, 4H); LC-MS: m/z 444.3 (M + 1)$^+$. |
| 69 | 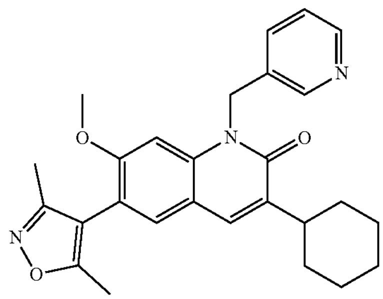 [SMILES: COc1cc2c(cc1-c1c(C)noc1C)cc(C1CCCCC1)c(=O)n2Cc1cccnc1] | $^1$H NMR (400 MHz, DMSO-d$_6$): δ 8.63 (s, 1H), 8.47 (bs, 1H), 7.73 (s, 1H), 7.68-7.66 (m, 1H), 7.60 (s, 1H), 7.38-7.36 (m, 1H), 7.0 (s, 1H), 5.66 (s, 2H), 3.77 (s, 3H), 2.85-2.62 (m, 1H), 2.24 (s, 3H), 2.05 (s, 3H), 1.91-1.72 (m, 6H), 1.45-1.29 (m, 4H); LC-MS: m/z 444.3 (M + 1)$^+$. |

NOTE:
Synthesis of Compound 60 comprises deprotection reaction according to the procedure depicted in below step:

Deprotection (for Compound-60); 7-(3,5-dimethyl-isoxazol-4-yl)-6-methoxy-4-(piperidin-4-ylmethyl)-2H-benzo[b][1,4]oxazin-3(4H)-one To an ice-cooled solution of tert-butyl 4-((7-(3,5-dimethylisoxazol-4-yl)-6-methoxy-3-oxo-2H-benzo[b][1,4]oxazin-4(3H)-yl)methyl)piperidine-1-carboxylate (0.20 g, 0.42 mmol) in DCM (10 mL) was add TFA (6.0 mL, 39.20 mmol) and stirred at same temperature for 1 h. Reaction mixture was concentrated in vacuo, and residue was triturated with hexane to afford a white solid. The solid was suspended in DCM (5 mL) and at 0° C. was added saturated aq. NaHCO$_3$ solution (1.0 mL), stirred for 1 h at same temperature. The organic layer separated, dried over Na$_2$SO$_4$, concentrated in vacuo to afford the title product as an off white semi solid (0.01 g, 6%).

Similarly synthesis Compound-61 comprises debenzylation reaction according to the procedure depicted hereinafter.

Debenzylation (for Compound-61): N-(4-(6-hydroxypyridin-3-yl)-5-methoxy-2-methylphenyl)-N-(pyridin-2-ylmethyl) acetamide In a 25 mL single neck round bottom flask, a stirred solution 6-(6-(benzyloxy)pyridin-3-yl)-7-methoxy-1-(pyridin-2-ylmethyl)quinolin-2(1H)-one (0.040 g, 0.08 mmol) in MeOH (3 mL) was treated with Pd/C (10%, 0.050 g) at RT under nitrogen atmosphere. The suspension was hydrogenated (balloon pressure) at RT for 30 min. Upon completion of reaction (TLC), the reaction mixture was filtered and filtrate was concentrated under reduced pressure to give title compound as an off white solid (0.010 g, 30.3%).

Example-VIII: Synthesis of 7-(3,5-dimethylisoxazol-4-yl)-4-((6-hydroxypyridin-3-yl)methyl)-6-methoxy-2H-benzo[b][1,4]oxazin-3(4H)-one (Compound-70)

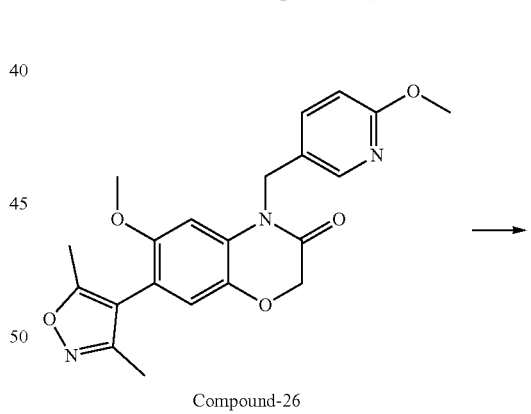

Compound-26

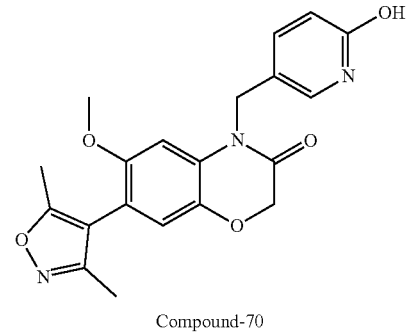

Compound-70

A solution of compound-26 (0.04 g, 0.10 mmol) in 33% HBr in AcOH (3.0 mL) was heated at 100° C. in a sealed tube for 6 h. After completion of reaction, the reaction was quenched by the addition of water (10 mL) followed by saturated aq. sodium bicarbonate solution (20 mL) and extracted with 10% MeOH:DCM (100 mL). The organic layer was washed with water (50 mL), brine (50 mL), dried over sodium sulphate and concentrated under reduced pressure. The residue was purified by preparative TLC to isolate the title product as a brown solid (5 mg, 13%). $^1$H NMR (400 MHz, CDCl$_3$): δ 7.52 (m, 1H), 7.32 (s, 1H), 6.79 (s, 1H), 6.60 (d, J=9.6 Hz, 1H), 6.49 (s, 1H), 4.94 (s, 2H), 4.66 (s, 2H), 3.67 (s, 3H), 2.29 (s, 3H), 2.15 (s, 3H); LC-MS: m/z 382.1 (M+1)$^+$.

Example-IX: Synthesis of 7-(3,5-dimethylisoxazol-4-yl)-6-(2-methoxyethoxy)-4-(pyridin-4-ylmethyl)-2H-benzo[b][1,4]oxazin-3(4H)-one (Compound-71)

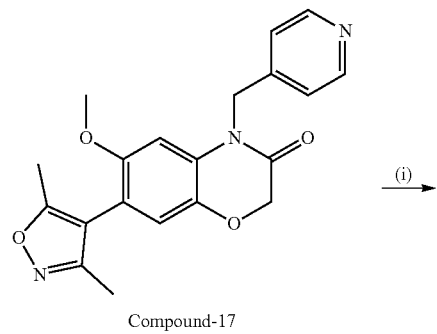

Compound-17

(i)

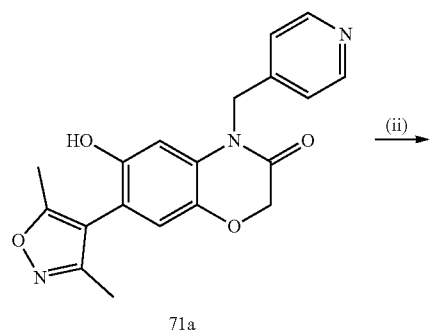

71a

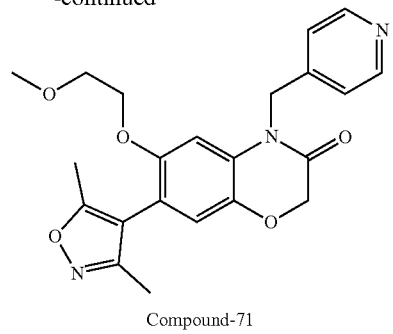

Compound-71

Step-(i): Synthesis of 7-(3,5-dimethylisoxazol-4-yl)-6-hydroxy-4-(pyridin-4-ylmethyl)-2H-benzo[b][1,4]oxazin-3(4H)-one To an ice cooled solution of compound-17 (0.10 g, 0.27 mmol) in DCM (4.0 mL) was added BBr$_a$(1.0M in DCM, 1 mL) and stirred at 100° C. for 16 h. After completion of reaction, the reaction was quenched by the addition of aq. sodium bicarbonate solution and extracted with DCM (50 mL). The organic layer was washed with water (50 mL), brine (50 mL), dried over sodium sulphate and concentrated. The residue was purified by prep. TLC to afford the title compound as off-white solid (0.080 g, 84%). $^1$H NMR (400 MHz, CDCl$_3$) 8.46-8.44 (m, 2H), 7.20-7.19 (m, 2H), 6.77 (s, 1H), 6.39 (s, 1H), 5.14 (s, 2H), 4.74 (s, 2H), 2.32 (s, 3H), 2.18 (s, 3H): ES-MS: m/z 350.2 (M−1)$^-$.

Step-(ii): Synthesis of 7-(3,5-dimethylisoxazol-4-yl)-6-(2-methoxyethoxy)-4-(pyridin-4-ylmethyl)-2H-benzo[b][1,4]oxazin-3(4H)-one To a solution of compound-71a (0.08 g, 0.23 mmol) in DMF (3.0 mL) were added K$_2$CO$_3$ (0.095 g, 0.069 mmol) followed by 1-bromo-2-methoxyethane (0.064 g, 0.46 mmol) and stirred at 50° C. for 16 h. After completion of reaction, the reaction was diluted with water (10 mL) and extracted with EtOAc (50 mL). The organic layer was washed with water (50 mL), brine (50 mL), dried over sodium sulphate and concentrated. The residue was purified by prep. TLC to afford the title compound as white solid (0.010 g, 11%). $^1$H NMR (400 MHz, CDCl$_3$) δ 8.61 (d, J=−5.4 Hz, 2H), 7.22 (d, J=5.8 Hz, 2H), 6.80 (s, 1H), 6.44 (s, 1H), 5.17 (s, 2H), 4.75 (s, 2H), 3.78 (t, J=4.6 Hz, 2H), 3.50 (t, J=4.4 Hz, 2H), 3.27 (s, 3H), 2.29 (s, 3H), 2.16 (s, 3H); LC-MS: m/z 410.2 (M+1)$^+$.

The below compounds were prepared by procedure similar to any or both of the steps depicted in Example-IX with appropriate variations in reactants, quantities of reagents and reaction conditions. The physiochemical characteristics of the compounds are summarized herein below table.

| Compound No. | Structure | Characterization Data |
|---|---|---|
| 72 | 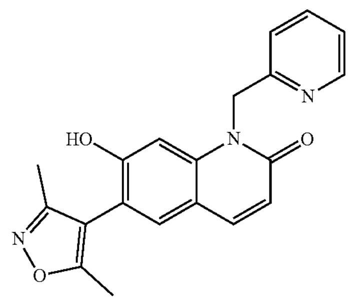 [SMILES: Cc1noc(C)c1-c1cc2ccc(=O)n(Cc3ccccn3)c2cc1O] | $^1$H NMR (300 MHz, CDCl$_3$): δ 9.8 (bs, 1H), 8.16-814 (m, 1H), 7.71-7.65 (m, 2H), 7.32 (s, 1H), 7.17-7.14 (m, 2H), 6.94 (s, 1H), 6.55 (d, J = 9.0 Hz, 1H), 5.65 (s, 2H), 3.34 (s, 3H), 3.20 (s, 3H); LC-MS: m/z 348.1 (M + 1)$^+$. |
| 73 | 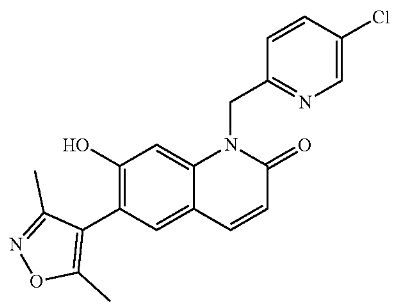 [SMILES: Cc1noc(C)c1-c1cc2ccc(=O)n(Cc3ccc(Cl)cn3)c2cc1O] | $^1$H NMR (400 MHz, DMSO-d$_6$): δ 10.45 (s, 1H), 8.59 (d, J = 2.4 Hz, 1H), 7.90 (dd, J$_1$ = 2.4 Hz, J$_2$ = 8.8 Hz, 1H), 7.87 (d, J = 9.8 Hz, 1H), 7.56 (s, 1H), 7.24 (d, J = 8.3 Hz, 1H), 6.81 (s, 1H), 6.50 (d, J = 9.8 Hz, 1H), 5.48 (s, 2H), 2.25 (s, 3H), 2.09 (s, 3H); LC-MS: m/z 382.1 (M + 1)$^+$. |
| 74 | 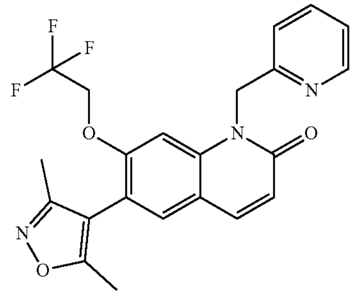 [SMILES: Cc1noc(C)c1-c1cc2ccc(=O)n(Cc3ccccn3)c2cc1OCC(F)(F)F] | $^1$H NMR (300 MHz, CDCl$_3$): δ 8.58 (d, J = 4.2 Hz, 1H), 7.69-7.63 (m, 2H), 7.45 (s, 1H), 7.42-7.41 (m, 1H), 7.31 (s, 1H), 7.25-7.22 (m, 1H), 6.74 (d, J = 9.3 Hz, 1H), 5.66 (s, 2H), 4.41-4.33 (m, 2H), 2.27 (s, 3H), 2.13 (s, 3H); LC-MS: m/z 430.1 (M + 1)$^+$. |
| 75 | 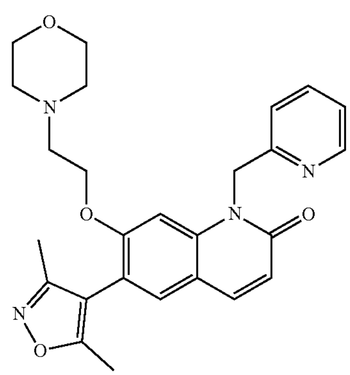 [SMILES: Cc1noc(C)c1-c1cc2ccc(=O)n(Cc3ccccn3)c2cc1OCCN1CCOCC1] | $^1$H NMR (300 MHz, CDCl$_3$): δ 8.57 (d, J = 4.8 Hz, 1H), 7.67-7.61 (m, 2H), 7.34 (d, J = 7.8 Hz, 1H), 7.23-7.20 (m, 3H), 6.69 (d, J = 9.3 Hz, 1H), 5.67 (s, 2H), 4.07 (t, J = 5.4 Hz, 2H), 3.74-3.64 (m, 4H), 2.68 (t, J = 6.3 Hz, 2H), 2.45-2.42 (m, 4H), 2.27 (s, 3H), 2.14 (s, 3H); LC-MS: m/z 461.2 (M + 1)$^+$. |
| 76 | 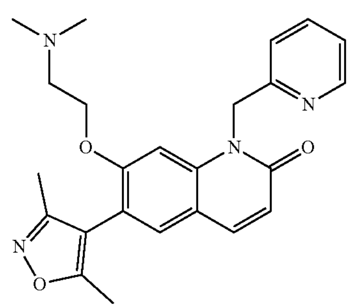 [SMILES: Cc1noc(C)c1-c1cc2ccc(=O)n(Cc3ccccn3)c2cc1OCCN(C)C] | $^1$H NMR (300 MHz, CDCl$_3$): δ 8.57 (d, J = 4.8 Hz, 1H), 7.67-7.60 (m, 2H), 7.34 (d, J = 7.8 Hz, 1H), 7.23-7.18 (m, 3H), 6.69 (d, J = 9.3 Hz, 1H), 5.67 (s, 2H), 4.04 (t, J = 5.7 Hz, 2H), 2.62 (t, J = 5.7 Hz, 2H), 2.27 (s, 3H), 2.23 (s, 6H), 2.13 (s, 3H); LC-MS: m/z 419.3 (M + 1)$^+$. |

| Compound No. | Structure | Characterization Data |
|---|---|---|
| 77* | 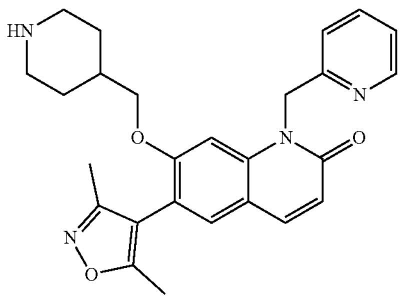 [SMILES: Cc1noc(C)c1-c1cc2ccc(=O)n(Cc3ccccn3)c2cc1OCC1CCNCC1] | ¹H NMR (CD₃OD, 300 MHz): δ 8.83 (s, 1H), 8.48-8.44 (m, 1H), 8.03 (d, J = 9.6 Hz, 1 H), 7.94 (bs, 1H), 7.76 (d, J = 7.6 Hz, 1 H), 7.65 (s, 1H), 7.21 (s, 1H), 6.66 (d, J = 9.6 Hz, 1 H), 6.00 (s, 2H), 4.05 (s, 2H), 3.73-3.66 (m, 1H) 3.39-3.34 (m, 2H), 3.01-2.95 (m, 2H), 2.29 (s, 3H), 2.12 (s, 3H), 1.92-1.88 (m, 2H), 1.52-1.49 (m, 2H); LC-MS: m/z 445.05 (M + 1)⁺. |
| 78 | 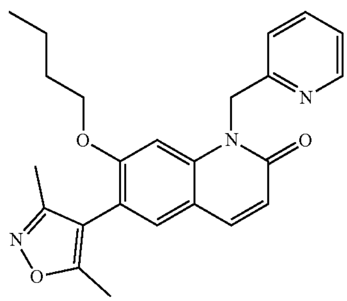 [SMILES: CCCCOc1cc2c(ccc(=O)n2Cc2ccccn2)cc1-c1c(C)noc1C] | ¹HNMR (300 MHz, CDCl₃): δ 8.57 (d, J = 4.2 Hz, 1H), 7.67-7.60 (m, 2H), 7.34 (d, J = 8.1 Hz, 1H), 7.26-7.17 (m, 3H), 6.68 (d, J = 9.6 Hz, 1H), 5.68 (s, 2H), 3.93 (t, J = 6.9 Hz, 2H), 2.26 (s, 3H), 2.12 (s, 3H), 1.68 (t, J = 6.9 Hz, 2H), 1.39-1.32 (m, 2H), 0.90 (t, J = 6.9 Hz, 3H); LC-MS: m/z 404.1 (M + 1)⁺. |
| 79 | 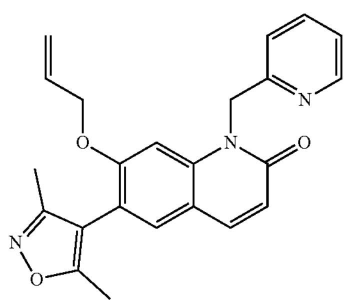 [SMILES: C=CCOc1cc2c(ccc(=O)n2Cc2ccccn2)cc1-c1c(C)noc1C] | ¹HNMR (300 MHz, CDCl₃): δ 8.61 (d, J = 3.0 Hz, 1H), 7.97-7.90 (m, 2H), 7.58 (s, 1H), 7.46 (t, J = 3.0 Hz, 6.0 Hz, 1H), 7.37 (d, J = 6.0 Hz, 1H), 7.05 (s, 1H), 6.65 (d, J = 9.0 Hz, 1H), 5.88-5.85 (m, 1H), 5.77 (s, 2H), 5.22-5.10 (m, 2H), 4.56-4.54 (m, 2H), 2.27 (s, 3H), 2.11 (s, 3H); LC-MS: m/z 388.2 (M + 1)⁺. |
| 80 | 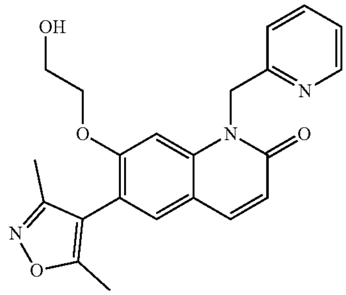 [SMILES: Cc1noc(C)c1-c1cc2ccc(=O)n(Cc3ccccn3)c2cc1OCCO] | ¹H NMR (400 MHz, DMSO-d₆) δ 8.52 (d, J = 3.9 Hz, 1H), 7.90 (d, J = 9.8 Hz, 1H), 7.77-7.75 (m, 1H), 7.61 (s, 1H), 7.31-7.28 (m, 2H), 7.09 (s, 1H), 6.59 (d, J = 9.3 Hz, 1H), 5.63 (s, 2H), 4.83 (t, J = 5.3 Hz, 1H), 3.96 (t, J = 4.9 Hz, 2H), 3.64-3.60 (m, 2H), 2.27 (s, 3H), 2.10 (s, 3H); ES-MS: m/z 392.2 (M + 1)⁺. |
| 81 | 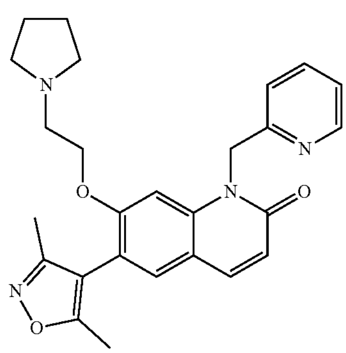 [SMILES: Cc1noc(C)c1-c1cc2ccc(=O)n(Cc3ccccn3)c2cc1OCCN1CCCC1] | ¹H NMR (300 MHz, CDCl₃) δ 8.57 (d, J = 4.2 Hz, 1H), 7.67-7.59 (m, 2H), 7.33-7.18 (m, 4H), 6.68 (d, J = 9.6 Hz, 1H), 5.67 (s, 2H), 4.07 (t, J = 5.7 Hz, 2H), 2.80 (t, J = 5.4 Hz, 2H), 2.47 (m, 4H), 2.27 (s, 3H), 2.14 (s, 3H), 1.74 (m, 4H); LC-MS: m/z 445.2 (M + 1)⁺. |

| Compound No. | Structure | Characterization Data |
|---|---|---|
| 82* | 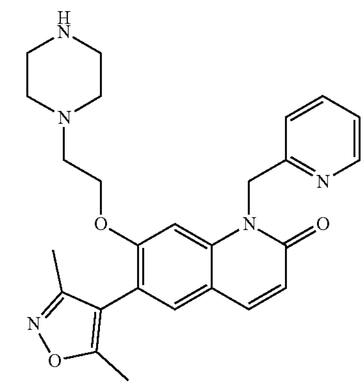 [SMILES: Cc1noc(C)c1-c1cc2ccc(=O)n(Cc3ccccn3)c2cc1OCCN1CCNCC1] | ¹H NMR (400 MHz, DMSO-d₆): δ 8.51 (d, J = 4.0 Hz, 1H), 7.90 (d, J = 9.2 Hz, 1H), 7.77 (t, J = 7.6 Hz, 1H), 7.61 (s, 1H), 7.31-7.28 (m, 2H), 7.10 (s, 1H), 6.57 (d, J = 9.6 Hz, 1H), 5.64 (s, 2H), 4.04 (t, J = 5.6 Hz, 2H), 2.68-2.64 (m, 5H), 2.61-2.59 (m, 2H), 2.28-2.26 (m, 7H), 2.10 (s, 3H); LC-MS: m/z 460.3 (M + 1)⁺. |
| 83 | 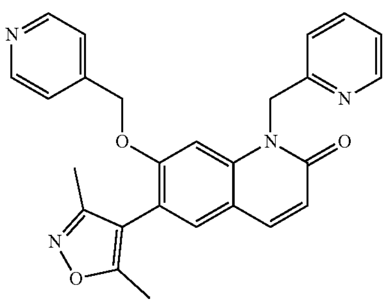 [SMILES: Cc1noc(C)c1-c1cc2ccc(=O)n(Cc3ccccn3)c2cc1OCc1ccncc1] | ¹H NMR (400 MHz, DMSO-d₆): δ 8.46 (d, J = 5.4 Hz, 2H), 8.41 (d, J = 4.4 Hz, 1H), 7.91 (d, J = 9.3 Hz, 1H), 7.71-7.69 (m, 1H), 7.67 (s, 1H), 7.26-7.12 (m, 5H), 6.58 (d, J = 9.3 Hz, 1H), 5.57 (s, 2H), 5.22 (s, 2H), 2.26 (s, 3H), 2.07 (s, 3H); LC-MS: m/z 439.2 (M + 1)⁺. |
| 84 | 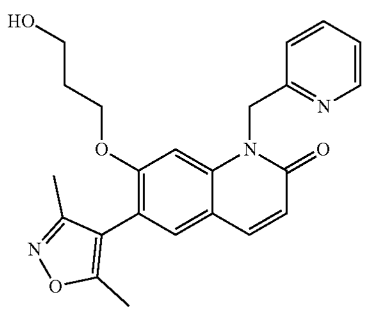 [SMILES: Cc1noc(C)c1-c1cc2ccc(=O)n(Cc3ccccn3)c2cc1OCCCO] | ¹H NMR (400 MHz, DMSO-d₆): δ 8.51 (d, J = 4.4 Hz, 1H), 7.90 (d, J = 9.8 Hz, 1H), 7.76 (t, J = 7.8 Hz, 1H), 7.60 (s, 1H), 7.30 (d, J = 7.8 Hz, 2H), 7.11 (s, 1H), 6.57 (d, J = 9.3 Hz, 1H), 5.63 (s, 2H), 4.51 (t, J = 4.8 Hz, 1H), 4.0 (t, J = 6.4 Hz, 2H), 3.42-3.38 (m, 2H), 2.24 (s, 3H), 2.06 (s, 3H), 1.77-1.72 (m, 2H); LC-MS: m/z 406.2 (M + 1)⁺. |

Note:
Synthesis of Compound 77 comprises deprotection reaction according to the procedure depicted in below step:

Deprotection Reaction (for Compound-77): 6-(3,5-dimethylisoxazol-4-yl)-7-(piperidin-4-ylmethoxy)-1-(pyridin-2-ylmethyl)quinolin-2(1H)-one hydrochloride A solution of tert-butyl 4-(((6-(3,5-dimethylisoxazol-4-yl)-2-oxo-1-(pyridin-2-ylmethyl)-1,2-dihydroquinolin-7-yl)oxy)methyl)piperidine-1-carboxylate (0.05 g, 0.0919 mmol) in 1,4-dioxane. HCl (2 mL) was stirred at room temperature for 4 h. After completion of reaction, the solvent was removed under reduced pressure, residue was triturated with ether and hexane to give the title compound (0.01 g, 22.6%).

Similarly synthesis of Compound 82 comprises deprotection reaction according to the procedure depicted herein after.

Deprotection Reaction (for Compound-82): 6-(3,5-dimethylisoxazol-4-yl)-7-(2-(piperazin-1-yl)ethoxy)-1-(pyridin-2-ylmethyl) quinolin-2(1H)-one To a cooled solution of ten-butyl 4-(2-((6-(3,5-dimethylisoxazol-4-yl)-2-oxo-1-(pyridin-2-ylmethyl)-1,2-dihydroquinolin-7-yl)oxy)ethyl)piperazine-1-carboxylate (0.05 g, 0.09 mmol) in DCM (3 mL) was added TFA (0.5 mL) and stirred at room temperature for 2 h. The reaction mixture concentrated, residue was diluted with DCM (50 mL) and washed with sat NaHCO₃(50 mL), water (50 mL), dried over sodium sulphate and concentrated invacuo. The residue was washed with diethyl ether to afford the title compound as brown solid (0.015 g, 37%).

Example-X: Synthesis of 6-(3,5-dimethylisoxazol-4-yl)-1-(pyridin-2-ylmethyl)-7-(trifluoro methoxy)quinolin-2(1H)-one (Compound-85)

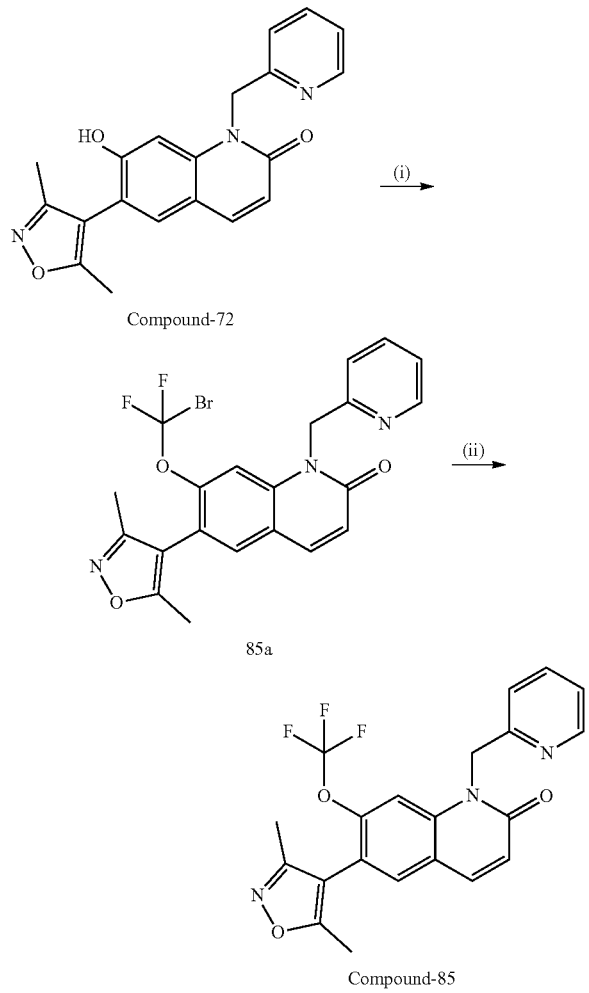

Step-(i): Synthesis of 7-(bromodifluoromethoxy)-6-(3,5-dimethylisoxazol-4-yl)-1-(pyridin-2-ylmethyl)quinolin-2(1H)-one The process of this adopted from step-(ii) of compound-71 (Example-IX) to give the titled compound as pale yellow solid (0.05 g, 36%). $^1$H NMR (300 MHz, CDCl$_3$): δ 8.58 (d, J=4.8 Hz, 1H), 7.74-7.63 (m, 3H), 7.42 (s, 1H), 7.29 (d, J=5.1 Hz, 1H), 7.20-7.19 (m, 1H), 6.87 (d, J=9.6 Hz, 1H), 5.66 (s, 2H), 2.29 (s, 3H), 2.15 (s, 3H); $^{19}$F NMR (300 MHz, CDCl$_3$): δ 15.9: LC-MS: m/z 477.9 (M+1)$^+$.

Step-(ii): Synthesis of 6-(3,5-dimethylisoxazol-4-yl)-1-(pyridin-2-ylmethyl)-7-(trifluoro methoxy)quinolin-2(1H)-one In a 50 mL polypropylene flask, a stirred solution of 7-(bromodifluoromethoxy)-6-(3,5-dimethylisoxazol-4-yl)-1-(pyridin-2-ylmethyl)quinolin-2(1H)-one (0.05 g, 0.105 mmol) in DCM (5 mL) was treated with AgBF$_4$ (0.061 g, 0.315 mmol), at −78° C. for 30 min. The reaction mixture was stirred at RT for 12 h. The reaction mixture was diluted with cold saturated NaHCO$_3$ and extracted with DCM. The organic extract was washed with water and brine. The organic layer was separated and dried over Na$_2$SO$_4$. The solution was concentrated under reduced pressure to give crude compound. The residue obtained was purified by silica gel preparative TLC (50% EtOAc/Hexane) to yield the title compound as an off white solid (0.016 g, 37%). $^1$H NMR (300 MHz, CDCl$_3$): δ 8.58 (d, J=4.2 Hz, 1H), 7.72-7.61 (m, 3H), 7.41 (s, 1H), 7.33 (d, J=8.1 Hz, 1H), 7.23-7.19 (m, 1H), 6.84 (d, J=9.6 Hz, 1H), 5.64 (s, 2H), 2.28 (s, 3H), 2.14 (s, 3H): $^{19}$F NMR (300 MHz, CDCl$_3$): δ −57.95; LC-MS: m/z 416.4 (M+1)$^+$.

Example-XI: Synthesis of 6-(3,5-dimethylisoxazol-4-yl)-7-(piperidin-4-yloxy)-1-(pyridin-2-ylmethyl)quinolin-2(1H)-one hydrochloride (Compound-86)

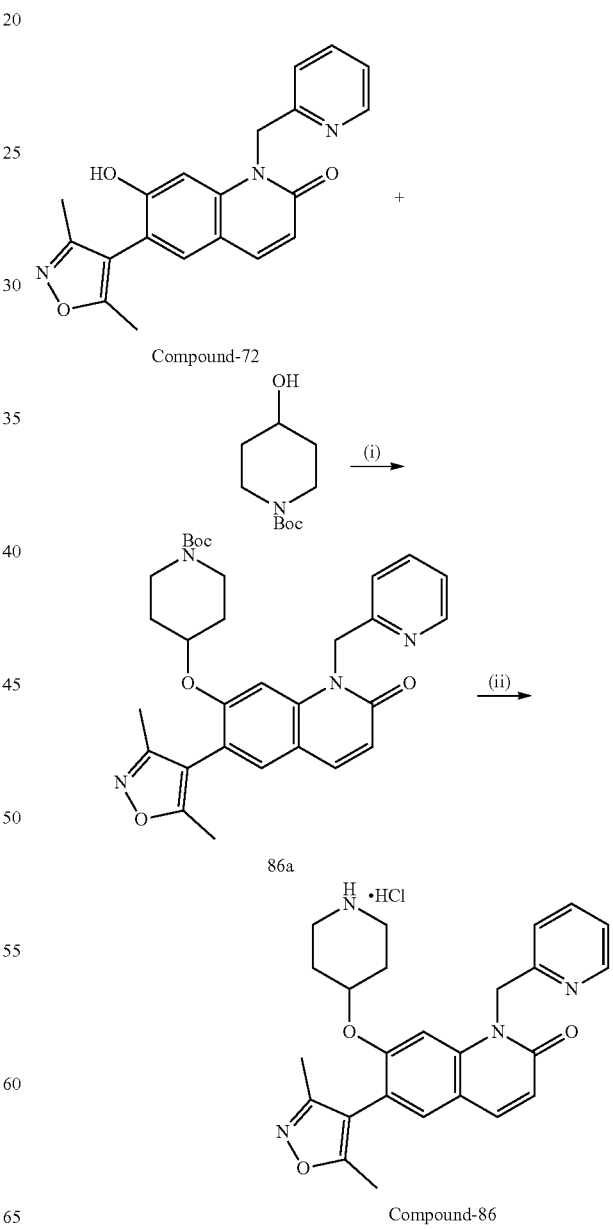

Step-(i): Synthesis of tert-butyl 4-((6-(3,5-dimethyl-isoxazol-4-yl)-2-oxo-1-(pyridin-2-ylmethyl)-1,2-dihydroquinolin-7-yl)oxy)piperidine-1-carboxylate To a solution of compound-72 (0.07 g, 0.20 mmol) in dry THF (8 mL) was added tert-butyl 4-hydroxypiperidine-1-carboxylate (0.05 g, 0.22 mmol), triphenylphosphine (0.16 g, 0.6 mmol), and DIAD (0.12 mL, 0.6 mmol), and stirred at room temperature 16 h. The reaction mixture diluted with water and extracted with EtOAc (50 mL×2), combined organic layer washed with brine (50 mL), dried over sodium sulphate and concentrated. The residue was purified by silica gel (60-120 mesh) column chromatography (elution 20-40% EtOAc-hexane) to afford title compound (0.05 g, 47%); LC-MS: m/z 531.3 (M+1)$^+$.

Step-(ii): Synthesis of 6-(3,5-dimethylisoxazol-4-yl)-7-(piperidin-4-yloxy)-1-(pyridin-2-ylmethyl)quinolin-2(1H)-one hydrochloride The process of this adopted from deprotection reaction of compound-77 (Example-IX). $^1$H NMR (400 MHz, CD$_3$OD): δ 8.69 (d, J=5.6 Hz, 1H), 8.16 (m, 1H), 7.98 (d, J=12.0 Hz, 1H), 7.67-7.65 (m, 2H), 7.57 (d, J=8.0 Hz, 1H), 7.26 (s, 1H), 6.66 (d, J=8.0 Hz, 1H), 5.86 (s, 2H), 5.00-4.80 (m, 1H), 3.18-3.11 (m, 2H), 3.05-3.01 (m, 2H), 2.29 (s, 3H), 2.13 (s, 3H), 2.05-2.03 (m, 2H), 1.84-1.82 (m, 2H); LC-MS: m/z 431.1 (M+1)$^+$.

The below compounds were prepared by procedure similar to any or both of the steps depicted in Example XI with appropriate variations in reactants, quantities of reagents and reaction conditions. The physiochemical characteristics of the compounds are summarized herein

| Compound No. | Structure | Characterization Data |
|---|---|---|
| 87 | 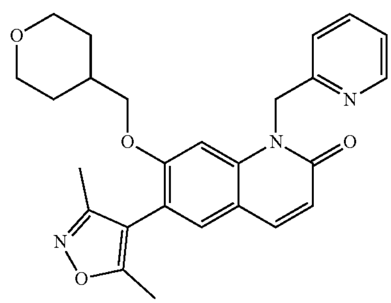 [SMILES: Cc1noc(C)c1-c1cc2ccc(=O)n(Cc3ccccn3)c2cc1OCC1CCOCC1] | $^1$H NMR (300 MHz, CDCl$_3$): δ 8.56 (d, J = 4.2 Hz, 1H), 7.66-7.61 (m, 2H), 7.34 (d, J = 7.8 Hz, 1H), 7.23-7.20 (m, 3H), 6.68 (d, J = 9.6 Hz, 1H), 5.68 (s, 2H), 3.98-3.93 (m, 2H), 3.76 (d, J = 6.9 Hz, 2H), 3.35 (m, 2H), 2.25 (s, 3H), 2.11 (s, 3H), 1.95-1.91 (m, 1H), 1.39-1.25 (m, 4H); LC-MS: m/z 446.3 (M + 1)$^+$. |
| 88 | 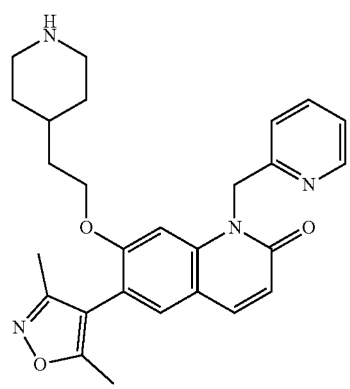 [SMILES: Cc1noc(C)c1-c1cc2ccc(=O)n(Cc3ccccn3)c2cc1OCCC1CCNCC1] | $^1$H NMR (400 MHz, CDCl$_3$): δ 8.78 (d, J = 5.6 Hz, 1H), 8.35 (m, 1H), 8.00 (d, J = 10 Hz, 1H), 7.85 (m, 1H), 7.70 (d, J = 8.0 Hz, 1H), 7.63 (s, 1H), 7.15 (s, 1H), 6.64 (d, J = 9.6 Hz, 1H), 5.92 (s, 2H), 4.19-4.14 (m, 2H), 2.88 (t, J = 12.8 Hz, 2H), 2.27 (s, 3H), 2.11 (s, 3H), 1.85 (d, J = 14 Hz, 2H), 1.71-1.66 (m, 2H), 1.66-1.33 (m, 2H), 1.26 (m, 3H); LC-MS: m/z 459.0 (M + 1)$^+$. |
| 89 | 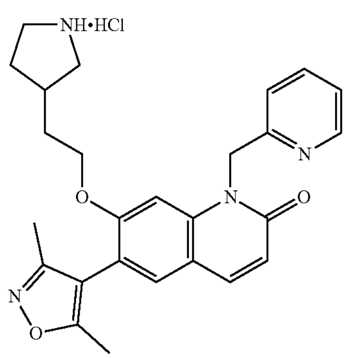 | 1H NMR (300 MHz, CD$_3$OD): 8.82 (d, J = 5.7 Hz, 1H), 8.45-8.40 (m, 1H), 8.03 (d, J = 9.6 Hz, 1H), 7.96-7.90 (m, 1H), 7.76 (d, J = 8.1 Hz, 1H), 7.67 (s, 1H), 7.19 (s, 1H), 6.66 (d, J = 9.6 Hz, 1H), 5.99 (s, 2H), 4.30-4.20 (m, 2H), 3.80-3.60 (m, 2H), 3.25-3.10 (m, 1H), 2.75-2.65 (m, 1H), 2.40-2.30 (m, 1H), 2.31 (s, 3H), 2.14 (s, 3H), 2.15-2.05 (m, 1H), 1.98-1.85 (m, 2H), 1.70-1.55 (m, 1H); LC-MS: m/z 445.2 (M + 1)$^+$. |

Example-XII: Synthesis of 7-(3,5-dimethylisoxazol-4-yl)-6-methoxy-4-(1-propionylpiperidin-4-yl)methyl)-2H-benzo[b][1,4]oxazin-3(4H)-one (Compound-90)

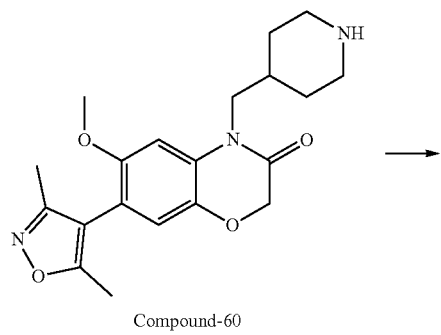

Compound-60

→

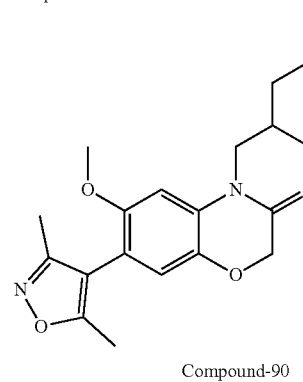

Compound-90

To an ice cooled solution of compound-60 (0.10 g, 0.27 mmol) in DCM (5 mL) were added triethyl amine (0.1 mL, 0.8 mmol) followed by addition of propionyl chloride (0.04 g, 0.40 mmol) drop wise and stirred at RT for 3 h. After completion of reaction, the reaction mixture was diluted with DCM (50 mL) and washed with aq. NaHCO$_3$ solution (20 mL), water (50 mL), brine (20 mL), dried over sodium sulphate and concentrated. The obtained residue was purified by preparative HPLC to afford the title product as an off-white solid (0.08 g, 8%). $^1$H NMR (400 MHz, DMSO-d$_6$): δ 6.92 (s, 1H), 6.90 (s, 1H), 4.62 (s, 2H), 4.40-4.32 (m, 1H), 3.90-3.80 (m, 2H), 3.80-3.75 (m, 4H), 2.80-2.75 (m, 1H), 2.47-2.40 (m, 5H), 2.20-1.80 (m, 5H), 1.72-1.60 (m, 2H), 1.30-1.10 (m, 2H), 0.97 (t, J=7.3 Hz, 3H); LC-MS: m/z 428.3 (M+1)$^+$.

Example-XIII: Synthesis of 7-methoxy-6-(5-methyl-2-oxo-2,3-dihydro-1H-imidazol-1-yl)-1-(pyridin-2-ylmethyl)quinolin-2(1H)-one (Compound-91)

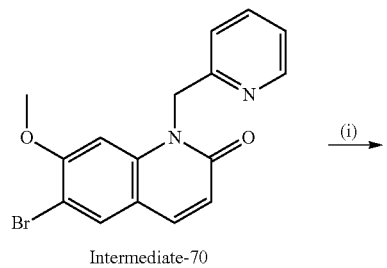

Intermediate-70

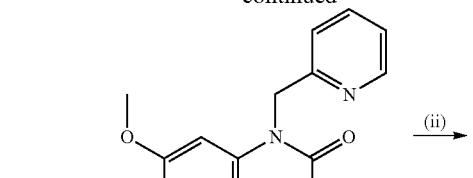

91a

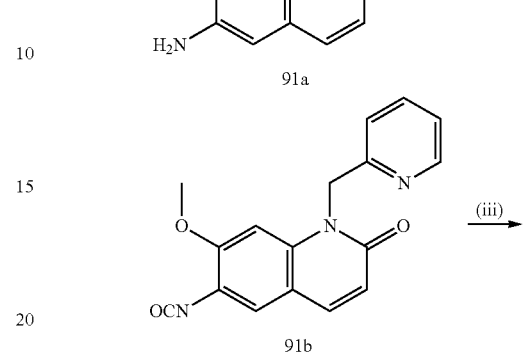

91b

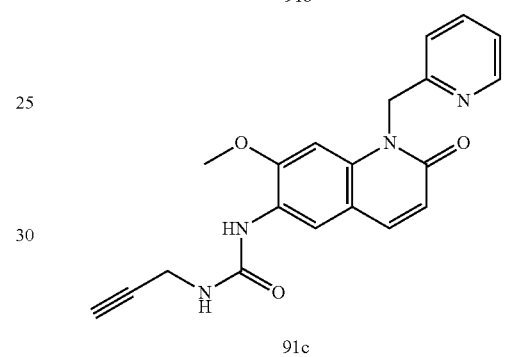

91c

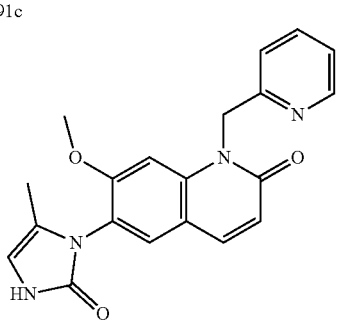

Compound-91

Step-(i): Synthesis of 6-amino-7-methoxy-1-(pyridin-2-ylmethyl)quinolin-2(1H)-one In a 100 mL resealable tube, a solution of 6-bromo-7-methoxy-1-(pyridin-2-ylmethyl)quinolin-2(1H)-one (1.0 g, 2.99 mmol) in DMSO (10 mL), was treated sequentially with sodium azide (0.28 g, 4.2 mmol), CuI (0.54 g, 2.99 mmol) and L-proline (0.50 g, 4.3 mmol) at RT under a nitrogen atmosphere. The resulting mixture was heated overnight at 100° C. Upon completion of the reaction (TLC), the reaction mixture was diluted with cold water and extracted with EtOAc (3×50 mL). The combined organic layers were washed with brine and concentrated under reduced pressure to afford the title compound as pale brown solid (0.60 g, 74%), which was used in the next step without further purification. $^1$H NMR (400 MHz, CDCl$_3$): δ 8.53 (d, J=3.6 Hz, 1H), 7.56-7.51 (m, 2H), 7.20-7.13 (m, 2H), 6.95

(s, 1H), 6.77 (s, 1H), 6.62 (d, J=8.8 Hz, 1H), 5.64 (s, 2H), 3.8 (s, 3H); LC-MS: m/z 282.1 (M+1)+.

Step-(ii): Synthesis of 6-isocyanato-7-methoxy-1-(pyridin-2-ylmethyl)quinolin-2(1H)-one To a solution of triphosgene (0.35 g, 1.24 mmol) in DCM (2 mL) was added drop wise a solution of 6-amino-7-methoxy-1-(pyridin-2-ylmethyl)quinolin-2(1H)-one (0.35 g, 1.24 mmol) in DCM (10 mL) followed by the drop wise addition of triethylamine (0.1 mL, 2.48 mmol)) at RT. The reaction mixture was stirred at RT for 4 h. After completion of the reaction (TLC), the solvent was distilled off under reduced pressure. The residue obtained was used to next step without any purification (0.30 g, crude); LC-MS: m/z 308.1 (M+1)+.

Step-(iii): Synthesis of 1-(7-methoxy-2-oxo-1-(pyridin-2-ylmethyl)-1,2-dihydroquinolin-6-yl)-3-(prop-2-yn-1-yl)urea To a stirred solution of 6-isocyanato-7-methoxy-1-(pyridin-2-ylmethyl)quinolin-2(1H)-one (0.3 g, 0.97 mmol) in dry THF (10 mL) was added propargyl amine (0.059 g, 0.97 mmol) in THF (1 mL) under argon atmosphere at RT. The reaction mixture was stirred for 12 h at RT. The reaction mixture was diluted with water and extracted with EtOAc (3×30 mL). The combined organic extract was washed with brine and concentrated under reduced pressure. The residue obtained was purified by silica gel (60-120 mesh) column chromatography and eluting with 20% EtOAc/Hexane afforded the title compound as a pale yellow solid (0.32 g, crude). LC-MS: m/z 363.4 (M+1)+.

Step-(iv): Synthesis of 7-methoxy-6-(5-methyl-2-oxo-2,3-dihydro-1H-imidazol-1-yl)-1-(pyridin-2-ylmethyl)quinolin-2(1H)-one To a stirred solution of 1-(7-methoxy-2-oxo-1-(pyridin-2-ylmethyl)-1,2-dihydroquinolin-6-yl)-3-(prop-2-yn-1-yl) urea (0.3 g, 0.82 mmol) in MeOH (15 mL) was added 5 N sodium methoxide in MeOH (0.5 mL) at RT under nitrogen atmosphere. The reaction mixture was stirred at reflux temperature for 24 h. After completion of the reaction, was cooled to room temperature and solvent was removed under reduced pressure. The residue obtained was purified by silica gel preparative TLC (5% MeOH/CHCl$_3$) to give the compound as an off white solid (0.01 g, 3.3%). $^1$H NMR (400 MHz, CDCl$_3$): δ 9.79 (s, 1H), 8.51-8.50 (d, J=4.8 Hz, 1H), 7.92 (d, J=9.6 Hz, 1H), 7.76-7.74 (m, 1H), 7.63 (s, 1H), 7.31-7.26 (m, 2H), 7.11 (s, 1H), 6.58 (d, J=8.4 Hz, 1H), 6.18 (s, 1H), 7.74 (d, J=16.8 Hz, 1H), 7.55 (d, 16.8 Hz, 1H), 3.69 (s, 3H), 1.69 (3H); LC-MS: m/z 363.0 (M+1)+.

Example-XIV: Synthesis of 3-(7-methoxy-2-oxo-1-(pyridin-2-ylmethyl)-1,2-dihydroquinolin-6-yl)-4-methyl-1H-pyrrole-25-dione (Compound-92)

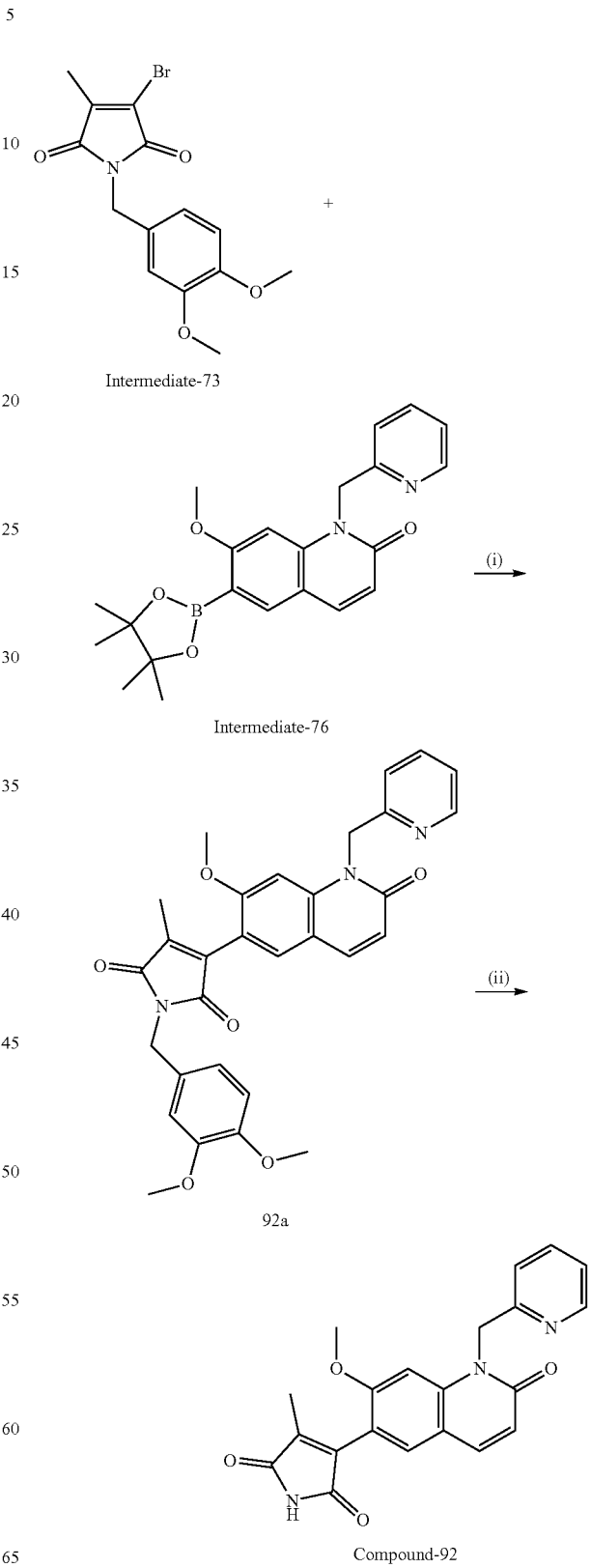

Step-(i): Synthesis of 1-(3,4-dimethoxybenzyl)-3-(7-methoxy-2-oxo-1-(pyridin-2-ylmethyl)-1,2-dihydroquinolin-6-yl)-4-methyl-1H-pyrrole-2,5-dione The process of this step was adopted from example-VII (Compound-17). The desired compound obtained as a crude material (0.10 g); LC-MS: m/z 526.1 (M+1)+.

Step-(ii): Synthesis of 3-(7-methoxy-2-oxo-1-(pyridin-2-ylmethyl)-1,2-dihydroquinolin-6-yl)-4-methyl-1H-pyrrole-2,5-dione A solution of 1-(3,4-dimethoxybenzyl)-3-(7-methoxy-2-oxo-1-(pyridin-2-ylmethyl)-1,2-dihydroquinolin-6-yl)-4-methyl-1H-pyrrole-2,5-dione (0.10 g, 0.19 mmol), anisole (0.1 mL) and $H_2SO_4$ (catalytic amount) in TFA (4 mL) was heated over night at 90° C. Upon completion of the reaction (TLC), the reaction mixture was cooled to RT and diluted with DCM. The organic layer was washed with saturated $NaHCO_3$ solution and dried over anhydrous sodium sulfate, before evaporating under reduced pressure. The obtained residue was purified by silica gel (60-120 mesh) column chromatography and eluting with 5% DCM/MeOH gave the title compound as an off-white solid (0.004 g, 5.6%). $^1$H NMR (400 MHz, $CDCl_3$): δ 8.54-8.53 (m, 1H), 7.95-7.90 (m, 1H), 7.77-7.74 (m, 1H), 7.62 (s, 1H), 7.34-7.27 (m, 2H), 7.07 (s, 1H), 6.67 (d, J=9.3 Hz, 1H), 5.74 (s, 2H), 3.78 (s, 3H), 1.90 (s, 3H); LC-MS: m/z 376.1 (M+1)+.

Example-XV: Synthesis of 6-(3,5-dimethylisoxazol-4-yl)-7-methoxy-1-(pyridin-2-ylmethyl) quinoxalin-2(1H)-one (Compound-93)

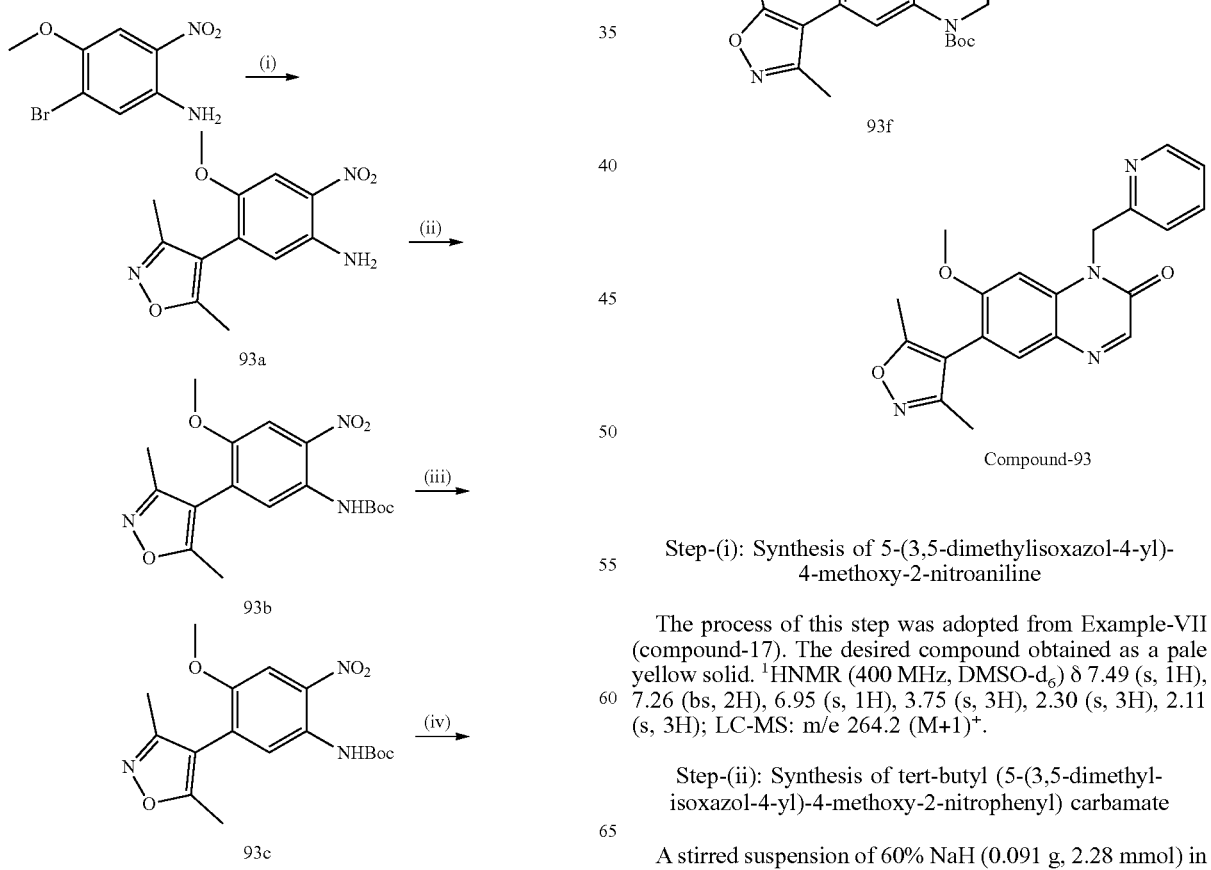

Compound-93

Step-(i): Synthesis of 5-(3,5-dimethylisoxazol-4-yl)-4-methoxy-2-nitroaniline

The process of this step was adopted from Example-VII (compound-17). The desired compound obtained as a pale yellow solid. $^1$HNMR (400 MHz, DMSO-$d_6$) δ 7.49 (s, 1H), 7.26 (bs, 2H), 6.95 (s, 1H), 3.75 (s, 3H), 2.30 (s, 3H), 2.11 (s, 3H); LC-MS: m/e 264.2 (M+1)+.

Step-(ii): Synthesis of tert-butyl (5-(3,5-dimethylisoxazol-4-yl)-4-methoxy-2-nitrophenyl) carbamate A stirred suspension of 60% NaH (0.091 g, 2.28 mmol) in 5 mL of DMF at 0° C. was added 5-(3,5-dimethylisoxazol- 4-yl)-4-methoxy-2-nitroaniline (0.5 g, 1.90 mmol). Stirred at same conditions for 30 min then added Boc-anhydride (0.48 mL, 2.09 mmol). The reaction mixture was stirred for 3 h at room temperature. The reaction mixture was diluted with ethyl acetate and washed with water (100 mL), dried over Na$_2$SO$_4$ and concentration. The obtained residue was purified by column chromatography on silica (20% EtOAc in hexane) to give the desired product as a yellow solid (0.45 g, 65%). $^1$H NMR (400 MHz, DMSO-d$_6$) δ 9.38 (bs, 1H), 7.61 (s, 1H), 7.41 (s, 1H), 3.85 (s, 3H), 2.30 (s, 3H), 2.11 (s, 3H), 1.43 (s, 9H); LC-MS: m/e 364.2 (M+1)$^+$.

Step-(iii): Synthesis of tert-butyl (2-amino-5-(3,5-dimethylisoxazol-4-yl)-4-methoxyphenyl) carbamate A stirred solution of tert-butyl (5-(3,5-dimethylisoxazol-4-yl)-4-methoxy-2-nitrophenyl) carbamate (0.45 g, 1.23 mmol) in 10 mL of MeOH was added 10% Pd—C (0.1 g) and stirred under H$_2$ balloon pressure at RT for 2 h. After completion of reaction, the reaction mixture was filtered through celite pad, washed with methanol. The filtrate was concentrated to afford the title product as pale yellow solid (0.5 g). The crude product was as such taken forward for next step without further purification. $^1$H NMR (400 MHz, DMSO-d$_6$) δ 8.31 (s, 1H), 6.87 (bs, 1H), 6.44 (s, 1H), 5.01 (bs, 2H), 3.65 (s, 3H), 2.21 (s, 3H), 2.03 (s, 3H), 1.43 (s, 9H); LC-MS: m/e 334.2 (M+1)$^+$.

Step-(iv): Synthesis of tert-butyl (5-(3,5-dimethyl-isoxazol-4-yl)-4-methoxy-2-((pyridin-2-ylmethyl)amino)phenyl)carbamate To an ice-cooled solution of tert-butyl (2-amino-5-(3,5-dimethylisoxazol-4-yl)-4-methoxyphenyl)carbamate (0.15 g, 0.45 mmol) in MeOH (10 mL) were add pyridine-2-carboxaldehyde (0.06 mL, 0.67 mmol) and stirred at RT for 2 h. Then the reaction mixture was again cooled to 0° C. and added sodium cyanobornhydride (0.057 g, 0.9 mmol) followed by AcOH (0.02 mL) and stirred at RT for 16 h. After completion of reaction, the reaction mixture was concentrated, diluted with water and extracted with EtOAc (100 mL×2). The combined organic layers were washed with aq. sodium bicarbonate (20 mL), water (200 mL), brine (100 mL), dried over sodium sulphate and concentrated. The residue was purified silica gel (100-200 mesh) to afford the title product (0.1 g, 52%). $^1$H NMR (400 MHz, DMSO-d$_6$): δ 8.54 (d, J=4.4 Hz, 1H), 8.31 (s, 1H), 7.80-7.76 (m, 1H), 7.46 (d, J=7.8 Hz, 1H), 7.30-7.27 (m, 1H), 6.84 (s, 1H), 6.35-6.25 (m, 1H), 5.94 (t, J=5.6 Hz, 1H), 4.47 (d, J=5.4 Hz, 2H), 3.61 (s, 3H), 2.20 (s, 3H), 2.02 (s, 3H), 1.23 (s, 9H); LC-MS: m/z 425.3 (M+1)$^+$.

Step-(v): Synthesis of tert-butyl (2-(2-chloro-N-(pyridin-2-ylmethyl)acetamido)-5-(3,5-dimethyl isoxazol-4-yl)-4-methoxyphenyl)carbamate To an ice-cooled solution of tert-butyl (5-(3,5-dimethyl-isoxazol-4-yl)-4-methoxy-2-((pyridin-2-ylmethyl)amino) phenyl)carbamate (0.1 g. 0.23 mmol) in DCM (10 mL) were add NaHCO$_3$ (0.197 g, 2.35 mmol) followed by 2-chloroacetyl chloride (0.022 g, 0.28 mmol) and stirred at 0° C. for 10 min. Reaction mixture was diluted with DCM (100 mL), washed with water (50 mL), brine (20 mL), dried over sodium sulphate and concentrated. The residue was as such used for next step without further purification (0.1 g, 85%). $^1$H NMR (400 MHz, DMSO-d$_6$): δ 11.05-10.80 (bs, 1H), 8.54 (d, J=4.4 Hz, 1H), 7.89-7.85 (m, 1H), 7.70 (s, 1H), 7.49-7.41 (m, 1H), 7.39-7.37 (m, 1H), 7.22 (s, 1H), 4.35-4.20 (m, 4H), 3.75 (s, 3H), 2.30 (s, 3H), 2.07 (s, 3H), 1.23 (s, 9H); LC-MS: m/z 502.2 (M+1)$^+$.

Step-(vi): Synthesis of tert-butyl 7-(3,5-dimethyl-isoxazol-4-yl)-6-methoxy-3-oxo-4-(pyridin-2-ylmethyl)-3,4-dihydroquinoxaline-1 (2H)-carboxylate To an ice-cooled solution of tert-butyl (5-(3,5-dimethyl-isoxazol-4-yl)-4-methoxy-2-((pyridin-2-ylmethyl)amino) phenyl)carbamate (0.1 g, 0.20 mmol) in DMF (5 mL) was add NaH (0.0.12 g, 0.29 mmol) and stirred at (0° C. for 15 min. After completion of reaction, the reaction mixture was quenched with MeOH, diluted with H$_2$O (10 mL) and extracted with EtOAc (50 mL×2). The organic layer was washed with water (50 mL), brine (20 mL), dried over sodium sulphate and concentrated. The residue was as such used for next step without further purification (0.093 g, 100%); LC-MS: m/z 465.3 (M+1)$^+$.

Step-(vii): Synthesis of 6-(3,5-dimethylisoxazol-4-yl)-7-methoxy-1-(pyridin-2-ylmethyl) quinoxalin-2 (1H)-one To an ice-cooled solution of tert-butyl 7-(3,5-dimethyl-isoxazol-4-yl)-6-methoxy-3-oxo-4-(pyridin-2-ylmethyl)-3,4-dihydroquinoxaline-1(2H)-carboxylate (0.1 g, 0.21 mmol) in DCM (5 mL) was add TFA (0.016 mL, 2.15 mmol) and stirred at RT for 3 h. After completion of reaction, the reaction mixture was diluted with DCM (100 mL), washed with aq. sodium bicarbonate solution (20 mL), water (50 mL), brine (20 mL), dried over sodium sulphate and concentrated. The residue was purified by preparative TLC to afford the title compound as pale brown solid (0.015 g, 19%). $^1$H NMR (400 MHz, DMSO-d$_6$): δ 8.50 (d, J=4.0 Hz, 1H), 8.20 (s, 1H), 7.80 (t, J=7.1 Hz, 1H), 7.12 (s, 1H), 7.45 (d, J=7.9 Hz, 1H), 7.33-7.29 (m, 1H), 7.13 (s. 1H), 5.64 (s, 2H), 3.77 (s, 3H), 2.26 (s, 3H), 2.06 (s, 3H); LC-MS: m/z 363.2 (M+1)$^+$.

Example-XVI: Synthesis of N-(4-(4-chlorobenzyl)-6-methoxy-3-oxo-3,4-dihydro-2H-benzo[b][1,4] oxazin-7-yl)-3,5-dimethylisoxazole-4-carboxamide (Compound-94)

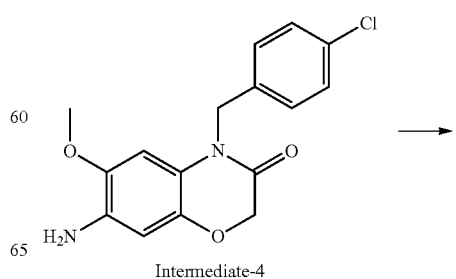

Intermediate-4

125

-continued

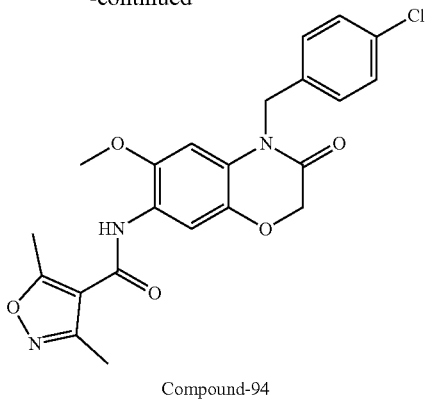

Compound-94

Step-(i): Synthesis of N-(4-(4-chlorobenzyl)-6-methoxy-3-oxo-3,4-dihydro-2H-benzo[b][1,4]oxazin-7-yl)-3,5-dimethylisoxazole-4-carboxamide To a solution of 7-amino-4-(4-chlorobenzyl)-6-methoxy-2H-benzo[b][1,4]oxazin-3(4H)-one (0.10 g, 0.31 mmol) in DCM (5 mL) were added 3,5-dimethylisoxazole-4-carboxylic acid (0.05 g, 0.33 mmol), HOBt (0.02, 0.15 mmol), EDC.HCl (0.12 g, 0.63 mmol), Triethylamine (0.11 ml, 0.77 mmol) and stirred at RT for 16 h. After completion of reaction, the reaction mixture was diluted with DCM (100 mL), washed with water (50 mL), brine (50 mL), dried over sodium sulphate and concentrated. The residue was purified by preparative TLC to afford title product as a yellow solid (0.03 g 22%). $^1$H NMR (400 MHz, DMSO-d$_6$): δ 9.08 (bs, 1H), 7.63 (s, 1H), 7.40 (d, J=8.3 Hz, 2H), 7.35 (d, J=8.3 Hz, 2H), 6.80 (s, 1H), 5.22 (s, 2H), 4.73 (s, 2H), 3.70 (s, 3H), 3.56 (s, 3H), 2.34 (s, 3H); LC-MS: m/z 442.1 (M+1)$^+$.

Example-XVII: Synthesis of 4-(4-chlorobenzyl)-7-((3,5-dimethylisoxazol-4-yl)amino)-6-methoxy-2H-benzo[b][1,4]oxazin-3(4H)-one (Compound-95)

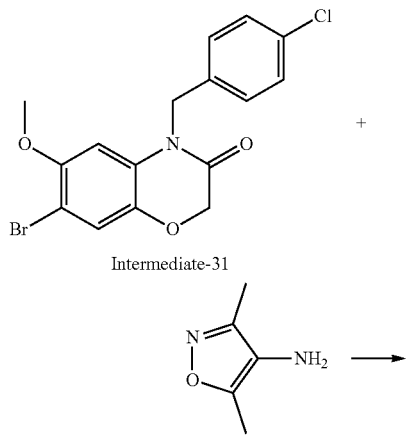

Intermediate-31

126

-continued

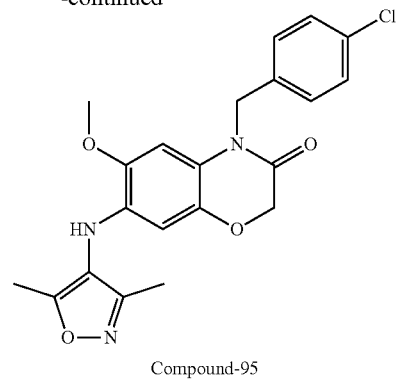

Compound-95

To a solution of 7-bromo-4-(4-chlorobenzyl)-6-methoxy-2H-benzo[b][1,4]oxazin-3(4H)-one (0.10 g, 0.26 mmol) in toluene (5.0 mL) in a sealed tube were added 3,5-dimethylisoxazol-4-amine (0.03 g, 0.26 mmol), cesium carbonate (0.20 g, 0.65 mmol), xantphos (0.02 g, 0.025 mmol) and degassed with nitrogen purging for 20 min. Then palladium (II)acetate (0.015 g, 0.065 mmol) was added and heated at 100° C. for 16 h. After completion of reaction, the reaction mixture was allowed RT, diluted with EtOAc (50 mL), washed with water (50 mL), brine (50 mL), dried over sodium sulphate and concentrated. The residue was purified by preparative TLC to afford the title product as pale brown solid (6 mg, 0.5%). $^1$H NMR (400 MHz, DMSO-d$_6$) δ 7.41 (d, J=8.3 Hz, 2H), 7.35 (d, J=8.3 Hz, 2H), 6.66 (s, 1H), 6.57 (s, 1H), 5.14 (bs, 2H), 4.59 (s, 2H), 3.70 (s, 3H), 2.18 (s, 3H), 1.98 (s, 3H); LC-MS: m/z 414.1 (M+1)$^+$.

Example-XVIII: Synthesis of 6-(3,5-dimethylisoxazol-4-yl)-3-(hydroxymethyl)-7-methoxy-1-(pyridin-2-ylmethyl)quinolin-2(1H)-one (Compound-96) & 6-(3,5-dimethylisoxazol-4-yl)-3-(fluoromethyl)-7-methoxy-1-(pyridin-2-ylmethyl)quinolin-2(1H)-one (Compound-97)

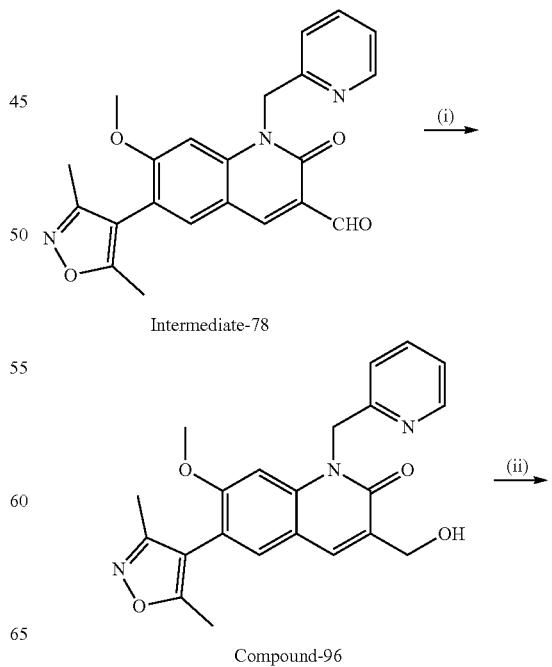

Compound-96

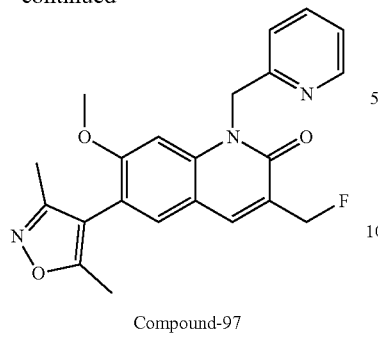

Compound-97

Step-(i): Synthesis of 6-(3,5-dimethylisoxazol-4-yl)-3-(hydroxymethyl)-7-methoxy-1-(pyridin-2-ylmethyl) quinolin-2(1H)-one To an ice cooled solution of 6-(3,5-dimethylisoxazol-4-yl)-7-methoxy-2-oxo-1-(pyridin-2-ylmethyl)-1,2-dihydroquinoline-3-carbaldehyde (0.07 g, 0.18 mmol) in MeOH (3 mL) was added NaBH$_4$ (0.007 g, 0.18 mmol) pinch wise and stirred at 0° C. for 1 h. After completion of reaction, the reaction mixture concentrated, the residue was diluted with water and extracted with EtOAc (50 mL×2). The organic layer was washed brine (100 mL), dried over sodium sulphate and concentrated under reduced pressure and column purified to afford the title product as white solid (0.02 g, 28%). $^1$H NMR (400 MHz, DMSO-d$_6$): δ 8.52 (d, J=8.4 Hz, 1H), 7.91 (s, 1H), 7.77 (t. J=7.8 Hz, 1H), 7.62 (s, 1H), 7.32-7.28 (m, 2H), 7.11 (s, 1H), 5.75 (s, 2H), 5.27 (t, J=5.4 Hz, 1H), 4.46 (d, J=5.4 Hz, 2H), 3.73 (s, 3H), 2.25 (s, 3H), 2.06 (s, 3H); LC-MS: m/z 392.1 (M+1)$^+$.

Step-(ii): Synthesis of 6-(3,5-dimethylisoxazol-4-yl)-3-(fluoromethyl)-7-methoxy-1-(pyridin-2-ylmethyl)quinolin-2(1H)-one To a cooled solution of 6-(3,5-dimethylisoxazol-4-yl)-3-(hydroxymethyl)-7-methoxy-1-(pyridin-2-ylmethyl)quinolin-2(1H)-one (0.04 g, 0.102 mmol) in DCM (2 mL) was added DAST (0.04 mL, 0.3 mmol) and stirred at room temperature for 2 h. The reaction mixture diluted with DCM (50 mL) and washed with water (50 mL), dried over sodium sulphate and concentrated under reduced pressure and purified by preparative TLC to afford the title compound as an off white solid (0.01 g, 25%). $^1$H NMR (300 MHz, CDCl$_3$): δ 8.53-8.51 (m, 1H), 7.72 (s, 1H), 7.58 (t, J=7.4 Hz, 1H), 7.29 (d, J=7.8 Hz, 1H), 7.24 (s, 1H), 7.16-7.14 (m, 2H), 5.64 (bs, 2H), 5.51 (s, 1H), 5.40 (s, 1H), 3.74 (s, 3H), 2.20 (s, 3H), 2.06 (s, 3H); LC-MS: m/z 394.2 (M+1)$^{30}$.

Example-XIX: Synthesis of 6-(3,5-dimethylisoxazol-4-yl)-7-methoxy-1-((5-(1-methyl-1H-pyrazol-4-yl) pyridin-2-yl) methyl) quinolin-2(1H)-one (Compound-98)

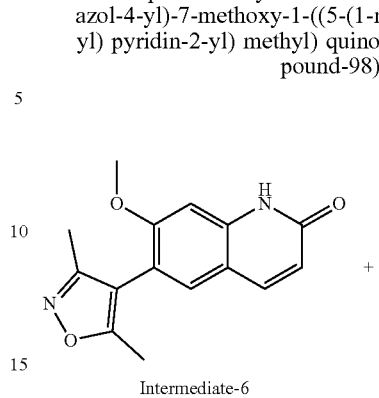

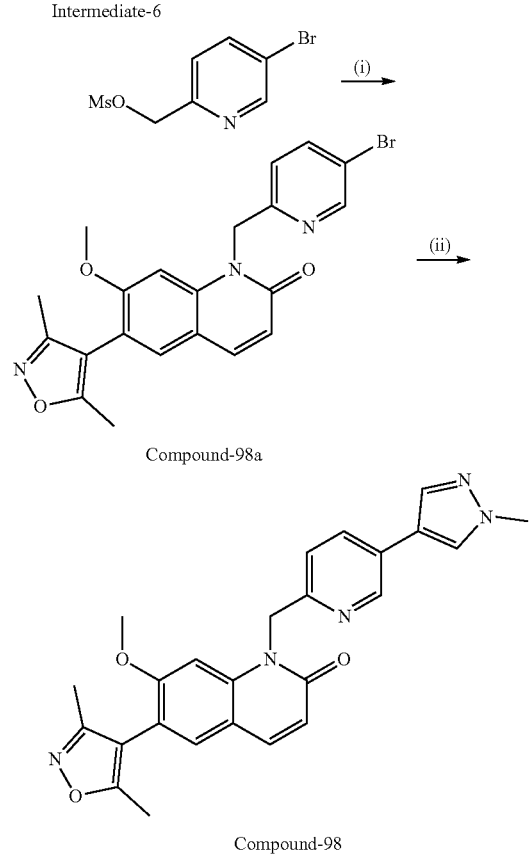

Step-(i): 1-((5-bromopyridin-2-yl) methyl)-6-(3,5-dimethylisoxazol-4-yl)-7-methoxy quinolin-2(1H)-one The process of this adopted from step-d of Intermediate-78.

$^1$H NMR (400 MHz, DMSO-d$_6$): δ 8.65 (d, J=2.0 Hz, 1H), 8.03 (dd, J$_1$=2.4 Hz, J$_2$=8.8 Hz, 1H), 7.91 (d, J=9.3 Hz, 1H), 7.63 (s, 1H), 7.34 (d, J=8.3 Hz, 1H), 7.07 (s, 1H), 6.57 (d, J=9.3 Hz, 1H), 5.63 (s, 2H), 3.76 (s, 3H), 2.25 (s, 3H), 2.06 (s, 3H); LC-MS: m/z 442 (M+2)$^{2+}$.

Step-(ii): 6-(3,5-dimethylisoxazol-4-yl)-7-methoxy-1-((5-(1-methyl-1H-pyrazol-4-yl) pyridin-2-yl) methyl) quinolin-2(1H)-one The process of this was adopted from compound-17 (Example-VII). $^1$H NMR (400 MHz, DMSO-d$_6$): δ 8.77 (d, J=2.0 Hz, 1H), 8.21 (s, 1H), 7.94-7.89 (m, 3H), 7.62 (s, 1H), 7.32 (d, J=8.3 Hz, 1H), 7.19 (s, 1H), 6.58 (d, J=9.3 Hz, 1H), 5.63 (s, 2H), 3.86 (s, 3H), 3.77 (s, 3H), 2.24 (s, 3H), 2.05 (s, 3H); LC-MS: m/z 442.7 (M+1)+.

Example-XX: Synthesis of 1-((5-(3,5-dimethyl-1H-pyrazol-4-yl)pyridin-2-yl)methyl)-6-(3,5-dimethyl-isoxazol-4-yl)-7-methoxyquinolin-2(1H)-one (Compound-99)

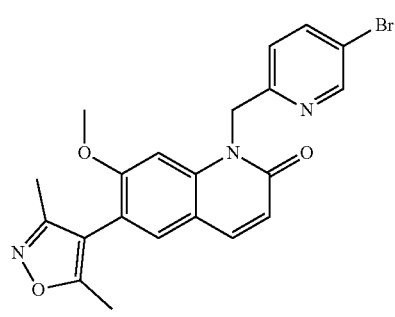

Compound-98a

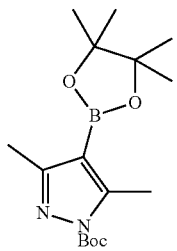

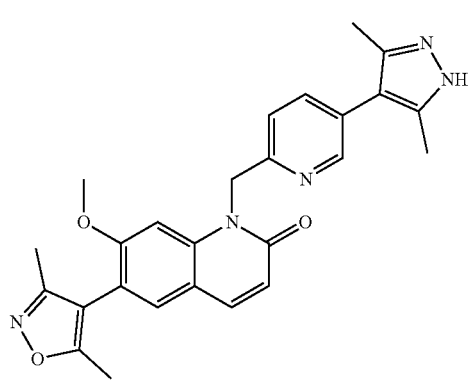

Compound-99

The process of this was adopted from compound-17 (Example-VII). $^1$H NMR (400 MHz, DMSO-$d_6$): δ 12.39 (bs, 1H), 8.47 (d, J=1.4 Hz, 1H), 7.91 (d, J=9.3 Hz, 1H), 7.14 (dd, $J_1$=2.4 Hz, $J_2$=8.3 Hz, 1H), 7.63 (s, 1H), 7.37 (d, J=8.3 Hz, 1H), 7.23 (s, 1H), 6.59 (d, J=9.3 Hz, 1H), 5.66 (s, 2H), 3.78 (s, 3H), 2.25 (s, 9H), 2.06 (s, 3H); LC-MS: m/z 456.2 (M+1)+.

Example-XXI: Synthesis of 6-(3,5-dimethylisoxazol-4-yl)-1-((5-(3-hydroxypyrrolidin-1-yl)pyridin-2-yl)methyl)-7-methoxyquinolin-2(1H)-one (Compound-100)

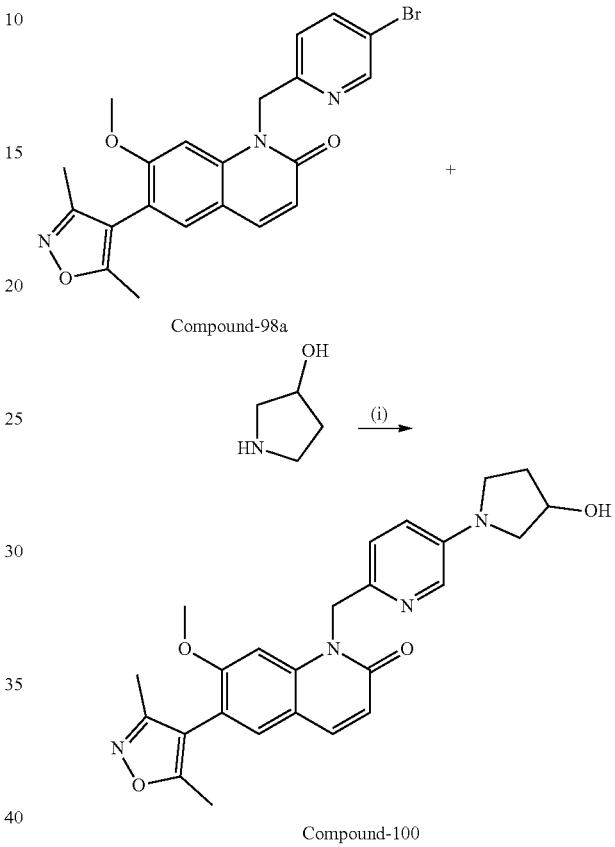

To a solution of 1-((5-bromopyridin-2-yl)methyl)-6-(3,5-dimethylisoxazol-4-yl)-7-methoxyquinolin-2(1H)-one (0.05 g, 0.11 mmol) in 1,4-dioxane (4 mL) in a sealed tube were added pyrrolidin-3-ol (0.01 g, 0.13 mmol), cesium carbonate (0.11 g, 0.34 mmol) and BINAP (0.004 g, 0.006 mmol) and degassed with nitrogen purging for 15 min then added palladium acetate (0.003 g, 0.011 mmol), then heated at 100° C. for 16 h. After completion of the reaction, the reaction mixture was diluted with EtOAc (50 mL), washed with water (50 mL), brine (50 mL), dried over sodium sulphate and concentrated. The residue was purified by preparative TLC to afford the title compound as brown solid (0.02 g, 43%). $^1$H NMR (400 MHz, DMSO-$d_6$): δ 7.91 (d, J=9.8 Hz, 1H), 7.85 (s, 1H), 7.60 (s, 1H), 7.30 (s, 1H), 7.20 (d, J=8.8 Hz, 1H), 6.99-6.97 (m, 1H), 6.59 (d, J=9.3 Hz, 1H), 5.53 (bs, 2H), 4.41-4.39 (m, 1H), 3.82 (s, 3H), 3.60-3.30 (m, 4H), 3.10 (d, J=10.3 Hz, 1H), 2.24 (s, 3H), 2.06 (s, 3H), 2.03-1.91 (m, 2H); LC-MS: m/z 447.1 (M+1)+.

Example-XX: Synthesis of 6-(3,5-dimethylisoxazol-4-yl)-7-methoxy-1-(pyridin-2-ylmethyl)-3-(2,2,2-trifluoro-1-hydroxyethyl)quinolin-2(1H)-one (Compound-101)

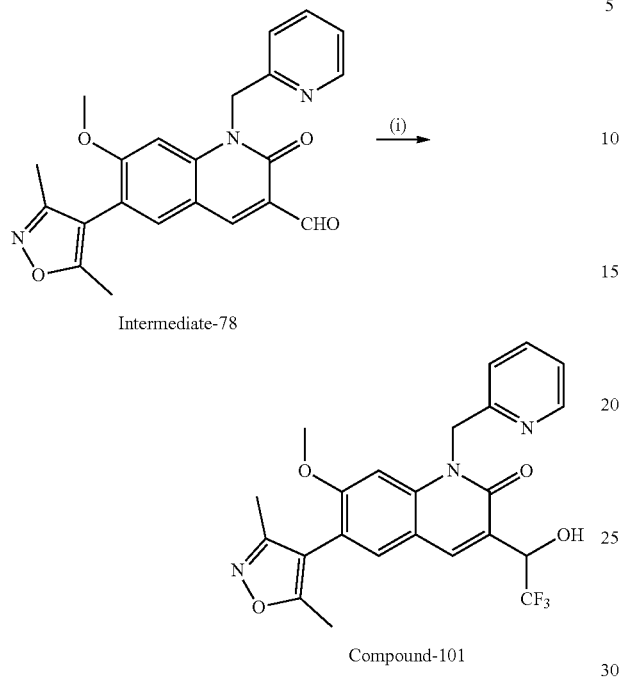

Intermediate-78

Compound-101

To a cooled solution of 6-(3,5-dimethylisoxazol-4-yl)-7-methoxy-2-oxo-1-(pyridin-2-ylmethyl)-1,2-dihydroquinoline-3-carbaldehyde (0.02 g, 0.051 mmol) in THF (1 mL) were added tetra butyl ammonium fluoride 1.0 M in THF (0.015 mL, 0.015 mmol) and TMS-CF₃ (0.01 mL, 0.061 mmol), stirred at 0° C. for 1 h. The reaction mixture quenched with sat. NH₄Cl, extracted with EtOAc (50 mL), washed with water (50 mL), dried over sodium sulphate and concentrated. The residue was purified on preparative TLC to afford the title compound as an off white solid (0.01 g, 43%). ¹H NMR (400 MHz, DMSO-d₆): δ 8.52 (d, J=3.9 Hz, 1H), 8.19 (s, 1H), 7.80-7.77 (m, 2H), 7.33-7.28 (m, 2H), 7.15 (s, 1H), 6.90 (d, J=7.4 Hz, 1H), 5.77-5.64 (m, 2H), 5.49-5.43 (m, 1H), 3.76 (s, 3H), 2.25 (s, 3H), 2.07 (s, 3H); LC-MS: m/z 460.2 (M+1)⁺.

The above compound-101 (racemate) was purified by chiral HPLC. The characterization data of desired isomers was given below.

Example-XXIII: Synthesis of 6-(3,5-dimethylisoxazol-4-yl)-7-methoxy-1-(pyridin-2-ylmethyl)-3-(2,2,2-trifluoro-1,1-dihydroxyethyl)quinolin-2(1H)-one (Compound-104)

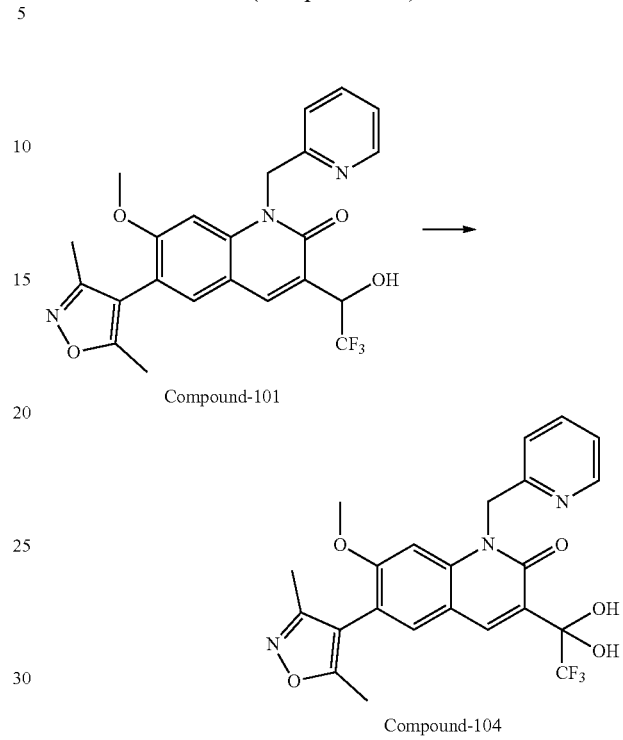

Compound-101

Compound-104

To cooled solution of 6-(3,5-dimethylisoxazol-4-yl)-7-methoxy-1-(pyridin-2-ylmethyl)-3-(2,2,2-trifluoro-1-hydroxyethyl)quinolin-2(1H)-one (0.2 g, 0.43 mmol) in DCM (5 mL) was added dess-martin per iodinane (0.28 g, 0.65 mmol) and stirred at room temperature for 16 h. After completion of the reaction, the reaction mixture was diluted with DCM (100 mL) and washed with mixture of aqueous NaHCO₃ and Na₂S₂O₅ in 5:1 ratio dried over sodium sulphate and concentrated. The residue was purified by preparative HPLC to afford title compound as white solid (0.015 g, 8%). ¹H NMR (400 MHz, DMSO-d₆): δ 8.55 (s, 2H), 8.50 (d, J=4.9 Hz, 1H), 8.40 (s, 1H), 7.94 (s, 1H), 7.82 (t, J=6.9 Hz, 1H), 7.39 (d, J=7.8 Hz, 1H), 7.32-7.29 (m, 1H), 7.23 (s, 1H), 5.77 (s, 2H), 3.79 (s, 3H), 2.26 (s, 3H), 2.07 (s, 3H); ES-MS: m/z 476.1 (M+1)⁺.

| Compound No. | Structure | Characterization Data |
|---|---|---|
| 102 & 103 | 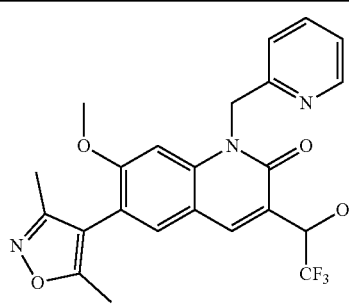 | Compound 102 (Isomer-1): ¹H NMR (400 MHz, DMSO-d₆): δ 8.52 (d, J = 4.4 Hz, 1H), 8.18 (s, 1H), 7.80 (s, 1H), 7.79-7.77 (m, 1H), 7.33-7.29 (m, 2H), 7.15 (s, 1H), 6.90 (d, J = 6.0 Hz, 1H), 5.77-5.64 (m, 2H), 5.49-5.44 (m, 1H), 3.76 (s, 3H), 2.25 (s, 3H), 2.06 (s, 3H); LC-MS: m/z 460.1 (M + 1)⁺. Compound 103 (Isomer-2): ¹H NMR (400 MHz, DMSO-d₆): δ 8.52 (d, J = 4.4 Hz, 1H), 8.19 (s, 1H), 7.80 (s, 1H), 7.79-7.77 (m, 1H), 7.33-7.29 (m, 2H), 7.15 (s, 1H), 6.90 (d, J = 5.6 Hz, 1H), 5.77-5.64 (m, 2H), 5.48-5.45 (m, 1H), 3.76 (s, 3H), 2.25 (s, 3H), 2.06 (s, 3H); LC-MS: m/z 460.1 (M + 1)⁺. |

Example-XXIV: Synthesis of 1-(4-chlorophen-ethyl)-6-(3,5-dimethylisoxazol-4-yl)-7-methoxy-3-methyl-2-oxo-1,2-dihydroquinoline-4-carbonitrile (Compound-105) & 2-(1-(4-chlorophenethyl)-6-(3,5-dimethylisoxazol-4-yl)-7-methoxy-2-oxo-1,2-dihydroquinolin-3-yl)acetonitrile: (Compound-106)

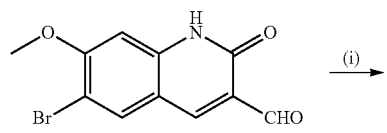

(i)

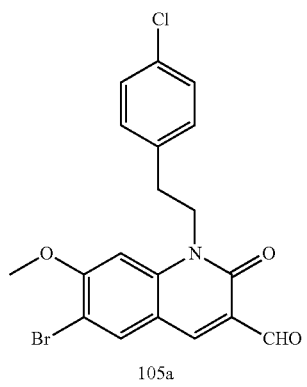
105a (ii)

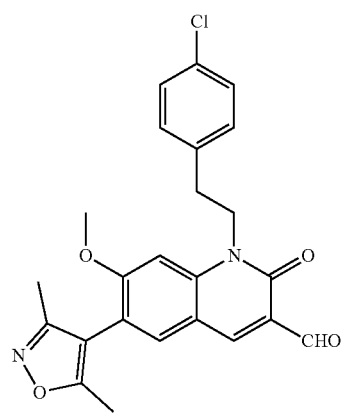
105b (iii)

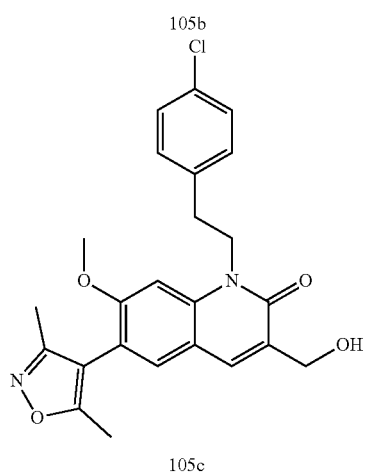
105c (iv)

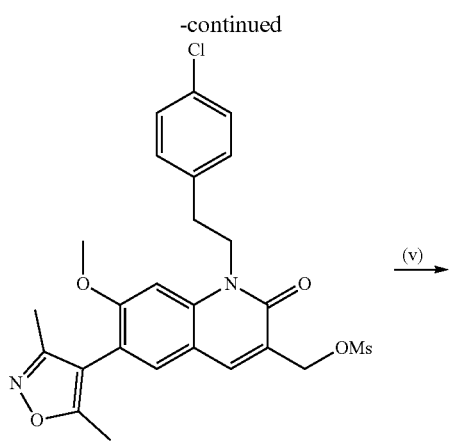
105d (v)

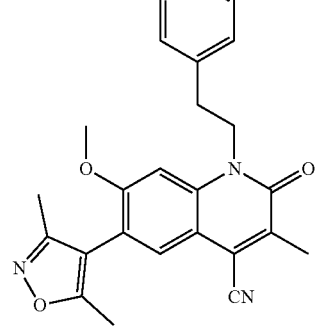
A
Compound-105

+

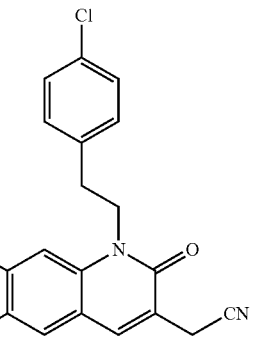
B
Compound-106

Step-(i): Synthesis of 6-bromo-1-(4-chlorophen-ethyl)-7-methoxy-2-oxo-1,2-dihydroquinoline-3-carbaldehyde The process of this was adopted from step-(i) of compound-1 (Example-I). $^1$H NMR (400 MHz, CDCl$_3$): δ 10.42 (s, 1H), 8.24 (s, 1H), 7.89 (s, 1H), 7.30 (d, J=8.3 Hz, 2H), 7.20 (d, J=8.3 Hz, 2H), 6.63 (s, 1H), 4.48 (t, J=7.8 Hz, 2H), 3.96 (s, 3H), 3.06 (t, J=7.8 Hz, 2H); LC-MS: m/z 421.0 (M+1)$^+$.

Step-(ii): Synthesis of 1-(4-chlorophenethyl)-6-(3,5-dimethylisoxazol-4-yl)-7-methoxy-2-oxo-1,2-dihydroquinoline-3-carbaldehyde The process of this was adopted from compound-17 (Example-VII). $^1$H NMR (400 MHz, CDCl$_3$): δ 10.45 (s, 1H), 8.33 (s, 1H), 7.46 (s, 1H), 7.30 (d, J=8.3 Hz, 2H), 7.22 (d, J=8.3 Hz, 2H), 6.67 (s, 1H), 4.53 (t, J=7.9 Hz, 2H), 3.89 (s, 3H), 3.10 (t, J=7.8 Hz, 2H), 2.31 (s, 3H), 2.15 (s, 3H); LC-MS: m/z 437.1 (M+1)$^+$.

Step-(iii): Synthesis of 1-(4-chlorophenethyl)-6-(3, 5-dimethylisoxazol-4-yl)-3-(hydroxymethyl)-7-methoxyquinolin-2(1H)-one The process of this was adopted from compound-97 (Example-XVIII-). The desired compound obtained as a white solid (0.2 g, 67%). $^1$H NMR (400 MHz, CDCl$_3$): δ 7.64 (s, 1H), 7.32-7.21 (m, 5H), 6.67 (s, 1H), 4.66-4.64 (m, 2H), 4.52 (t, J=7.8 Hz, 2H), 3.86 (s, 3H), 3.35-3.30 (m, 1H), 3.08 (t, J=7.8 Hz, 2H), 2.31 (s, 3H), 2.16 (s, 3H); LC-MS: m/z 439.1 (M+1)$^+$.

Step-(iv): Synthesis of 1-(4-chlorophenethyl)-6-(3, 5-dimethylisoxazol-4-yl)-7-methoxy-2-oxo-1,2-dihydroquinolin-3-yl)methylmethanesulfonate The process of this step was adopted from intermediate-15. The obtained crude was used in the next step without any purification.

Step-(v): Synthesis of 1-(4-chlorophenethyl)-6-(3,5-dimethylisoxazol-4-yl)-7-methoxy-3-methyl-2-oxo-1,2-dihydroquinoline-4-carbonitrile & 2-(1-(4-chlorophenethyl)-6-(3,5-dimethylisoxazol-4-yl)-7-methoxy-2-oxo-1,2-dihydroquinolin-3-yl)acetonitrile To a cooled solution of (1-(4-chlorophenethyl)-6-(3,5-dimethylisoxazol-4-yl)-7-methoxy-2-oxo-1,2-dihydroquinolin-3-yl)methyl methanesulfonate (0.22 g, 0.43 mmol) in DMF (5 mL) was added potassium cyanide (0.042 g, 0.64 mmol) and stirred at room temperature for 16 h. After completion of the reaction, the reaction mixture poured into ice water and extracted with EtOAc (100×2), dried over sodium sulphate, concentrated under reduced pressure and column purified to afford title compound as pale yellow solid (A) (0.02 g, 10%). $^1$H NMR (400 MHz, CDCl$_3$): δ 7.64 (s, 1H), 7.30 (d, J=8.3 Hz, 2H), 7.21 (d, J=8.3 Hz, 2H), 6.73 (s, 1H), 4.51 (t, J=7.4 Hz, 2H), 3.86 (s, 3H), 3.07 (t, J=7.8 Hz, 2H), 2.53 (s, 3H), 2.33 (s, 3H), 2.17 (s, 3H); LC-MS: m/z 448.1 (M+1)$^+$. & (B) (0.065 g, 34%). $^1$H NMR (400 MHz, CDCl$_3$): δ 7.89 (s, 1H), 7.37 (s, 1H), 7.30-7.28 (m, 2H), 7.21 (d, J=8.8 Hz, 2H), 6.72 (s, 1H), 4.52 (t, J=7.3 Hz, 2H), 3.87 (s, 3H), 3.75 (d, J=1.5 Hz, 2H), 3.07 (t, J=7.9 Hz, 2H), 2.32 (s, 3H), 2.17 (s, 3H); LC-MS: m/z 448.1 (M+1)$^+$.

Biological Data:

In-Vitro Biochemical Data of bicyclic heterocyclic derivatives in time-resolved fluorescence resonance energy transfer (TR-FRET) assay.

The Bet brommodomain TR-FRET assay has been used to identify compounds that bind to bet bromodomain and prevent its interaction with acetylated histone peptides.

In the assay, optimized concentration of in-house Bet bromodomain protein (BRD4) and 300 nM of acetyl histone peptide substrate were diluted in assay buffer (50 mM HEPES, pH: 7.5, 50 mM NaCl, 500 μM CHAPS) and were added to the positive control and test control wells in a 384 well plate. Substrate control wells have 300 nM of acetyl histone peptide substrate diluted in assay buffer. Buffer blank wells were added with assay buffer. The reaction mixture was allowed for incubation at room temperature for 30 mins. Stock solutions of test compounds at 20 mM DMSO are prepared. Compounds are serially diluted and added to the test wells in 384-well polypropylene plates. The reaction mixture was further incubated for 30 mins at room temperature on a plate shaker. 2 nM of Europium labeled streptavidn and 10 nM of XL-665 labeled antibody diluted in detection buffer (50 mM HEPES, pH: 7.5, 50 mM NaCl, 500 μM CHAPS and 800 mM KF) were added to all the wells excluding the buffer blank wells. The reaction plate was incubated for additional 30 mins at room temperature on plate shaker. The plate was read in Perkin Elmer WALLAC 1420 Multilabel Counter Victor 3 (Ex: 340 nm Em: 615 and 665 nm). The amount of displacement of the peptide was measured as ratio of specific 665 nm energy transfer signal to 615 nm signals. The compounds IC$_{50}$ was determined by fitting the dose response data to sigmoid curve fitting equation using Graph Pad Prism software V5.

The compounds were screened in the above mentioned assay and the results (IC$_{50}$) are summarized in the table below; wherein "A" refers to an IC$_{50}$ value of less than or equal to 1000 nM, "B" refers to IC$_{50}$ value in range of 1000.01 to 3000 nM and "C" refers to IC$_{50}$ value of greater than 3000 nM.

| Group | Compound No |
|---|---|
| A | 1, 2, 4, 5, 7, 8, 9, 10, 16, 17, 18, 20, 21, 22, 23, 24, 26, 28, 29, 32, 34, 36, 37, 38, 39, 40, 41, 43, 44, 45, 46, 47, 49, 50, 55, 56, 58, 59, 62, 64, 65, 66, 67, 68, 69, 72, 73, 74, 77, 78, 79, 80, 83, 84, 89, 90, 93, 96, 97, 98, 101, 102, 103, 104, 106. |
| B | 11, 12, 25, 27, 30, 31, 33, 35, 42, 51, 53, 57, 75, 81, 82, 85, 87, 88. |
| C | 3, 6, 13, 14, 15, 19, 48, 52, 54, 60, 61, 63, 70, 71, 76, 86, 91, 92, 94, 95, 105. |

We claim:
1. A compound of formula (I):

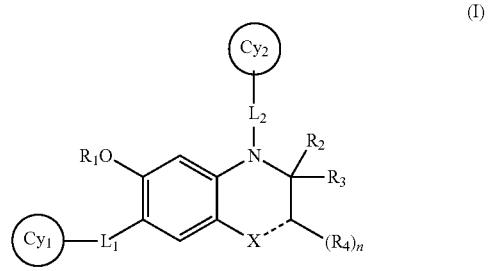

or a pharmaceutically acceptable salt or a pharmaceutically acceptable stereoisomer thereof;
wherein,
   dotted line [- - -] represents a single bond;
   X is O;
   L$_1$ is a direct bond or a linker selected from —NH—, —NHC(O)—, or —NHS(O)$_2$—;
   L$_2$ is a linker selected from —(CHR$_6$)$_n$—, —C(O)—, or —S(O)$_2$—;
   Cy$_1$ is an optionally substituted 5-6 membered monocyclic ring containing 1-4 hetero atoms/-hetero groups independently selected from N, NH, O, or —C(O)—;

wherein the optional substituent at each occurrence is independently selected from one or more $R_7$;

$Cy_2$ is an optionally substituted 4-12 membered monocyclic or bicyclic ring containing 0-3 hetero atoms/hetero groups independently selected from N, NH, O, or S; wherein the optional substituent at each occurrence is independently selected from one or more $R_8$;

$R_1$ is selected from hydrogen, alkyl, alkenyl, haloalkyl, hydroxyalkyl, alkoxyalkyl, aminoalkyl, heterocyclyl, or heterocyclylalkyl;

$R_2$ and $R_3$ independently are hydrogen, alkyl, or together form an oxo group;

$R_4$ at each occurrence is independently selected from hydrogen, alkyl, cycloalkyl, cyanoalkyl, hydroxyalkyl, or optionally substituted haloalkyl; wherein the optional substituent is one or more hydroxyl;

$R_6$ is hydrogen or alkyl;

$R_7$ is selected from alkyl, hydroxyl, or cycloalkyl;

$R_8$ is selected from alkyl, alkoxy, amino, cyano, halogen, haloalkyl, hydroxy, —C(O)alkyl, or optionally substituted heterocyclyl; wherein the optional substituent is selected from one or more alkyl or hydroxy; and n is an integer selected from 1 or 2.

2. The compound according to claim 1, wherein $Cy_1$ is 3,5-dimethylisoxazole.

3. The compound according to claim 1, wherein $L_1$ is a direct bond.

4. The compound according to claim 1, wherein $L_2$ is —$CH_2$—.

5. The compound according to claim 1, wherein $Cy_2$ is optionally substituted pyridyl or optionally substituted phenyl.

6. The compound according to claim 5, wherein the optional substituent is halogen, haloalkyl, alkoxy, amino, or cyano.

7. The compound according to claim 1, wherein $R_4$ is alkyl, cyanoalkyl, hydroxyalkyl, or optionally substituted haloalkyl; wherein the optional substituent is hydroxy.

8. A compound selected from the group consisting of:
4-(4-chlorobenzyl)-7-(3,5-dimethylisoxazol-4-yl)-6-methoxy-3,4-dihydro-2H-benzo[b][1,4]oxazine;
4-(1-(4-chlorophenyl)ethyl)-7-(3,5-dimethylisoxazol-4-yl)-6-methoxy-3,4-dihydro-2H-benzo[b][1,4]oxazine;
7-(3,5-dimethylisoxazol-4-yl)-6-methoxy-4-(1-(pyridin-3-yl)ethyl)-3,4-dihydro-2H-benzo[b][1,4]oxazine;
4-((3-chlorophenyl)sulfonyl)-7-(3,5-dimethylisoxazol-4-yl)-6-methoxy-3,4-dihydro-2H-benzo[b][1,4]oxazine;
7-(3,5-dimethylisoxazol-4-yl)-6-methoxy-4-(pyridin-3-ylsulfonyl)-3,4-dihydro-2H-benzo[b][1,4]oxazine;
N-(4-(4-chlorobenzyl)-6-methoxy-3-oxo-3,4-dihydro-2H-benzo[b][1,4]oxazin-7-yl)-3,5-dimethylisoxazole-4-sulfonamide;
2-((7-(3,5-dimethylisoxazol-4-yl)-6-methoxy-2H-benzo[b][1,4]oxazin-4(3H)-yl)methyl)aniline;
7-(3,5-dimethylisoxazol-4-yl)-6-methoxy-4-(pyridin-4-ylmethyl)-2H-benzo[b][1,4]oxazin-3(4H)-one;
4-(4-chlorobenzyl)-7-(3,5-dimethylisoxazol-4-yl)-6-methoxy-2H-benzo[b][1,4]oxazin-3(4H)-one;
7-(3,5-dimethylisoxazol-4-yl)-6-methoxy-4-(1-(pyridin-4-yl)ethyl)-2H-benzo[b][1,4]oxazin-3(4H)-one (Isomer-1);
7-(3,5-dimethylisoxazol-4-yl)-6-methoxy-4-(1-(pyridin-4-yl)ethyl)-2H-benzo[b][1,4]oxazin-3(4H)-one (Isomer-2);
7-(3,5-dimethylisoxazol-4-yl)-6-methoxy-4-(pyridin-3-ylmethyl)-2H-benzo[b][1,4]oxazin-3(4H)-one;
7-(3,5-dimethylisoxazol-4-yl)-6-methoxy-4-(pyridin-2-ylmethyl)-2H-benzo[b][1,4]oxazin-3(4H)-one;
7-(3,5-dimethylisoxazol-4-yl)-6-methoxy-4-((tetrahydro-2H-pyran-4-yl)methyl)-2H-benzo[b][1,4]oxazin-3(4H)-one;
7-(3,5-dimethylisoxazol-4-yl)-6-methoxy-4-(1-(pyridin-3-yl)ethyl)-2H-benzo[b][1,4]oxazin-3(4H)-one (Isomer-1);
7-(3,5-dimethylisoxazol-4-yl)-6-methoxy-4-(1-(pyridin-3-yl)ethyl)-2H-benzo[b][1,4]oxazin-3(4H)-one (Isomer-2);
7-(3,5-dimethylisoxazol-4-yl)-6-methoxy-4-((6-methoxypyridin-3-yl)methyl)-2H-benzo[b][1,4]oxazin-3(4H)-one;
6-((7-(3,5-dimethylisoxazol-4-yl)-6-methoxy-3-oxo-2H-benzo[b][1,4]oxazin-4(3H)-yl)methyl)nicotinonitrile;
4-((5-chloropyridin-2-yl)methyl)-7-(3,5-dimethylisoxazol-4-yl)-6-methoxy-2H-benzo[b][1,4]oxazin-3(4H)-one;
7-(3,5-dimethylisoxazol-4-yl)-4-((5-fluoropyridin-2-yl)methyl)-6-methoxy-2H-benzo[b][1,4]oxazin-3(4H)-one;
7-(3,5-dimethylisoxazol-4-yl)-6-methoxy-4-((5-methoxypyridin-2-yl)methyl)-2H-benzo[b][1,4]oxazin-3(4H)-one;
7-(3,5-dimethylisoxazol-4-yl)-6-methoxy-4-(1-(pyridin-2-yl)ethyl)-2H-benzo[b][1,4]oxazin-3(4H)-one;
7-(3,5-dimethylisoxazol-4-yl)-6-methoxy-4-((6-methylpyridin-3-yl)methyl)-2H-benzo[b][1,4]oxazin-3(4H)-one;
4-(1-(4-chlorophenyl)ethyl)-7-(3,5-dimethylisoxazol-4-yl)-6-methoxy-2H-benzo[b][1,4]oxazin-3(4H)-one (Isomer-1);
4-(1-(4-chlorophenyl)ethyl)-7-(3,5-dimethylisoxazol-4-yl)-6-methoxy-2H-benzo[b][1,4]oxazin-3(4H)-one (Isomer-2);
7-(3,5-dimethylisoxazol-4-yl)-6-methoxy-2-(pyridin-2-yl)ethyl)-2H-benzo[b][1,4]oxazin-3(4H)-one;
7-(3,5-dimethylisoxazol-4-yl)-6-methoxy-2,2-dimethyl-4-(pyridin-3-ylmethyl)-2H-benzo[b][1,4]oxazin-3(4H)-one;
7-(3,5-dimethylisoxazol-4-yl)-6-methoxy-4-(piperidin-4-ylmethyl)-2H-benzo[b][1,4]oxazin-3(4H)-one;
4-(4-chlorobenzyl)-7-(3,5-dimethyl-1H-pyrazol-4-yl)-6-methoxy-2H-benzo[b][1,4]oxazin-3(4H)-one;
7-(3,5-dimethylisoxazol-4-yl)-4-((6-hydroxypyridin-3-yl)methyl)-6-methoxy-2H-benzo[b][1,4]oxazin-3(4H)-one;
7-(3,5-dimethylisoxazol-4-yl)-6-(2-methoxyethoxy)-4-(pyridin-4-ylmethyl)-2H-benzo[b][1,4]oxazin-3(4H)-one;
7-(3,5-dimethylisoxazol-4-yl)-6-methoxy-4-((1-propionylpiperidin-4-yl )methyl)-2H-benzo[b][1,4]oxazin-3(4H)-one;
N-(4-(4-chlorobenzyl)-6-methoxy-3-oxo-3,4-dihydro-2H-benzo[b][1,4]oxazin-7-yl)-3,5-dimethylisoxazole-4-carboxamide;
4-(4-chlorobenzyl)-7-((3,5-dimethylisoxazol-4-yl)amino)-6-methoxy-2H-benzo[b][1,4]oxazin-3(4H)-one, or a pharmaceutically acceptable salt or a pharmaceutically acceptable stereoisomer thereof.

9. A pharmaceutical composition comprising a therapeutically effective amount of at least one compound of formula (I) according to claim 1, or a pharmaceutically acceptable salt or a pharmaceutically acceptable stereoisomer thereof and at least one pharmaceutically acceptable carrier or excipient including mixtures thereof in all ratios.

* * * * *